US006998415B2

(12) United States Patent
Talley et al.

(10) Patent No.: US 6,998,415 B2
(45) Date of Patent: Feb. 14, 2006

(54) SUBSTITUTED SULFONYLPHENYLHETEROCYCLES AS CYCLOOXYGENASE-2 AND 5-LIPOXYGENASE INHIBITORS

(75) Inventors: John J. Talley, Brentwood, MO (US); James A. Sikorski, Des Peres, MO (US); Balekudru Devadas, Chesterfield, MO (US); Matthew J. Graneto, St. Louis, MO (US); Jeffery S. Carter, Chesterfield, MO (US); Bryan H. Norman, Indianapolis, IN (US); Roland S. Rogers, deceased, late of Louisville, KY (US); by Kathy L. Rogers, legal representative, Louisville, KY (US); Hwang-Fun Lu, Ballwin, MO (US); David L. Brown, Chesterfield, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/757,606

(22) Filed: Jan. 12, 2004

(65) Prior Publication Data

US 2004/0147565 A1    Jul. 29, 2004

Related U.S. Application Data

(63) Continuation of application No. 10/004,960, filed on Dec. 4, 2001, now Pat. No. 6,677,364, which is a continuation of application No. 09/549,830, filed on Apr. 14, 2000, now abandoned, which is a continuation of application No. 08/952,661, filed as application No. PCT/US96/08183 on May 31, 1996, now abandoned.

(51) Int. Cl.
*A61K 31/415* (2006.01)
*C07D 23/00* (2006.01)
*A61P 29/00* (2006.01)

(52) U.S. Cl. ............... 514/406; 514/407; 548/356.1; 548/364.1

(58) Field of Classification Search ............ 548/356.1, 548/364.1; 514/406, 407
See application file for complete search history.

(56) References Cited

U.S. PATENT DOCUMENTS

| | | | |
|---|---|---|---|
| 3,644,499 A | 2/1972 | Murphy | 562/115 |
| 3,647,858 A | 3/1972 | Hinkley | 560/11 |
| 3,707,475 A | 12/1972 | Lombardino | 548/343.1 |
| 3,743,656 A | 7/1973 | Brown | 549/79 |
| 3,901,908 A | 8/1975 | Fitzi | 548/343.5 |
| 3,984,431 A | 10/1976 | Gueremy et al. | 548/376.1 |
| 4,011,328 A | 3/1977 | Pinhas et al. | 514/277 |
| 4,051,250 A | 9/1977 | Dahm et al. | 514/376 |
| 4,146,721 A | 3/1979 | Rainer | 548/365.7 |
| 4,302,461 A | 11/1981 | Cherkofsky | 514/445 |
| 4,372,954 A | 2/1983 | Moreau et al. | 514/238.5 |
| 4,381,311 A | 4/1983 | Haber | 514/438 |
| 4,427,693 A | 1/1984 | Haber | 514/438 |
| 4,472,422 A | 9/1984 | Whitney | 514/400 |
| 4,503,065 A | 3/1985 | Wilkerson | 514/396 |
| 4,533,666 A | 8/1985 | Matsumoto et al. | 514/277 |
| 4,576,958 A | 3/1986 | Wexler | 514/400 |
| 4,590,205 A | 5/1986 | Haber | 514/438 |
| 4,632,930 A | 12/1986 | Carini et al. | 514/365 |
| 4,686,231 A | 8/1987 | Bender et al. | 514/333 |
| 4,820,827 A | 4/1989 | Haber | 549/78 |
| 4,822,805 A | 4/1989 | Takasugi et al. | 514/341 |
| 4,914,121 A | 4/1990 | Sawai et al. | 514/406 |
| 5,051,518 A | 9/1991 | Murray et al. | 548/375.1 |
| 5,098,932 A | 3/1992 | Hamon | 514/462 |
| 5,134,142 A | 7/1992 | Matsuo et al. | 514/253.09 |
| 5,169,857 A | 12/1992 | Angerbauer et al. | 514/344 |
| 5,234,939 A | 8/1993 | Hamon. | 514/400 |
| 5,234,950 A | 8/1993 | Edwards et al. | 514/475 |
| 5,240,941 A | 8/1993 | Bruneau | 514/312 |
| 5,242,940 A | 9/1993 | Wachter et al. | 514/406 |
| 5,298,521 A | 3/1994 | Ferro | 514/406 |
| 5,302,603 A | 4/1994 | Crawley et al. | 514/336 |
| 5,308,852 A | 5/1994 | Girard et al. | 514/336 |
| 5,344,991 A | 9/1994 | Reitz et al. | 568/34 |
| 5,354,865 A | 10/1994 | Dellaria et al. | 546/158 |
| 5,356,989 A | 10/1994 | Tachika et al. | 524/608 |
| 5,364,877 A | 11/1994 | Bruneau et al. | 514/414 |
| 5,364,977 A | 11/1994 | Asai et al. | 568/720 |
| 5,373,007 A | 12/1994 | Bruneau et al. | 514/224.2 |
| 5,380,738 A | 1/1995 | Norman et al. | 514/304 |
| 5,393,790 A | 2/1995 | Reitz et al. | 514/709 |
| 5,401,765 A | 3/1995 | Lee | 548/406 |
| 5,424,320 A | 6/1995 | Fortin et al. | 514/337 |
| 5,643,933 A | 7/1997 | Talley et al. | 514/327 |
| 6,511,989 B1 * | 1/2003 | Heitsch et al. | 514/311 |

FOREIGN PATENT DOCUMENTS

| | | |
|---|---|---|
| EP | 026 928 | 4/1981 |
| EP | 372 445 | 6/1990 |

(Continued)

OTHER PUBLICATIONS

Numata et al., 1996, CAS:125:114611.*

(Continued)

*Primary Examiner*—Taofiq Solola
*Assistant Examiner*—Robert Shiao
(74) *Attorney, Agent, or Firm*—Philip B. Polster, II; Charles W. Ashbrook

(57) ABSTRACT

This invention is in the field of antiinflammatory pharmaceutical agents and specifically relates to compounds, compositions and methods for treating disorders mediated by cyclooxygenase-2 or 5-lipoxygenase, such as inflammation.

11 Claims, No Drawings

FOREIGN PATENT DOCUMENTS

| | | |
|---|---|---|
| EP | 485 111 | 5/1992 |
| EP | 592 664 | 4/1994 |
| WO | WO 92/05162 | 4/1992 |
| WO | WO 92/19604 | 11/1992 |
| WO | WO 93/14082 | 7/1993 |
| WO | WO 94/13635 | 6/1994 |
| WO | WO 94/15932 | 7/1994 |
| WO | WO 94/20480 | 9/1994 |
| WO | WO 94/26731 | 11/1994 |
| WO | WO 94/27980 | 12/1994 |
| WO | WO 95/00501 | 1/1995 |
| WO | WO 95/30669 | 11/1995 |

OTHER PUBLICATIONS

Crawley et al., "Methoxytetrahydropyrans. A new series of selective and orally potent 5-lipoxygenase inhibitors," J. Med. Chem., 35(14):2600-2609 (1992).

Grimmett, "Advances in Imidazole Chemistry," Advances in Heterocyclic Chemistry, 12:140 (1970).

International Search Report, Written Opinion, and Preliminary Examination Report for International Application No. PCT/US96/08183 (filed May 31, 1996).

Miyaura et al., "The Palladium-Catalyzed Cross-Coupling Reaction of Phenylboronic Acid with Haloarenes in the Presence of Bases," Synth. Commun., 11:513 (1981).

* cited by examiner

SUBSTITUTED SULFONYLPHENYLHETEROCYCLES AS CYCLOOXYGENASE-2 AND 5-LIPOXYGENASE INHIBITORS

FIELD OF THE INVENTION

This invention is in the field of antiinflammatory pharmaceutical agents and specifically relates to compounds, compositions and methods for treating disorders mediated by cyclooxygenase-2 or 5-lipoxygenase, such as inflammation and allergic conditions such as asthma.

BACKGROUND OF THE INVENTION

Prostaglandins play a major role in the inflammation process, and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway including the enzyme cylooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

In another portion of the arachnidonic acid pathway, physiologically active leukotrienes, such, as leukotriene $B_4$ ($LTB_4$), leukotriene $C_4$ ($LTC_4$) and leukotriene $D_4$ ($LTD_4$) and other metabolites, are produced by the 5-lipoxygenase-mediated (5-LO) oxidation of arachidonic acid. These leukotrienes have been implicated in various inflammation-related disorders and allergic diseases, and thus compounds which inhibit 5-lipoxygenase are useful in the treatment of disease states in which leukotrienes play an important role.

It is believed that selective dual inhibitors of both cyclooxygenase-2 and 5-lipoxygenase, which affect the two enzymes at low concentrations, will more completely and permanently affect the damage caused by the various diseases and disorders mediated by cyclooxygenase-2 and 5-lipoxygenase but without the gastrointestinal side effects associated with traditional NSAIDs.

The references below that disclose antiinflammatory activity, show continuing efforts to find a safe and effective antiinflammatory agent. The novel compounds disclosed herein are such safe and also effective antiinflammatory agents furthering such efforts. The invention's compounds are found to show usefulness in vivo as antiinflammatory agents with minimal side effects. The compounds disclosed herein preferably selectively inhibit cyclooxygenase-2 over cyclooxygenase-1.

Compounds which selectively inhabit cyclooxygenase-2 have been described in U.S. Pat. Nos. 5,330,738, 5,344,991, 5,393,790 and WO documents WO94/15932, WO94/27980, WO95/00501, WO94/13635, WO94/20480, and WO94/26731.

Compounds which inhibit 5-lipoxygenase have been described in U.S. Pat. Nos. 5,364,877, 5,302,603, 5,234,950, 5,098,932 and 5,354,865, among others.

Compounds which inhibit cyclooxygenase and 5-lipoxygenase have been described in U.S. Pat. Nos. 5,298,521, 5,242,940, 5,234,939, and 5,356,898, among others. However, these previous mixed inhibitors do not selectively inhibit cyclooxygenase-2 and therefore still cause the gastrointestinal side effects which substantially reduce their usage and effectiveness.

The invention's compounds are found to show usefulness in vivo as dual inhibitors of cyclooxygenase-2 and 5-lipoxygenase with minimal side effects.

DESCRIPTION OF THE INVENTION

A class of compounds useful in treating cyclooxygenase-2 and 5-lipoxygenase-mediated disorders is defined by Formula I:

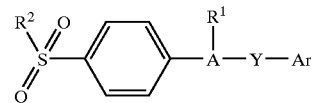

wherein A is a 5- or 6-member ring substituent selected from partially unsaturated or unsaturated heterocyclo and carbocyclic rings, wherein A is optionally substituted with a radical selected from acyl, halo, alkyl, haloalkyl, cyano, nitro, carboxyl, alkoxy, oxo, aminocarbonyl, alkoxycarbonyl, carboxyalkyl, cyanoalkyl, and hydroxyalkyl;

wherein Y is a radical selected from oxy, thio, sulfinyl, sulfonyl, alkyl, alkenyl, alkynyl, alkyloxy, alkylthio, alkylcarbonyl, cycloalkyl, aryl, haloalkyl, hydroxyalkyl, hydroxyalkyloxy, hydroxyalkyloxyalkyl, hydroxyalkylthio, hydroxyalkylthioalkyl-, oximinoalkoxy, oximinoalkoxyalkyl, (alkyl)oximinoalkoxy, (alkyl)oximinoalkoxyalkyl, oximinoalkylthio, oximinoalkylthioalkyl, (alkyl)oximinoalkylthio, (alkyl)oximinoalkylthioalkyl, carbonylalkyloxy, carbonylalkyloxyalkyl, carbonylalkylthio, carbonylalkylthioalkyl, heterocyclo, cycloalkenyl, aralkyl, heterocycloalkyl, acyl, alkylthioalkyl, alkyloxyalkyl, alkenylthio, alkynylthio, alkenyloxy, alkynyloxy, alkenylthioalkyl, alkynylthioalkyl, alkenyloxyalkyl, alkynloxyalkyl, arylcarbonyl, aralkylcarbonyl, aralkenyl, alkylarylalkynyloxy, alkylarylalkenyloxy, alkylarylalkynylthio, alkylarylalkenylthio, haloalkylcarbonyl, alkoxyalkyl, alkylaminocarbonylalkyl, heteroaralkoxyalkyl, heteroaryloxyalkyl, heteroarylthioalkyl, heteroaralkylthioalkyl, heteroaralkoxy, heteroaralkylthio, heteroaryloxy, heteroarylthio, arylthioalkyl, aryloxyalkyl, haloaryloxyalkyl, aralkylthioalkyl, aralkoxyalkyl, alkoxyaralkoxyalkyl, alkoxycarbonylalkyl, alkoxycarbonylcyanoalkenyl, aminocarbonylalkyl, N-alkylaminocarbonyl, N-arylaminocarbonyl, N,N-dialkylaminocarbonyl, N-alkyl-N-arylaminocarbonyl, cycloalkylaminocarbonyl, heterocycloaminocarbonyl, carboxyalkylaminocarbonyl, alkylcarbonylalkyl, aralkoxycarbonylalkylaminocarbonyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyl-N-aralkylamino, N-alkyl-N-arylamino, aminoalkyl, N-alkylaminoalkyl, N,N-dialkylaminoalkyl, N-arylaminoalkyl, N-aralkylaminoalkyl, N-alkyl-N-aralkylaminoalkyl, N-alkyl-N-arylaminoalkyl, aminoalkyoxy, aminoalkoxyalkyl, aminoalkylthio, aminoalkylthioalkyl, cycloalkyloxy, cycloalkylalkyloxy, cycloalkylthio, cycloalkylalkylthio, aryloxy, aralkoxy, arylthio, aralkylthio, alkylsulfinyl, alkylsulfonyl, aminosulfonyl, N-alkylaminosulfonyl, N-arylaminosulfonyl, arylsulfonyl, N,N-dialkylaminosulfonyl, N-alkyl-N-arylaminosulfonyl,

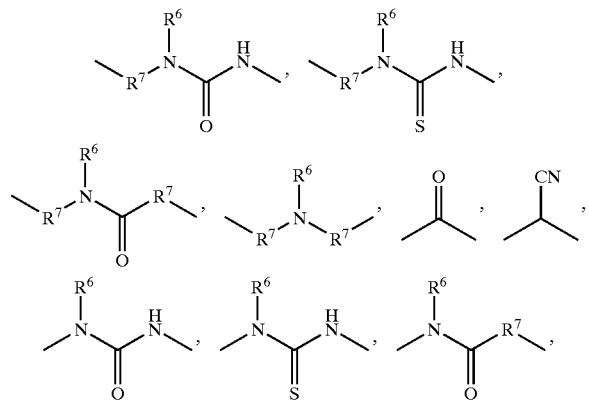

wherein Ar is selected from aryl and heteroaryl, wherein Ar is optionally substituted with one or two substituents selected from halo, hydroxyl, mercapto, amino, nitro, cyano, carbamoyl, alkyl, alkenyloxy, alkoxy, alkylthio, alkylsulfinyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, alkoxycarbonylalkoxy and

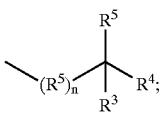

wherein $R^1$ is one or more substituents selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl and amino;

wherein $R^3$ and $R^4$ together form a group of the formula —B—X—$B^1$ which together with the carbon atom to which B and $B^1$ are attached, defines a ring having 6 ring atoms, wherein B and $B^1$, which may be the same or different, each is alkylene and X is oxy, and which ring may bear one, two or three substituents, which may be the same or different, selected from hydroxyl, alkyl, alkoxy, alkenyloxy and alkynyloxy;

wherein $R^5$ is selected from hydroxyl, alkoxy, alkylcarbonyloxy, arylcarbonyloxy, carboxyl, aminocarbonyl, alkylaminocarbonyl, alkoxycarbonyl, acyl, and cyano;

wherein $R^6$ is selected from hydrido, alkyl, aryl and aralkyl;

wherein $R^7$ is selected from alkyl, alkoxy, alkenyl and alkynyl;

wherein $R^8$ is oximino optionally substituted with alkyl; and wherein n is 0 or 1;

provided Ar is substituted with

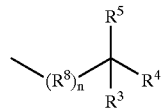

when A is oxazolyl;

or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of the invention would be useful to treat arthritis, including but not limited to rheumatoid arthritis, spondyloarthopathies, gouty arthritis, osteoarthritis, systemic lupus erythematosus and juvenile arthritis Such compounds of the invention would be useful in the treatment of asthma, bronchitis, menstrual cramps, tendinitis, bursitis, skin-related conditions such as psoriasis, eczema, burns and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis, and for the prevention or treatment of cancer, such as colorectal cancer. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as retinitis, retinopathies, uveitis, ocular photophobia, and of acute injury to the eye tissue. The compounds would also be useful in the treatment of pulmonary inflammation, such as that associated with viral infections and cystic fibrosis. The compounds would also be useful for the treatment or certain central nervous system disorders such as cortical dementias including Alzheimer's disease. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, atherosclerosis and central nervous system damage resulting from stroke, ischemia and trauma. The compounds would also be useful in the treatment of pain, but not limited to postoperative pain, dental pain, muscular pain, and pain resulting from cancer.

Besides being useful for human treatment, these compounds are also useful for treatment of mammals, including horses, dogs, cats, rats, mice, sheep, pigs, etc.

The present compounds may also be used in co-therapies, partially or completely, in place of other conventional anti-inflammatories, such as together with steroids, NSAIDs, $LTB_4$ antagonists and $LTA_4$ hydrolase inhibitors.

Suitable LTB₄ inhibitors include, among others, ebselen, Bayer Bay-x-1005, Ciba Geigy compound CGS-25019C, Leo Dermark compound ETH-615, Lilly compound LY-293111, Ono compound ONO-4057, Terumo compound TMK-688, Lilly compounds LY-213024, 264086 and 292728, Ono compound ONO-LB457, Searle compound SC-53228, calcitrol, Lilly compounds LY-210073, LY223982, LY233469, and LY255283, ONO compound ONO-LB-448, Searle compounds SC-41930, SC-50605 and SC-51146, and SK&F compound SKF-104493. Preferably, the LTB₄ inhibitors are selected from ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, masoprocol, tenidap, zileuton, pranlukast, tepoxalin, rilopirox, flezelastine hydrochloride, enazadrem phosphate, and bunaprolast.

The present invention preferably includes compounds which selectively inhibit cyclooxygenase-2 over cyclooxygenase-1 as well as inhibit the 5-lipoxygenase enzyme. Preferably, the compounds have a cyclooxygenase-2 IC$_{50}$ of less than about 0.5 μM, and also have a selectivity ratio of cyclooxygenase-2 inhibition over cyclooxygenase-1 inhibition of at least 50, and more preferably of at least 100, and inhibit 5-lipoxygenase at less than about 10 μM. Even more preferably, the compounds have a cyclooxygenase-1 IC$_{50}$ of greater than about 1 μM, and more preferably of greater than 20 μM and have a 5-lipoxygenase IC$_{50}$ of less than about 1 μM. Such preferred selectivity may indicate an ability to reduce the incidence of common NSAID-induced side effects.

A preferred class of compounds consists of those compounds of Formula I wherein A is a radical selected from thienyl, oxazolyl, furyl, pyrrolyl, thiazolyl, imidazolyl, isothiazolyl, triazolyl, isoxazolyl, pyrazolyl, cyclopentenyl, phenyl, and pyridyl, wherein A is optionally substituted with a radical selected from acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, lower carbonylalkyloxyalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylthio, lower alkylcarbonyl, lower cycloalkyl, phenyl, lower haloalkyl, 5- or 6-membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower alkylarylalkynyloxy, lower alkylarylalkenyloxy, lower alkylarylalkynylthio, lower alkylarylalkenylthio, lower haloalkylcarbonyl, lower alkylaminocarbonylalkyl, lower heteroaralkoxyalkyl, lower heteroaryloxyalkyl, lower heteroarylthioalkyl, lower heteroaralkylthioalkyl, lower heteroaralkoxy, lower heteroaralkylthio, lower heteroaryloxy, lower heteroarylthio, lower arylthioalkyl, lower aryloxyalkyl, lower aralkylthioalkyl, lower aralkoxyalkyl, lower alkoxyaralkoxyalkyl, lower alkoxycarbonylalkyl, lower alkoxycarbonylcyanoalkenyl, lower aminocarbonylalkyl, lower N-alkylaminocarbonyl, N-phenylaminocarbonyl, lower N,N-dialkylaminocarbonyl, lower N-alkyl-N-arylaminocarbonyl, lower cycloalkylaminocarbonyl, lower heterocycloaminocarbonyl, lower carboxyalkylaminocarbonyl, lower alkylcarbonylalkyl, lower aralkoxycarbonylalkylaminocarbonyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-phenylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, lower aminoalkoxy, lower aminoalkoxyalkyl, lower aminoalkylthio, lower aminoalkylthioalkyl, lower cycloalkyloxy, lower cycloalkylalkyloxy, lower cycloalkylthio, lower cycloalkylalkylthio, phenyloxy, lower aralkoxy, phenylthio, lower aralkylthio, lower alkylsulfinyl, lower alkylsulfonyl, aminosulfonyl, lower N-alkylaminosulfonyl, lower N-arylaminosulfonyl, lower arylsulfonyl, lower N,N-dialkylaminosulfonyl, lower N-alkyl-N-arylaminosulfonyl,

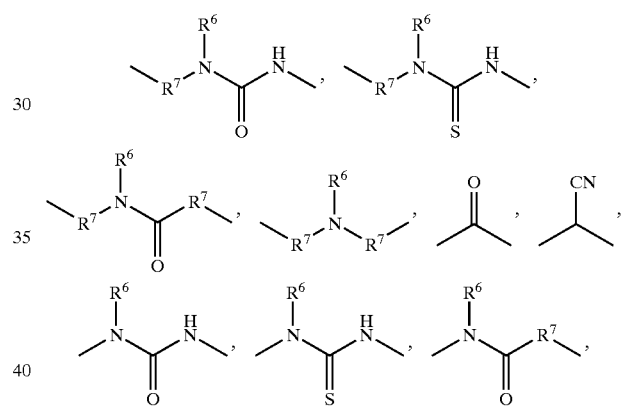

wherein Ar is selected from aryl selected from phenyl, biphenyl and naphthyl, and 5- and 6-membered heteroaryl, wherein Ar is optionally substituted with one or two substituents selected from halo, hydroxyl, mercapto, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower alkoxycarbonylalkoxy and

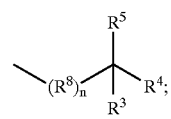

wherein R¹ is at least one substituent selected from 5- and 6-membered heterocyclo, lower cycloalkyl, lower cycloalkenyl and aryl selected from phenyl, biphenyl and naphthyl, where R¹ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; wherein $R^3$ and $R^4$ together form a group of the formula —B—X—$B^1$ which together with the carbon atom to which B and $B^1$ are attached, defines a ring having 6 ring atoms, wherein B and $B^1$, which may be the same or different, each is alkylene and X is oxy, and which ring may bear one, two or three substituents, which may be the same or different, selected from hydroxyl, lower alkyl, lower alkoxy, lower alkenyloxy and lower alkynyloxy; wherein $R^5$ is selected from hydroxyl, lower alkoxy, lower alkylcarbonyloxy, phenylcarbonyloxy, carboxyl, aminocarbonyl, lower alkylaminocarbonyl, lower alkoxycarbonyl, lower acyl, and cyano; wherein $R^6$ is selected from hydrido, lower alkyl, phenyl and lower aralkyl; wherein $R^7$ is selected from lower alkyl, lower alkoxy, lower alkenyl and lower alkynyl; wherein $R^8$ is oximino optionally substituted with alkyl; and wherein n is 0 or 1; or a pharmaceutically-acceptable salt thereof.

A more preferred class of compounds consists of those compounds of Formula I wherein A is a radical selected from thienyl, oxazolyl, furyl, pyrrolyl, thiazolyl, imidazolyl, isothiazolyl, triazolyl, isoxazolyl, pyrazolyl, cyclopentenyl, phenyl, and pyridyl, wherein A is optionally substituted with a radical selected from acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, lower carbonylalkyloxyalkyl, lower hydroxyalkylthio, lower hydroxyalkylthioalkyl, lower oximinoalkalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylthio, lower alkylcarbonyl, lower cycloalkyl, phenyl, lower haloalkyl, 5- or 6-membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower alkylarylalkynyloxy, lower alkylarylalkynylthio, lower haloalkylcarbonyl, lower alkylaminocarbonylalkyl, lower arylthioalkyl, lower aryloxyalkyl, lower aralkylthioalkyl, lower aralkoxyalkyl, lower alkoxycarbonylalkyl, lower aminocarbonylalkyl, lower N-alkylaminocarbonyl, N-phenylaminocarbonyl, lower alkylcarbonylalkyl, lower N-alkylamino, N-phenylamino, lower N-aralkylamino, lower aminoalkyl, lower N-alkylaminoalkyl, lower N-arylaminoalkyl, lower N-aralkylaminoalkyl, lower aminoalkoxy, lower aminoalkoxyalkyl, lower aminoalkylthio, lower aminoalkylthioalkyl, lower cycloalkyloxy, lower cycloalkylalkyloxy, lower cycloalkylthio, lower cycloalkylalkylthio, phenyloxy, lower aralkoxy, phenylthio, lower aralkylthio, lower alkylsulfinyl, lower alkylsulfonyl, aminosulfonyl, lower N-alkylaminosulfonyl, N-phenylaminosulfonyl, phenylsulfonyl, oximino,

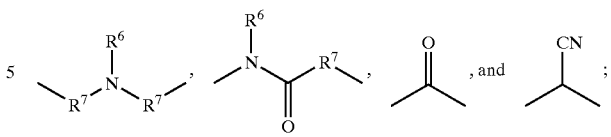

wherein Ar is selected from aryl selected from phenyl, biphenyl, naphthyl, and, 5- and 6-membered heteroaryl, wherein Ar is optionally substituted with one or two substituents selected from halo, hydroxyl, mercapto, amino, nitro, cyano, lower alkyl, lower alkoxy, and

wherein $R^1$ is at least one substituent selected from 5- and 6-membered heteroaryl, and aryl selected from phenyl, biphenyl and naphthyl, where $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, nitro, lower alkoxyalkyl, lower alkylsulfinyl, halo, lower alkoxy and lower alkylthio; wherein $R^2$ is selected from lower alkyl and amino; wherein $R^3$ and $R^4$ together form a tetrahydropyran ring and which ring may bear one, two or three substituents, which may be the same or different, selected from hydroxyl, lower alkyl, and lower alkoxy; wherein $R^5$ is selected from hydroxyl and lower alkoxy; wherein $R^6$ is selected from hydrido, lower alkyl, phenyl and lower aralkyl; and wherein $R^7$ is selected from lower alkyl, lower alkoxy, lower alkenyl and lower alkynyl; or a pharmaceutically-acceptable salt thereof.

An even more preferred class of compounds consists of those compounds of Formula I wherein A is a radical selected from thienyl, oxazolyl, furyl, pyrrolyl, thiazolyl, triazolyl, imidazolyl, isoxazolyl, pyrazolyl, cyclopentenyl, phenyl, and pyridyl, wherein A is optionally substituted with a radical selected from acyl, halo, lower alkyl, lower haloalkyl, oxo, cyano, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkynyl, lower alkenyl, aryl, lower cycloalkyl, 5- or 6-membered heterocyclo, aralkyl, lower alkyloxy, aryloxy, arylthio, 5- or 6-membered heterocyclooxy, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkyloxyalkyl, lower alkylthioalkyl, lower hydroxyalkyloxy, lower alkylarylalkynyloxy, lower alkoxycarbonylalkyl, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, lower carbonylalkyloxyalkyl,

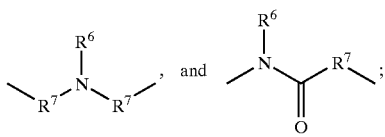

wherein Ar is selected from phenyl, thienyl, oxazolyl, furyl, pyrrolyl, thiazolyl, imidazolyl, isothiazolyl, isoxazolyl, pyrazolyl, and pyridyl, wherein Ar is optionally substituted with one or two substituents selected from halo, hydroxyl, mercapto, lower alkyl, lower alkoxy, and

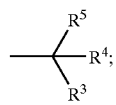

wherein $R^1$ is at least one substituent selected from thienyl, oxazolyl, furyl, pyrrolyl, thiazolyl, imidazolyl, isothiazolyl, isoxazolyl, pyrazolyl, cyclopentenyl, pyridyl, and phenyl, where $R^1$ is optionally substituted at a substitutable position with one or more radicals selected from lower alkyl, lower haloalkyl, hydroxyl, lower hydroxyalkyl, lower haloalkoxy, nitro, lower alkoxyalkyl, halo, lower alkoxy and lower alkylthio; wherein $R^2$ is selected from lower alkyl and amino; wherein $R^3$ and $R^4$ together form a tetrahydropyran ring, and which ring may bear one, two or three substituents, which may be the same or different, selected from hydroxyl, lower alkyl, and lower alkoxy; wherein $R^5$ is selected from hydroxyl and lower alkoxy; wherein $R^6$ is selected from hydrido, and lower alkyl; and wherein $R^7$ is selected from lower alkyl and lower alkoxy; or a pharmaceutically-acceptable salt thereof.

A class of compounds of particular interest consists of those compounds of Formula I wherein A is a radial selected from thienyl, oxazolyl, furyl, pyrrolyl, triazolyl, thiazolyl, imidazolyl, isoxazolyl, pyrazolyl, cyclopentenyl, phenyl, and pyridyl, wherein A is optionally substituted with a radical selected from acyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl; wherein Y is a radical selected from oxy, ethyl, propyl, isopropyl, butyl, 1-propynyl, 2-propynyl, methyloxy, ethyloxy, propyloxy, methylthio, (Z)-1-propenyloxy, (E)-2-propenyloxy, (Z)-2-propenyloxy, (E)-1-propenyloxy, (Z)-1-propenyloxymethyl, (E)-2-propenyloxymethyl, (Z)-2-propenyloxymethyl, (E)-1-propenyloxymethyl, 1-propynyloxy, 2-propynyloxy, 1-propynylthio, 2-propynylthio, hydroxymethyloxy, 1-hydroxyethyloxy, 2-hydroxypropyloxy, hydroxymethyloxymethyl, 1-hydroxyethyloxymethyl, 2-hydroxypropyloxymethyl, methyloxymethyl, ethyloxymethyl, propyloxymethyl, 1-propynyloxymethyl, oximinomethyloxy, oximinomethyloxymethyl, (methyl)oximinomethyloxy, (methyl)oximinomethyloxymethyl, triazolylmethyloxy, triazolylmethyloxymethyl, 1-(methoxycarbonyl)ethyl, methylthiomethyl, ethylthiomethyl, methylphenylpropynyloxy, N-ethyl-N-methylaminocarbonylmethyloxy, N-ethyl-N-methylaminoethyloxy, carbonylmethyloxy, carborylbutyloxy, and carbonylmethyloxymethyl; wherein Ar is selected from thienyl, pyridyl, thiazolyl, and phenyl, where Ar is optionally substituted with one or two substituents selected from fluoro, chloro, bromo, hydroxyl, mercapto, methyl, methoxy, and

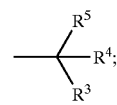

wherein $R^1$ is selected from thienyl, oxazolyl, furyl, pyrrolyl, thiazolyl, imidazolyl, isoxazolyl, pyrazolyl, pyridyl, and phenyl, where $R^1$ is optionally substituted at a substitutable position with one or more radicals selected from methyl, trifluoromethyl, hydroxyl, hydroxymethyl, trifluoromethoxy, nitro, methoxymethyl, fluoro, chloro, bromo, methoxy and methylthio; wherein $R^2$ is methyl or amino; wherein $R^3$ and $R^4$ together form a tetrahydropyran ring, and which ring may bear one, two or three substituents, which may be the same or different, selected from hydroxyl, methyl, and methoxy; and wherein $R^5$ is selected from hydroxyl and methoxy; or a pharmaceutically-acceptable salt thereof.

Within Formula I there is a subclass of compounds of high interest represented by Formula II:

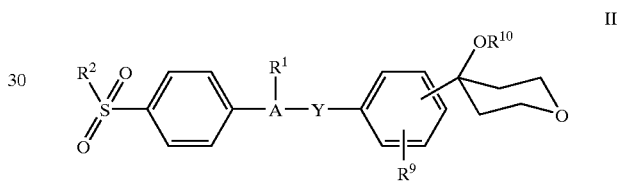

wherein A is a ring substituent selected from thienyl, oxazolyl, furyl, pyrrolyl, thiazolyl, imidazolyl, isothiazolyl, triazolyl, isoxazolyl, pyrazolyl, cyclopentenyl, phenyl, and pyridyl; wherein A is optionally substituted with a radical selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

wherein Y is a radical selected from oxy, thio, sulfinyl, sulfonyl, lower alkyl, lower alkynyl, lower alkenyl, lower hydroxyalkyl, aryl, lower cycloalkyl, 5- or 6-membered heterocyclo, aralkyl, lower alkyloxy, aryloxy, arylthio, lower cycloalkyloxy, 5- or 6-membered heterocylooxy, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkyloxyalkyl, lower alkylthioalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower alkylarylalkynyloxy, lower dialkylaminoalkyloxy, lower dialkylaminocarbonylalkyloxy, lower alkoxycarbonylalkyl, lower carbonylalkylthio, lower carbonylalkylthioalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, and lower carbonylalkyloxyalkyl;

wherein $R^1$ is a substituent selected from 5- and 6-member heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, lower alkoxyalkyl, lower alkylsulfinyl, halo, lower alkoxy and lower alkylthio;

wherein $R^2$ is selected from lower alkyl and amino;

wherein $R^9$ is one or two substituents selected from halo, hydroxyl, amino, nitro, cyano, carbamoyl, alkyl, alkenyloxy, alkoxy, alkylthio, alkylsulfinyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, and alkoxycarbonylalkoxy; and wherein $R^{10}$ is selected from hydrido, alkyl, alkenyl, alkynyl, cyanoalkyl, alkanoyl, and benzoyl optionally substituted with a substituent selected from halo, alkyl, and alkoxy;

or a pharmaceutically-acceptable salt thereof.

A preferred class of compounds consists of those compounds of Formula II wherein A is a ring substituent selected from thienyl, oxazolyl, furyl, pyrrolyl, thiazolyl, imidazolyl, triazoylyl, isoxazolyl, pyrazolyl, cyclopentenyl, phenyl, and pyridyl; wherein A is optionlly substituted with a radical selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, lower alkyl, lower alkynyl, 5- or 6-membered heterocyclo, lower heterocyloalkyloxyalkyl, lower hydroxyalkyl, lower alkyloxy, lower alkylthio, lower alkyloxyalkyl, lower alkenyloxy, lower alkenyloxyalkyl, lower alkynyloxy, lower alkynylthio, lower alkynyloxyalkyl, lower alkylthioalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylarylalkynyloxy, lower dialkylaminoalkyloxy, lower dialkylaminocarbonylalkyloxy, lower alkoxycarbonylalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, and lower carbonylalkyloxyalkyl; wherein $R^1$ is phenyl optionally substituted at a substitutable position with one or more radicals selected from lower alkyl, lower haloalkyl, hydroxyl, lower hydroxyalkyl, halo, and lower alkoxy; wherein $R^2$ is selected from lower alkyl and amino; wherein $R^9$ is one or two substituents selected from halo, hydroxyl, amino, lower alkyl, lower alkoxy; and wherein $R^{10}$ is selected from hydrido, and lower alkyl; or a pharmaceutically-acceptable salt thereof.

A class of compounds of particular interest consists of those compounds of Formula II wherein A is a radical selected from thienyl, oxazolyl, furyl, pyrrolyl, thiazolyl, imidazolyl, isoxazolyl, pyrazolyl, cyclopentenyl, phenyl, and pyridyl; wherein A is optionally substituted with a radical selected from formyl, fluoro, chloro, bromo, hydroxyl, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, oxo, cyano, nitro, carboxyl, methoxy, ethoxy, propoxy, n-butoxy, pentoxy, hexyloxy, methylenedioxy, aminocarbonyl, methoxycarbonyl, carboxypropyl, carboxymethyl, carboxyethyl, cyanomethyl, and hydroxymethyl; wherein Y is a radical selected from oxy, ethyl, propyl, isopropyl, butyl, 1-propynyl, 2-propynyl, methyloxy, ethyloxy, propyloxy, methylthio, (Z)-1-propenyloxy, (E)-2-propenyloxy, (Z)-2-proenyloxy, (E)-1-propenyloxy, (Z)-1-propenyloxymethyl, (E)-2-propenyloxymethyl, (Z)-2-propenyloxymethyl, (E)-1-propenyloxymethyl, 1-propynyloxy, 2-propynyloxy, 1-propynylthio, 2-propynylthio, hydroxymethyl, hydroxyethyl, hydroxypropyl, hydroxymethyloxy, 1-hydroxyethyloxy, 2-hydroxypropyloxy, hydroxymethyloxymethyl, 1-hydroxyethyloxymethyl, 2-hydroxypropyloxymethyl, methyloxymethyl, ethyloxymethyl, propyloxymethyl, 1-propynyloxymethyl, hydroxymethlythio, 1-hydroxyethylthio, 2-hydroxypropylthio, hydroxymethylthiomethyl, 1-hydroxyethylthiomethyl, 2-hydroxypropylthiomethyl, oximinomethylthio, oximinomethylthiomethyl, (methyl)oximinomethylthio, (methyl)oximinomethylthiomethyl, triazolylmethyloxy, triazolylmethyloxymethyl, carbonylmethylthio, carbonylbutylthio, carbonylmethylthiomethyl, oximinomethyloxy, oximinomethyloxymethyl, (methyl)oximinomethyloxy, methylthiomethyl, (methyl)oximinomethyloxymethyl, ethylthiomethyl, 1-(methoxycarbonyl)ethyl, methylphenylpropynyloxy, N-ethyl-N-methylaminocarbonylmethyloxy, N-ethyl-N-methylaminoethyloxy, triazolyl, carbonylmethyloxy, carbonylbutyloxy, and carbonylmethyloxymethyl; wherein $R^1$ is phenyl optionally substituted at a substitutable position with one or more radicals selected from methyl, ethyl, isopropyl, butyl, tert-butyl, isobutyl, pentyl, hexyl, fluoroethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, fluoro, dichloropropyl, hydroxyl, hydroxymethyl, chloro, bromo, methoxy, ethoxy, propoxy, n-butoxy, pentoxy, and hexyloxy; wherein $R^2$ is selected from methyl and amino; wherein $R^9$ is one or two substituents selected from fluoro, chloro, bromo, hydroxyl, amino, methyl, ethyl, isopropyl, butyl, tert-butyl, isobutyl, pentyl, hexyl, methoxy, ethoxy, propoxy, n-butoxy, pentoxy, and hexyloxy; and wherein $R^{10}$ is selected from hydrido, and methyl; or a pharmaceutically-acceptable salt thereof.

A class of compounds of particular interest consists of those compounds of Formula I 4-[2-[[3-fluoro-5-(3,4,5,6-tetrahydro-4-methoxypyran-4-yl)phenoxy]methyl]-4-(3-fluoro-4-methoxyphenyl)oxazol-5-yl]benzenesulfonamide;

4-[2-[[3-fluoro-5-(3,4,5,6-tetrahydro-4-methoxypyran-4-yl)phenoxy]methyl]-4-(3,4-dichlorophenyl)oxazol-5-yl]benzenesulfonamide;

4-[2-[[3-fluoro-5-(3,4,5,6-tetrahydro-4-methoxypyran-4-yl)phenoxy]methyl]-4-(3-fluorophenyl)oxazol-5-yl]benzenesulfonamide;

4-[2-[[3-fluoro-5-(3,4,5,6-tetrahydro-4-methoxypyran-4-yl)phenoxy]methyl]-4-(4-methylphenyl)oxazol-5-yl]benzenesulfonamide;

4-[2-[[3-fluoro-5-(3,4,5,6-tetrahydro-4methoxy-2-methylpyran-4-yl)phenoxy]methyl]-4-phenyloxazol-5-yl]benzenesulfonamide;

4-[2-[[3-fluoro-5-(3,4,5,6-tetrahydro-2,6-dimethyl-4-methoxypyran-4-yl)phenoxy]methyl]-4-phenyloxazol-5-yl]benzenesulfonamide;

[5-[4-(methylsulfonyl)phenyl]-2-[[3-(3,4,5,6-tetrahydro-4-methoxy-2H-pyran-4-yl)phenoxy]methyl]-4-phenyloxazole;

4-[-2-[[3-fluoro-5-(3,4,5,6-tetrahydro-4-methoxypyran-4-yl)phenoxy]methyl]-5-(3-fluoro-4-methoxyphenyl)oxazol-4-yl]benzenesulfonamide;

4-[2-[[3-fluoro-5-(3,4,5,6-tetrahydro-4-methoxypyran-4-yl)phenoxy]methyl]-5-(3,4-dichlorophenyl)oxazol-4-yl]benzenesulfonamide;

4-[2-[[3-fluoro-5-(3,4,5,6-tetrahydro-4-methoxypyran-4-yl)phenoxy]methyl]-5-(3,-fluorophenyl)oxazol-4-yl]benzenesulfonamide;

4-[2-[[3-fluoro-5-(3,4,5,6-tetrahydro-4-methoxypyran-4-yl)phenoxy]methyl]-5-(4-methylphenyl)oxazol-4-yl]benzenesulfonamide;

4-[2-[[3-fluoro-5-(3,4,5,6-tetrahydro-4-methoxy-2-methylpyran-4-yl)phenoxy]methyl]-5-phenyloxazol-4-yl]benzenesulfonamide;

4-[2-[[3-fluoro-5-(3,4,5,6-tetrahydro-2,6-dimethyl-4-methoxypyran-4-yl)phenoxy]methyl]-5-phenyloxazol-4-yl]benzenesulfonamide;

[4-[4-(methylsulfonyl)phenyl]-2-[[3-(3,4,5,6-tetrahydro-4-methoxy-2H-pyran-4-yl)phenoxy]methyl]-5-phenyloxazole;

4-[2-[[4-(3,4,5,6-tetrahydro-4-methoxy-2-methylpyran-4-yl)thien-2-yl]thiomethyl]-5-phenyloxazol-4-yl]benzenesulfonamide;

4-[2-[[4-(3,4,5,6-tetrahydro-4-methoxy-2-methylpyran-4-yl)thien-2-yl]thio]-5-phenyloxaziol-4-yl)]benzenesulfonamide;

4-[2-[[4-(3,4,5,6-tetrahydro-2,6-dimethyl-4-methoxypyran-4-yl)thien-2-yl]thiomethyl]-5-phenyloxazol-4-yl]benzenesulfonamide;

4-[2-[[4-(3,4,5,6-tetrahydro-2,6-dimethyl-4-methoxypyran-4-yl)thien-2-yl]thio]-5-phenyloxazol-4-yl]benzenesulfonamide;

4-[2-[[3-fluoro-5-(tetrahydro-4-methoxypyran-4-yl)phenoxy]methyl]-4-phenyloxazol-5-yl]benzenesulfonamide;

methyl 5-[4-(aminosulfonyl)phenyl]-α-[[3-(tetrahydro-4-methoxypyran-4-yl)phenyl]methyl]-4-phenyloxazole-2-acetate;

N-[2-[5-[4-(aminosulfonyl)phenyl]-4-phenyloxazol-2-yl]ethyl]-2-[3-fluoro-5-(tetrahydro-4-methoxypyran-4-yl)phenoxy-N-methylacetamide;

N-[2-[4-[4-(aminosulfonyl)phenyl]-5-phenyloxazol-2-yl]ethyl]-2-[3-fluoro-5-(tetrahydro-4-methoxypyran-4-yl)phenoxy-N-methylacetamide;

4-[2-[[2-[3-fluoro-5-(tetrahydro-4-methoxypyran-4-yl)phenoxy]ethyl]-N-methylaminoethyl]-4-phenyloxazol-5-yl]benzenesulfonamide;

4-[2-[[2-[3-fluoro-5-(tetrahydro-4-methoxypyran-4-yl)phenoxy]ethyl]-N-methylaminoethyl]-5-phenyloxazol-4-yl]benzenesulfonamide;

4-[2-[[4-[3-[3-fluoro-5-(tetrahydro-4-methoxypyran-4-yl)phenoxy]-1-propynyl]phenyl]methyl]-4-phenyloxazol-5-yl]benzenesulfonamide;

4-[2-[[4-[3-[3-fluoro-5-(tetrahydro-4-hydroxypyran-4-yl)phenoxy]-1-propynyl]-phenyl]methyl]-4-phenyloxazol-5-yl]benzenesulfonamide;

4-[2-[[3-fluoro-5-(tetrahydro-4-methoxypyran-4-yl)phenoxy]methyl]-4-(4-fluoropenyl)oxazol-5-yl]benzenesulfonamide;

4-[2-[4-[[3-fluoro-5-(tetrahydro-4-methoxypyran-4-yl)phenoxy]methyl]phenylmethyl]-4-phenyloxazol-5-yl]benzenesulfonamide;

4-[5-[[3-fluoro-5-(tetrahydro-4-methoxypyran-4-yl)phenoxy]methyl]-3-phenylisoxazol-4-yl]benzenesulfonamide;

4-[2-[[[3-(tetrahydro-4-methoxypyran-4-yl)phenylmethyl]oxy]methyl]-4-phenyloxazol-5-yl]benzenesulfonamide;

4-[2-[[[3-(tetrahydro-4-methoxypyran-4-yl)phenylmethyl]thio]methyl]-4-phenyloxazol-5-yl]benzenesulfonamide;

4-[2-[[[3-(tetrahydro-4-methoxypyran-4-yl)phenylmethyl]thio]ethyl]-4-phenyloxazol-5-yl]benzenesulfonamide;

4-[2-[3-(tetrahydro-4-methoxypyran-4-yl)phenyl]-methoxy]-4-phenyloxazol-5-yl]benzenesulfonamide;

4-[2-[3-(tetrahydro-4-methoxypyran-4-yl)phenyl]methylthio]-4-phenyloxazol-5-yl]benzenesulfonamide;

N-[2-[5-[4-(aminosulfonyl)phenyl]-4-phenyloxazol-2-yl]ethylamino]-2-[3-fluoro-5-(tetrahydro-4-methoxypyran-4-yl)phenoxy]acetamide;

4-[5-(4-chlorophenyl)-3-(3-methoxyphenyl)oxymethyl-1H pyrazole-1-yl]benzenesulfonamide;

4-[5-(4-chlorophenyl)-3-(3-methoxyphenyl)thiomethyl-1H pyrazol-1-yl]benzenesulfonamide;

4-[5-phenyl-3-[[3-(3,4,5,6-tetrahydro-4-methoxy-2H-pyran-4-yl)phenoxy]acetyl]-1H-pyrazol-1-yl]benzenesulfonamide;

1-[4-(methylsulfonyl)phenyl]-2-[[3-(3,4,5,6-tetrahydro-4-methoxy-2H-pyran-4-yl)phenoxy]acetyl]-5-phenylpyrazole;

4-[5-phenyl-3-[[3-flouro-5-(3,4,5,6-tetrahydro-4-4-methoxy-2H-pyran-4-yl)phenoxy]acetyl]-1H-pyrazol-1-yl]benzenesulfonamide;

4-[5-(4-chlorophenyl)-3-[[3-fluoro-5-(3,4,5,6-tetrahydro-4-methoxy-2H-pyran-4-yl)phenoxy]methyl]-1H-pyrazol-1-yl]benzenesulfonamide;

4-[1-phenyl-3-[[3-(3,4,5,6-tetrahydro-4-methoxy-2H-pyran-4-yl)phenoxy]acetyl]-1H-pyrazol-5-yl]benzenesulfonamide;

4-[1-phenyl-3-[[3-flouro-5-(3,4,5,6-tetrahydro-4-methoxy-2H-pyran-4-yl)phenoxy]acetyl]-1H-pyrazol-5-yl]benzenesulfonamide;

4-[1-phenyl-3-[[3-(3,4,5,6-tetrahydro-4-methoxy-2H-pyran-4-yl)benzyloxy]acetyl]-1H-pyrazol-5-yl]benzenesulfonamide;

4-[4-phenyl-2-[[3-(3,4,5,6-tetrahydro-4-methoxy-2-H-pyran-4-yl)phenoxy]acetyl]-5-thiazolyl]benzenesulfonamide;

5-phenyl-4-[4-(methylsulfonyl)phenyl]-2-[[3-(3,4,5,6-tetrahydro-4-methoxy-2H-pyran-4-yl)phenoxy]acetyl]thiazole;

4-[5-phenyl-2-[[3-fluoro-5-(3,4,5,6-tetrahydro-4-methoxy-2H-pyran-4-yl)phenoxy]acetyl]-4-thiazolyl]benzenesulfonamide;

4-[4-phenyl-2-[[3-(3,4,5,6-tetrahydro-4-methoxy-2H-pyran-4-yl)benzyloxy]acetyl]-5-thiazolyl]benzenesulfonamide;

4-[3-phenyl-5-[[3-(3,4,5,6-tetrahydro-4-methoxy-2H-pyran-4-yl)phenoxy]acetyl]-4-isoxazolyl]benzenesulfonamide;

3-phenyl-4-[4-(methylsulfonyl)phenyl]-5-[[3-(3,4,5,6-tetrahydro-4-methoxy-2H-pyran-4-yl)phenoxy]acetyl]isoxazole;

4-[3-phenyl-5-[[3-fluoro-5-(3,4,5,6-tetrahydro-4-methoxy-2H-pyran-4-yl)phenoxy]acetyl]-4-isoxazolyl]benzenesulfonamide;

4-[3-phenyl-5-[[3-(3,4,5,6-tetrahydro-4-methoxy-2H-pyran-4-yl)benzyloxy]acetyl]-4-isoxazolyl]benzenesulfonamide;

4-[4-phenyl-2-[[3-(3,4,5,6-tetrahydro-4-methoxy-2H-pyran-4-yl)phenoxy]acetyl]-1-imidazolyl]benzenesulfonamide;

5-phenyl-4-[4-(methylsulfonyl)phenyl]-2-[[3-(3,4,5,6-tetrahydro-4-methoxy-2H-pyran-4-yl)phenoxy]acetyl]imidazole;

4-[5-phenyl-2-[[3-fluoro-5-(3,4,5,6-tetrahydro-4-methoxy-2H-pyran-4-yl)phenoxy]acetyl]-4-imidazolyl]benzenesulfonamide;

4-[2-phenyl-4-[[3-(3,4,5,6-tetrahydro-4-methoxy-2H-pyran-4-yl)benzyloxy]acetyl]-1-imidazolyl]benzenesulfonamide;

4-[3-phenyl-4-[[3-(3,4,5,6-tetrahydro-4-methoxy-2H-pyran-4-yl)phenoxy]acetyl]-2-pyridyl]benzenesulfonamide;
3-phenyl-2-[4-(methylsulfonyl)phenyl]-4-[[3-(3,4,5,6-tetrahydro-4-methoxy-2H-pyran-4-yl)phenoxy]acetyl]pyridine;
4-[2-phenyl-4-[[3-fluoro-5-(3,4,5,6-tetrahydro-4-methoxy-2H-pyran-4-yl)phenoxy]acetyl]-3-pyridyl]benzenesulfonamide;
4-[2-phenyl-4-[[3-(3,4,5,6-tetrahydro-4-methoxy-2H-pyran-4-yl)benzyloxy]acetyl]-3-pyridyl]benzenesulfonamide;
4-[2-[3-(4-methoxy-3,4,5,6-tetrahydro-2H-pyran-4-yl)phenoxy]-4-phenyl-5-oxazolyl]benzenesulfonamide;
4-[2-[3-fluoro-5-(4-methoxy-3,4,5,6-tetrahydro-2H-pyran-4-yl)phenoxy]-4-phenyl-5-oxazolyl]benzenesulfonamide;
4-(4-fluorophenyl)-2-[[3-fluoro-5-(3,4,5,6-tetrahydro-4-methoxy-2H-pyran-4-yl)phenoxy)methyl]-5-(4-(methylsulfonyl)phenyl)oxazole;
4-(4-fluorophenyl)-5-(4-(methylsulfonyl)phenyl)-2-[[3-(3,4,5,6-tetrahydro-4-methoxy-2H-pyran-4-yl)phenoxy)methyl]oxazole;
4-[4-phenyl-2-[[3-(3,4,5,6-tetrahydro-4-methoxy-2H-pyran-4-yl)phenoxy]acetyl]-5-oxazolyl]benzenesulfonamide;
4-phenyl-5-[4-(methylsulfonyl)phenyl]-2-[[3-(3,4,5,6-tetrahydro-4-methoxy-2H-pyran-4-yl)phenoxy]acetyl]oxazole;
4-[4-phenyl-2-[[3-fluoro-5-(3,4,5,6-tetrahydro-4-methoxy-2H-pyran-4-yl)phenoxy]acetyl]-5-oxazolyl]benzenesulfonamide;
4-[4-phenyl-[[3-(3,4,5,6-tetrahydro-4-methoxy-2H-pyran-4-yl)benzyloxy]acetyl]-5-oxazolyl]benzenesulfonamide;
4-[4-phenyl-2-[[3-fluoro-5-(3,4,5,6-tetrahydro-4-methoxy-2H-pyran-4-yl)benzyloxy]acetyl]-5-oxazolyl]benzenesulfonamide;
4-[4-phenyl-2-[[3-(3,4,5,6-tetrahydro-4-methoxy-2H-pyran-4-yl)2-thienyloxy]acetyl]-5-oxazolyl]benzenesulfonamide;
4-[4-phenyl-2-[[5-(3,4,5,6-tetrahydro-4-methoxy-2H-pyran-4-yl)-3-pyridinyloxy]acetyl]-5-oxazolyl]benzenesulfonamide;
4-[4-phenyl-2-[[5-(3,4,5,6-tetrahydro-4-methoxy-2H-pyran-4-yl)-3-pyridylmethoxy]acetyl]-5-oxazolyl]benzenesulfonamide;
4-phenyl-2-[[6-(3,4,5,6-tetrahydro-4-methoxy-2H-pyran-4-yl)pyridin-2-ylmethoxy]acetyl]-5-oxazolyl]benzenesulfonamide;
4-phenyl-2-[[3-(2,6-dimethyl-3,4,5,6-tetrahydro-4-methoxy-2H-pyran-4-yl)benzyloxy]acetyl]-5-oxazolyl]benzenesulfonamide;
4-phenyl-2-[[2-(3,4,5,6-tetrahydro-4-methoxy-2H-pyran-4-yl)thiazol-4-ylmethoxy]acetyl]-5-oxazolyl]benzenesulfonamide;
4-phenyl-2-[[3-fluoro-5-(1S,5R 3α-methoxy-6,8-dioxabicyclo[3.2.1]octanyl)phenoxy]acetyl]-5-oxazolyl]benzenesulfonamide;
4-phenyl-2-[[3-(3,4,5,6-tetrahydro-4-hydroxy-2H-pyran-4-yl)phenoxy]acetyl]-5-oxazolyl]benzenesulfonamide;
4-phenyl-5-[4-(methylsulfonyl)phenyl]-2-[[3-(3,4,5,6-tetrahydro-4-hydroxy-2-H-pyran-4-yl-)phenoxy]acetyl]oxazole;
4-phenyl-2-[[3-fluoro-5-(3,4,5,6-tetrahydro-4-hydroxy-2H-pyran-4-yl)phenoxy]acetyl]-5-oxazolyl]benzenesulfonamide;
4-phenyl-2-[[3-(3,4,5,6-tetrahydro-4-hydroxy-2H-pyran-4-yl)benzyloxy]acetyl]-5-oxazolyl]benzenesulfonamide;

4-phenyl-2-[[3-flouro-5-(3,4,5,6-tetrahydro-4-hydroxy-2H-4-pyran-4-yl)benzyloxy]acetyl]-5-oxazolyl]benzenesulfonamide;
4-phenyl-2-[[3-(3,4,5,6-tetrahydro-4-hydroxy-2H-pyran-4-yl)thienyloxy]acetyl]-5-oxazolyl]benzenesulfonamide;
4-[4-phenyl-2-[[5-(3,4,5,6-tetrahydro-4-hydroxy-2H-pyran-4-yl)pyridin-3-yloxy]acetyl]-5-oxazolyl]benzenesulfonamide;
4-[4-phenyl-2-[[5-(3,4,5,6-tetrahydro-4-hydroxy-2H-pyran-4-yl)pyridin-3-ylmethoxy]acetyl]-5-oxazolyl]benzenesulfonamide;
4-[4-phenyl-2-[[6-(3,4,5,6-tetrahydro-4-hydroxy-2H-pyran-4-yl)pyridin-2-ylmethoxy]acetyl]-5-oxazolyl]benzenesulfonamide;
4-[4-phenyl-2-[[3-(2,6-dimethyl-3,4,5,6-tetrahydro-4-hydroxy-2H-pyran-4-yl)benzyloxy]acetyl]-5-oxazolyl]benzenesulfonamide;
4-[4-phenyl-2-[[2-(3,4,5,6-tetrahydro-4-hydroxy-2H-pyran-4-yl)thiazol-4-ylmethoxy]acetyl]-5-oxazolyl]benzenesulfonamide;
4-[4-phenyl-2-[[3-fluoro-5-(1S,5R 3α-hydroxy-6,8-dioxabicyclo[3.2.1]octanyl)phenoxy]acetyl]-5-oxazolyl]benzenesulfonamide;
4-[4-phenyl-2-[2-[3-(3,4,5,6-tetrahydro-4-methoxy-2-H-pyran-4-yl)phenoxy](E-oximinomethyl)ethyl]-5-oxazolyl]benzenesulfonamide;
4-[4-phenyl-2-[2-[3-(3,4,5,6-tetrahydro-4-methoxy-2H-pyran-4-yl)phenoxy](Z-oximinomethyl)ethyl]-5-oxazolyl]benzenesulfonamide;
4-[4-phenyl-2-[2-[3-(3,4,5,6-tetrahydro-4-4-methoxy-2H-pyran-4-yl)phenoxy](E-oximino)ethyl]-5-oxazolyl]benzenesulfonamide;
4-[4-phenyl-2-[2-[3-(3,4,5,6-tetrahydro-4-methoxy-2H-pyran-4-yl)phenoxy](Z-oximino)ethyl]-5-oxazolyl]benzenesulfonamide;
4-phenyl-5-[4-[4-(methylsulfonyl)phenyl]-2-[2-3-(3,4,5,6-tetrahydro-4-methoxy-2H-pyran-4-yl)phenoxy](E-oximinomethyl)ethyl]oxazole;
4-phenyl-5-[4-[4-(methylsulfonyl)phenyl]-2-[2-[3-(3,4,5,6-tetrahydro-4-methoxy-2H-pyran-4-yl)phenoxy](Z-oximinomethyl)ethyl]oxazole;
4-[4-phenyl-2-[2-[3-fluoro-5-(3,4,5,6-tetrahydro-4-methoxy-2H-pyran-4-yl)phenoxy](E-oximino)ethyl]-5-oxazolyl]benzenesulfonamide;
4-[4-phenyl-2-[2-[3-fluoro-5-(3,4,5,6-tetrahydro-4-methoxy-2H-pyran-4-yl)phenoxy](Z-oximino)ethyl]-5-oxazolyl]benzenesulfonamide;
4-[4-phenyl-2-[2-[3-(3,4,5,6-tetrahydro-4-methoxy-2H-pyran-4-yl)benzyloxy](E-oximino)ethyl]-5-oxazolyl]benzenesulfonamide;
4-[4-phenyl-2-[2-[3-(3,4,5,6-tetrahydro-4-methoxy-2H-pyran-4-yl)benzyloxy](Z-oximino)ethyl]-5-oxazolyl]benzenesulfonamide;
4-[4-phenyl-2-[2-[3-fluoro-5-(3,4,5,6-tetrahydro-4-methoxy-2H-pyran-4-yl)benzyloxy](E-oximino)ethyl]-5-oxazolyl]benzenesulfonamide;
4-[4-phenyl-2-[2-[3-fluoro-5-(3,4,5,6-tetrahydro-4-methoxy-2H-pyran-4-yl)benzyloxy](Z-oximino)ethyl]-5-oxazolyl]benzenesulfonamide;
4-[4-phenyl-2-[2-[3-(3,4,5,6-tetrahydro-4-methoxy-2H-pyran-4-yl)thienyloxy](E-oximino)ethyl]-5-oxazolyl]benzenesulfonamide;
4-[4-phenyl-2-[2-[3-(3,4,5,6-tetrahydro-4-methoxy-2H-pyran-4-yl)thienyloxy](Z-oximino)ethyl]-5-oxazolyl]benzenesulfonamide;

4-[4-phenyl-2-[2-[5-(3,4,5,6-tetrahydro-4-methoxy-2H-pyran-4-yl)pyridin-3-yloxy](E-oximino)ethyl]-5-oxazolyl]benzenesulfonamide;
4-[4-phenyl-2-[2-[5-(3,4,5,6-tetrahydro-4-methoxy-2H-pyran-4-yl)pyridin-3-yloxy](Z-oximino)ethyl]-5-oxazolyl]benzenesulfonamide;
4-[4-phenyl-2-[2-[5-(3,4,5,6-tetrahydro-4-methoxy-2H-pyran-4-yl)pyridin-3-ylmethoxy](E-oximino)ethyl]-5-oxazolyl]benzenesulfonamide;
4-[4-phenyl-2-[2-[5-(3,4,5,6-tetrahydro-4-methoxy-2H-pyran-4-yl)pyridin-3-ylmethoxy](Z-oximino)ethyl]-5-oxazolyl]benzenesulfonamide;
4-[4-phenyl-2-[2-[6-(3,4,5,6-tetrahydro-4-methoxy-2H-pyran-4-yl)pyridin-2-ylmethoxy](E-oximino)ethyl]-5-oxazolyl]benzenesulfonamide;
4-[4-phenyl-2-[2-[6-(3,4,5,6-tetrahydro-4-methoxy-2H-pyran-4-yl)pyridin-2-ylmethoxy](Z-oximino)ethyl]-5-oxazolyl]benzenesulfonamide;
4-[4-phenyl-2-[2-[3-(2,6-dimethyl-3,4,5,6-tetrahydro-4-methoxy-2H-pyran-4-yl)benzyloxy](E-oximino)ethyl]-5-oxazolyl]benzenesulfonamide;
4-[4-phenyl-2-[2-[3-(2,6-dimethyl-3,4,5,6-tetrahydro-4-methoxy-2H-pyran-4-yl)benzyloxy](Z-oximino)ethyl]-5-oxazolyl]benzenesulfonamide;
4-[4-phenyl-2-[2-[2-(3,4,5,6-tetrahydro-4-methoxy-2H-pyran-4-yl)thiazol-4-ylmethoxy](E-oximino)ethyl]-5-oxazolyl]benzenesulfonamide;
4-[4-phenyl-2-[2-[2-(3,4,5,6-tetrahydro-4-methoxy-2H-pyran-4-yl)thiazol-4-ylmethoxy](Z-oximino)ethyl]-5-oxazolyl]benzenesulfonamide;
4-[4-phenyl-2-[2-[3-fluoro-5-(1S,5R3α-methoxy-6,8-dioxabicyclo[3.2.1]octanyl)phenoxy](Z-oximino)ethyl]-5-oxazolyl]benzenesulfonamide;
4-[4-phenyl-2-[2-[3-fluoro-5-(1S,5R 3α-methoxy-6,8-dioxabicyclo[3.2.1]octanyl)phenoxy](E-oximino)ethyl]-5-oxazolyl]benzenesulfonamide;
4-[4-phenyl-2-[3-[3-(3,4,5,6-tetrahydro-4-methoxy-2H-pyran-4-yl)phenoxy]propyn-1-yl]-5-oxazolyl]benzenesulfonamide;
4-phenyl-5-[4-[4-(methylsufonyl)phenyl]-2-[3-[3-(3,4,5,6-tetrahydro-4-methoxy-2H-pyran-4-yl)phenoxy]propyn-1-yl]oxazole;
4-[4-phenyl-2-[3-[3-fluoro-5-(3,4,5,6-tetrahydro-4-methoxy-2H-pyran-4-yl)phenoxy]propyn-1-yl]-5-oxazolyl]benzenesulfonamide;
4-[4-phenyl-2-[3-[3-(3,4,5,6-tetrahydro-4-methoxy-2H-pyran-4-yl)benzyloxy]propyn-1-yl]-5-oxazolyl]benzenesulfonamide;
4-[4-phenyl-2-[3-[3-fluoro-5-(3,4,5,6-tetrahydro-4-methoxy-2H-pyran-4-yl)benzyloxy]propyn-1-yl]-5-oxazolyl]benzenesulfonamide;
4-[4-phenyl-2-[3-[3-(3,4,5,6-tetrahydro-4-methoxy-2H-pyran-4-yl)-thienyloxy]propyn-1-yl]-5-oxazolyl]benzenesulfonamide;
4-[4-phenyl-2-[3-[5-(3,4,5,6-tetrahydro-4-methoxy-2H-pyran-4-yl)pyridin-3-yloxy]propyn-1-yl]-5-oxazolyl]benzenesulfonamide;
4-[4-phenyl-2-[3-[5-(3,4,5,6-tetrahydro-4-methoxy-2H-pyran-4-yl)pyridin-3-ylmethoxy]propyn-1-yl]-5-oxazolyl]benzenesulfonamide;
4-[4-phenyl-2-[3-[6-(3,4,5,6-tetrahydro-4-methoxy-2H-pyran-4-yl)pyridin-2-ylmethoxy]propyn-1-yl]-5-oxazolyl]benzenesulfonamide;
4-[4-phenyl-2-[3-[3-(2,6-dimethyl-3,4,5,6-tetrahydro-4-methoxy-2H-pyran-4-yl)benzyloxy]propyn-1-yl]-5-oxazolyl]benzenesulfonamide;
4-[4-phenyl-2-[3-[2-(3,4,5,6-tetrahydro-4-methoxy-2H-pyran-4-yl)thiazol-4-ylmethoxy]propyn-1-yl]-5-oxazolyl]benzenesulfonamide;
4-[4-phenyl-2-[3-[3-fluoro-5-(1S,5R 3α-methoxy-6,8-dioxabicyclo[3.2.1]octanyl)phenoxy]propyn-1-yl]-5-oxazolyl]benzenesulfonamide;
4-[4-phenyl-2-[3-[3-(3,4,5,6tetrahydro-4-hydroxy-2H-pyran-4-yl)phenoxy]propyn-1-yl]-5-oxazolyl]benzenesulfonamide;
4-phenyl-5-[4-[4-(methylsulfonyl)phenyl]-2-[3-[3-(3,4,5,6-tetrahydro-4-hydroxy-2H-pyran-4-yl)phenoxy]propyn-1-yl]oxazole;
4-[4-phenyl-2-[3-[3-fluoro-5-(3,4,5,6-tetrahydro-4-hydroxy-2H-pyran-4-yl)phenoxy]propyn-1-yl]-5-oxazolyl]benzenesulfonamide;
4-[4-phenyl-2-[3-[3-(3,4,5,6-tetrahydro-4-hydroxy-2H-pyran-4-yl)benzyloxy]propyn-1-yl]-5-oxazolyl]benzenesulfonamide;
4-[4-phenyl-2-[3-[3-3-fluoro-5-(3,4,5,6-tetrahydro-4-hydroxy-2H-pyran-4-yl)benzyloxy]propyn-1-yl]-5-oxazolyl]benzenesulfonamide;
4-[4-phenyl-2-[3-[3-(3,4,5,6-tetrahydro-4-hydroxy-2H-pyran-4-yl)thienyloxy]propyn-1-yl]-5-oxazolyl]benzenesulfonamide;
4-[4-phenyl-2-[3-[5-(3,4,5,6-tetrahydro-4-hydroxy-2H-pyran-4-yl)pyridin-3-yloxy]propyn-1-yl]-5-oxazolyl]benzenesulfonamide;
4-[4-phenyl-2-[3-[5-(3,4,5,6-tetrahydro-4-hydroxy-2H-pyran-4-yl)pyridin-3-ylmethoxy]propyn-1-yl]-5-oxazolyl]benzenesulfonamide;
4-[4-phenyl-2-[3-[6-(3,4,5,6-tetrahydro-4-hydroxy-2H-pyran-4-yl)pyridin-2-ylmethoxy]propyn-1-yl]-5-oxazolyl]benzenesulfonamide;
4-[4-phenyl-2-[3-[3-(2,6-dimethyl-3,4,5,6-tetrahydro-4-hydroxy-2H-pyran-4-yl)benzyloxy]propyn-1-yl]-5-oxazolyl]benzenesulfonamide;
4-[4-phenyl-2-[3-[2-(3,4,5,6-tetrahydro-4-hydroxy-2H-pyran-4-yl)thiazol-4-ylmethoxy]propyn-1-yl]-5-oxazolyl]benzenesulfonamide;
4-[4-phenyl-2-[3-[3-fluoro-5-(1S,5R 3α-hydroxy-6,8-dioxabicyclo[3.2.1]octanyl)phenoxy]propyn-1-yl]-5-oxazolyl]benzenesulfonamide;
4-[4-phenyl-2-[3-[3-(3,4,5,6-tetrahydro-4-methoxy-2H-pyran-4-yl)phenoxy]propyl]-5-oxazolyl]benzenesulfonamide;
4-phenyl-5-[4-[4-(methylsulfonyl)phenyl]-2-[3-[3-(3,4,5,6-tetrahydro-4-methoxy-2H-pyran-4-yl)phenoxy]propyl]oxazole;
4-[4-phenyl-2-[3-[3-fluoro-5-(3,4,5,6-tetrahydro-4-methoxy-2H-pyran-4-yl)phenoxy]propyl]-5-oxazolyl]benzenesulfonamide;
4-[4-phenyl-2-[3-[3-(3,4,5,6-tetrahydro-4-methoxy-2H-pyran-4-yl)benzyloxy]propyl]-5-oxazolyl]benzenesulfonamide;
4-[4-phenyl-2-[3-[3-flouro-5-(3,4,5,6-tetrahydro-4-methoxy-2H-pyran-4-yl)benzyloxy]propyl]-5-oxazolyl]benzenesulfonamide;
4-[4-2-[3-[3-(3,4,5,6-tetrahydro-4-methoxy-2H-pyran-4-yl)-2-thienyloxy]propyl]-5-oxazolyl]benzenesulfonamide;
4-[4-phenyl-2-[3-[5-(3,4,5,6-tetrahydro-4-methoxy-2H-pyran-4-yl)pyridin-3-yloxy]propyl]-5-oxazolyl]benzenesulfonamide;
4-[4-phenyl-2-[3-[5-(3,4,5,6-tetrahydro-4-methoxy-2H-pyran-4-yl)pyridin-3-ylmethoxy]propyl]-5-oxazolyl]benzenesulfonamide;

4-[4-phenyl-2-[3-[4-(3,4,5,6-tetrahydro-4-methoxy-2H-pyran-4-yl)pyridin-2-ylmethoxy]propyn]-5-oxazolyl]benzenesulfonamide;

4-[4-phenyl-2-[3-[3-(2,6-dimethyl-3,4,5,6-tetrahydro-4-methoxy-2H-pyran-4-yl)benzyloxy]propyl]-5-oxazolyl]benzenesulfonamide;

4-[4-phenyl-2-[3-[2-(3,4,5,6-tetrahydro-4-methoxy-2H-pyran-4-yl)thiazol-4-ylmethoxy]propyl]-5-oxazolyl]benzenesulfonamide;

4-[4-phenyl-2-[3-[3-fluoro-5-(1S,5R 3α-methoxy-6,8-dioxabicyclo[3.2.1]octanyl)phenyl]propyl]-5-oxazolyl]benzenesulfonamide;

4-[4-phenyl-2-[3-[3-(3,4,5,6-tetrahydro-4-hydroxy-2H-pyran-4yl)phenoxy]propyl]-5-oxazolyl]benzenesulfonamide;

4-[4-phenyl-5-[4-[4-(methylsulfonyl)phenyl]-2-[3-[3-(3,4,5,6-tetrahydro-4-hydroxy-2H-pyran-4-yl)phenoxy]propyl]-5-oxazole;

4-[4-phenyl-2-[3-[3-flouro-5-(3,4,5,6-tetrahydro-4-hydroxy-2H-pyran-4-yl)phenoxy]propyl]-5-oxazolyl]benzenesulfonamide;

4-[4-phenyl-2-[3-[3-(3,4,5,6-tetrahydro-4-hydroxy-2H-pyran-4-yl)benzyloxy]propyl]-5-oxazolyl]benzenesulfonamide;

4-[4-phenyl-2-[3-[3-flouro-5-(3,4,5,6-tetrahydro-4-hydroxy-2H-pyran-4-yl)benzyloxy]propyl]-5-oxazolyl]benzenesulfonamide;

4-[4-phenyl-2-[3-[3-(3,4,5,6-tetrahydro-4-hydroxy-2H-pyran-4-yl)-2-thienyloxy]propyl]-5-oxazolyl]benzenesulfonamide;

4-[4-phenyl-2-[3-[5-(3,4,5,6-tetrahydro-4-hydroxy-2H-pyran-4-yl)pyridin-3-yloxy]propyl]-5-oxazolyl]benzenesulfonamide;

4-[4-phenyl-2-[3-[5-(3,4,5,6-tetrahydro-4-hydroxy-2H-pyran-4-yl)pyridin-3-ylmethoxy]propyl]-5-oxazolyl]benzenesulfonamide;

4-[4-phenyl-2-[3-[6-(3,4,5,6-tetrahydro-4-hydroxy-2H-pyran-4-yl)pyridin-2-ylmethoxy]propyl]-5-oxazolyl]benzenesulfonamide;

4-[4-phenyl-2-[3-[3-(2,6-dimethyl-3,4,5,6-tetrahydro-4-hydroxy-2H-pyran-4-yl)benzyloxy]propyl]-5-oxazolyl]benzenesulfonamide;

4-[4-phenyl-2-[3-[2-(3,4,5,6-tetrahydro-4-hydroxy-2H-pyran-4-yl)thiazol-4-ylmethoxy]propyl]-5-oxazolyl]benzenesulfonamide;

4-[4-phenyl-2-[3-[3-fluoro-5-(1S,5R 3α-hydroxy-6,8-dioxabicyclo[3.2.1]octanyl)phenoxy]propyl]-5-oxazolyl]benzenesulfonamide;

4-[4-phenyl-2-[2-[3-(3,4,5,6-tetrahydro-4-methoxy-2H-pyran-4-yl)phenoxy]ethyl]-5-oxazolyl]benzenesulfonamide;

4-[4-phenyl-5-[4-[4-(methylsulfonyl)phenyl]-2-[2-[3-(3,4,5,6-tetrahydro-4-methoxy-2H-pyran-4-yl)phenoxy]ethyl]oxazole;

4-[4-phenyl-2-[2-[3-fluoro-5-(3,4,5,6-tetrahydro-4-methoxy-2H-pyran-4-yl)phenoxy]ethyl]-5-oxazolyl]benzenesulfonamide;

4-[4-phenyl-2-[2-[3-(3,4,5,6-tetrahydro-4-methoxy-2H-pyran-4-yl)benzyloxy]ethyl]-5-oxazolyl]benzenesulfonamide;

4-[4-phenyl-2-[2-[3-fluoro-5-(3,4,5,6-tetrahydro-4-methoxy-2H-pyran-4yl)benzyloxy]ethyl]-5-oxazolyl]benzenesulfonamide;

4-[4-phenyl-2-[2-[3-(3,4,5,6-tetrahydro-4-methoxy-2H-pyran-4-yl)-5-thienyloxy]ethyl]-5-oxazolyl]benzenesulfonamide;

4-[4-phenyl-2-[2-[5-(3,4,5,6-tetrahydro-4-methoxy-2H-pyran-4-yl)pyridin-3-yloxy]ethyl]-5-oxazolyl]benzenesulfonamide;

4-[4-phenyl-2-[2-[5-(3,4,5,6-tetrahydro-4-methoxy-2H-pyran-4-yl)pyridin-3-ylmethoxy]ethyl]-5-oxazolyl]benzenesulfonamide;

4-[4-phenyl-2-[2-[6-(3,4,5,6-tetrahydro-4-methoxy-2H-pyran-4-yl)pyridin-2-ylmethoxy]ethyl]-5-oxazolyl]benzenesulfonamide;

4-[4-phenyl-2-[2-[3-(2,6-dimethyl-3,4,5,6-tetrahydro-4-methoxy-2H-pyran-4-yl)benzyloxy]ethyl]-5-oxazolyl]benzenesulfonamide;

4-[4-phenyl-2-[2-[2-(3,4,5,6-tetrahydro-4-methoxy-2H-pyran-4-yl)thiazol-4-ylmethoxy]ethyl]-5-oxazolyl]benzenesulfonamide;

4-[4-phenyl-2-[2-[3-fluoro-5-(1R,5S 3α-methoxy-6,8-dioxabicyclo[3.2.1]octanyl)phenoxy]ethyl]-5-oxazolyl]benzenesulfonamide;

4-[4-phenyl-2-[2-[3-(3,4,5,6-tetrahydro-4-hydroxy-2H-pyran-4-y)phenoxy]ethyl]-5-oxazolyl]benzenesulfonamide;

4-phenyl-5-[4-[4-(methylsulfonyl)phenyl]-2-[2-[3-(3,4,5,6-tetrahydro-4-hydroxy-2H-pyran-4-yl)phenoxy]ethyl]oxazole;

4-[4-phenyl-2-[2-[3-fluoro-5-(3,4,5,6-tetrahydro-4-hydroxy-2H-pyran-4-yl)phenoxy]ethyl]-5-oxazolyl benzenesulfonamide;

4-[4-phenyl-2-[2-[3-(3,4,5,6-tetrahydro-4-hydroxy-2H-pyran-4-yl)benzyloxy]ethyl]-5-oxazolyl]benzenesulfonamide;

4-[4-phenyl-2-[2-[3-flouro-(3,4,5,6-tetrahydro-4-hydroxy-2H-pyran-4-yl)benzyloxy]ethyl]-5-oxazolyl]benzenesulfonamide;

4-[4-phenyl-2-[2-[3-(3,4,5,6-tetrahydro-4-hydroxy-2H-pyran-4-yl)-5-thienyloxy]ethyl]-5-oxazolyl]benzenesulfonamide;

4-[4-phenyl-2-[2-[5-(3,4,5,6-tetrahydro-4-hydroxy-2H-pyran-4-yl)pyridin-3-yloxy]ethyl]-5-oxazolyl]benzenesulfonamide;

4-[4-phenyl-2-[2-[5-(3,4,5,6-tetrahydro-4-hydroxy-2H-pyran-4-yl)pyridin-3-ylmethoxy]ethyl]-5-oxazolyl]benzenesulfonamide;

4-[4-phenyl-2-[2-[6-(3,4,5,6-tetrahydro-4-hydroxy-2H-pyran-4-yl)pyridin-2-ylmethoxy]ethyl]-5-oxazolyl]benzenesulfonamide;

4-[4-phenyl-2-[2-[3-(2,6-dimethyl-3,4,5,6-tetrahydro-4-hydroxy-2H-pyran-4-yl)benzyloxy]ethyl]-5-oxazolyl]benzenesulfonamide;

4-[4-phenyl-2-[2-[2-(3,4,5,6-tetrahydro-4-hydroxy-2H-pyran-4-yl)thiazol-4-ylmethoxy]ethyl]-5-oxazolyl]benzenesulfonamide;

4-[4-phenyl-2-[2-[3-fluoro-5-(1S,5R 3α-hydroxy-6,8-dioxabicyclo[3.2.1]octanyl)phenoxy]ethyl]-5-oxazolyl]benzenesulfonamide;

4-[4-phenyl-2-[1-hydroxy-2-[3-(3,4,5,6-tetrahydro-4-methoxy-2H-pyran-4-yl)phenoxy]ethyl]-5-oxazolyl]benzenesulfonamide;

4-phenyl-5-[4-[4-(methylsulfonyl)phenyl]-2-[1-hydroxy-2-[3-(3,4,5,6-tetrahydro-4-methoxy-2H-pyran-4-yl)phenoxy]ethyl]oxazole;

4-[4-phenyl-2-[1-hydroxy-2-[3-fluoro-5-(3,4,5,6-tetrahydro-4-methoxy-2H-pyran-4yl)phenoxy]ethyl]-5-oxazolyl]benzenesulfonamide;

4-[4-phenyl-2-[1-hydroxy-2-[3-(3,4,5,6-tetrahydro-4-methoxy-2H-pyran-4-yl)benzyloxy]ethyl]-5-oxazolyl]benzenesulfonamide;

4-[4-phenyl-2-[1-hydroxy-2-[3-fluoro-5-(3,4,5,6-tetrahydro-4-methoxy-2H-pyran-4-yl)benzyloxy]ethyl]-5-oxazolyl]benzenesulfonamide;

4-[4-phenyl-2-[1-hydroxy-2-[3-(3,4,5,6-tetrahydro-4-methoxy-2H-pyran-4-yl)thiophenyl]ethyl]-5-oxazolyl]benzenesulfonamide;

4-[4-phenyl-2-[1-hydroxy-2-[5-(3,4,5,6-tetrahydro-4-methoxy-2H-pyran-4-yl)pyridin-3-yloxy]ethyl]-5-oxazolyl]benzenesulfonamide;

4-[4-phenyl-2-[1-hydroxy-2-[5-(3,4,5,6-tetrahydro-4-methoxy-2H-pyran-4-yl)pyridin-3-ylmethoxy]ethyl]-5-oxazolyl]benzenesulfonamide;

4-[4-phenyl-2-[1-hydroxy-2-[6-(3,4,5,6-tetrahydro-4-methoxy-2H-pyran-4-yl)pyridin-2-ylmethoxy]ethyl]-5-oxazolyl]benzenesulfonamide;

4-[4-phenyl-2-[1-hydroxy-2-[3-(2,6-dimethyl-3,4,5,6-tetrahydro-4-methoxy-2H-pyran-4-yl)benzyloxy]ethyl]-5-oxazolyl]benzenesulfonamide;

4-[4-phenyl-2-[1-hydroxy-2-[2-(3,4,5,6-tetrahydro-4-methoxy-2H-pyran-4-yl)thiazol-4-ylmethoxy]ethyl]-5-oxazolyl]benzenesulfonamide;

4-[4-phenyl-2-[1-hydroxy-2-[3-fluoro-5-(1S,5R 3α-methoxy-6,8-dioxabicyclo[3.2.1]octanyl)phenoxy]ethyl]-5-oxazolyl]benzenesulfonamide;

4-[4-phenyl-2-[1-hydroxy-2-[3-(3,4,5,6-tetrahydro-4-hydroxy-2-H-pyran-4-yl)phenoxy]ethyl]-5-oxazolyl]benzenesulfonamide;

4-phenyl-5-[4-[4-(methylsulfonyl)phenyl]-2-[1-hydroxy-2-[3-(3,4,5,6-tetrahydro-4-hydroxy-2H-pyran-4-yl)phenoxy]ethyl]oxazole;

4-[4-phenyl-2-[1-hydroxy-2-[3-flouro-5-(3,4,5,6-tetrahydro-4-hydroxy-2H-pyran-4-yl)phenoxy]ethyl]-5-oxazolyl]benzenesulfonamide;

4-[4-phenyl-2-[1-hydroxy-2-3-(3,4,5,6-tetrahydro-4-hydroxy-2H-pyran-4-yl)benzyloxy]ethyl]-5-oxazolyl]benzenesulfonamide;

4-[4-phenyl-2-[1-hydroxy-2-[3-fluoro-5-(3,4,5,6-tetrahydro-4-hydroxy-2H-pyran-4-yl)benzyloxy]ethyl]-5-oxazolyl]benzenesulfonamide;

4-[4-phenyl-2-[1-hydroxy-2-[3-(3,4,5,6-tetrahydro-4-hydroxy-2H-pyran-4-yl)thiophenyl]ethyl]-5-oxazolyl]benzenesulfonamide;

4-[4-phenyl-2-[1-hydroxy-2-[5-(3,4,5,6-tetrahydro-4-hydroxy-2H-pyran-4-yl)pyridin-3-yloxy]ethyl]-5-oxazolyl]benzenesulfonamide;

4-[4-phenyl-2-[1-hydroxy-2-[5-(3,4,5,6-tetrahydro-4-hydroxy-2H-pyran-4-yl)pyridin-3-ylmethoxy]ethyl]-5-oxazolyl]benzenesulfonamide;

4-[4-phenyl-2-[1-hydroxy-2-[6-(3,4,5,6-tetrahydro-4-hydroxy-2H-pyran-4-yl)pyridin-2-ylmethoxy]ethyl]-5-oxazolyl]benzenesulfonamide;

4-[4-phenyl-2-[1-hydroxy-2-[3-(2,6-dimethyl-3,4,5,6-tetrahydro-4-hydroxy-2H-pyran-4-yl)benzyloxy]ethyl]-5-oxazolyl]benzenesulfonamide;

4-[4-phenyl-2-[1-hydroxy-2-[2-(3,4,5,6-tetrahydro-4-hydroxy-2-pyran-4-yl)thiazol-4-ylmethoxy]ethyl]-5-oxazolyl]benzenesulfonamide;

4-[4-phenyl-2-[1-hydroxy-2-[3-fluoro-5-(1S,5R 3α-hydroxy-6,8-dioxabicyclo[3.2.1]octanyl)phenoxy]ethyl]-5-oxazolyl]benzenesulfonamide;

4-[4-phenyl-2-[[3-(3,4,5,6-tetrahydro-4-methoxy-2H-pyran-4-yl)phenoxy]methyl]-5-oxazolyl]benzenesulfonamide;

4-phenyl-5-[4-[4-(methylsulfonyl)phenyl]-2-[[3-(3,4,5,6-tetrahydro-4-methoxy-2H-pyran-4-yl)phenoxy]methyl]oxazole;

4-[4-phenyl-2-[[3-flouro-5-(3,4,5,6-tetrahydro-4-methoxy-2H-pyran-4-yl)phenoxy]methyl]-5-oxazolyl]benzenesulfonamide;

4-[4-phenyl-2-[[3-(3,4,5,6-tetrahydro-4-methoxy-2H-pyran-4-yl)benzyloxy]methyl]-5-oxazolyl]benzenesulfonamide;

4-[4-phenyl-2-[[3-fluoro-5-(3,4,5,6-tetrahydro-4-methoxy-2H-pyran-4-yl)benzyloxy]methyl]-5-oxazolyl]benzenesulfonamide;

4-[4-phenyl-2-[[3-(3,4,5,6-tetrahydro-4-methoxy-2H-pyran-4-yl)thiophenyl]methyl]-5-oxazolyl]benzenesulfonamide;

4-[4-phenyl-2-[[5-(3,4,5,6-tetrahydro-4-methoxy-2H-pyran-4-yl)pyridin-3-yloxy]methyl]-5-oxazolyl]benzenesulfonamide;

4-[4-phenyl-2-[[5-(3,4,5,6-tetrahydro-4-methoxy-2H-pyran-4-yl)pyridin-3-ylmethoxy]methyl]-5-oxazolyl]benzenesulfonamide;

4-[4-phenyl-2-[[6-(3,4,5,6-tetrahydro-4-methoxy-2H-pyran-4-yl)pyridin-2-ylmethoxy]methyl]-5-oxazolyl]benzenesulfonamide;

4-[4-phenyl-2-[[3-(2,6-dimethyl-3,4,5,6-tetrahydro-4-methoxy-2H-pyran-4-yl)benzyloxy]methyl]-5-oxazolyl]benzenesulfonamide;

4-[4-phenyl-2-[[2-(3,4,5,6-tetrahydro-4-methoxy-2H-pyran-4-yl)thiazol-4-ylmethoxy]methyl]-5-oxazolyl]benzenesulfonamide;

4-[4-phenyl-2-[[3-fluoro-5-(1S,5R 3α-methoxy-6,8-dioxabicyclo[3.2.1]octanyl)phenoxy]methyl]-5-oxazolyl]benzenesulfonamide;

4-[4-phenyl-2-[[3-(3,4,5,6-tetrahydro-4-hydroxy-2H-pyran-4-yl)phenoxy]methyl]-5-oxazolyl]benzenesulfonamide;

4-phenyl-5-[4-[4-(methylsulfonyl)phenyl]-2-[[3-(3,4,5,6-tetrahydro-4-hydroxy-2H-pyran-4-yl)phenoxy]methyl]oxazole;

4-[4-phenyl-2-[[3-fluoro-5-(3,4,5,6-tetrahydro-4-hydroxy-2H-pyran-4-yl)phenoxy]methyl]-5-oxazolyl]benzenesulfonamide;

4-[4-phenyl-2-[[3-(3,4,5,6-tetrahydro-4-hydroxy-2H-pyran-4-yl)benzyloxy]methyl]-5-oxazolyl]benzenesulfonamide;

4-[4-phenyl-2-[[3-fluoro-5-(3,4,5,6-tetrahydro-4-hydroxy-2H-pyran-4-yl)benzyloxy]methyl]-5-oxazolyl]benzenesulfonamide;

4-[4-phenyl-2-[[3-(3,4,5,6-tetrahydro-4-hydroxy-2H-pyran-4-yl)thiophenyl]methyl]-5-oxazolyl]benzenesulfonamide;

4-[4-phenyl-2[-[5-(3,4,5,6-tetrahydro-4-hydroxy-2H-pyran-4-yl)pyridin-3-yloxy]methyl]-5-oxazolyl]benzenesulfonamide;

4-[4-phenyl-2-[[5-(3,4,5,6-tetrahydro-4-hydroxy-2H-pyran-4-yl)pyridin-3-ylmethoxy]methyl]-5-oxazolyl]benzenesulfonamide;

4-[4-phenyl-2-[[6-(3,4,5,6-tetrahydro-4-hydroxy-2H-pyran-4-yl)pyridin-2-ylmethoxy]methyl]-5-oxazolyl]benzenesulfonamide;

4-[4-phenyl-2-[[3-(2,6-dimethyl-3,4,5,6-tetrahydro-4-hydroxy-2H-pyran-4-yl)benzyloxy]methyl]-5-oxazolyl]benzenesulfonamide;

4-[4-phenyl-2-[[2-(3,4,5,6-tetrahydro-4-hydroxy-2H-pyran-4-yl)thiazol-4-ylmethoxy]methyl]-5-oxazolyl]benzenesulfonamide;

4-[4-phenyl-2-[[3-fluoro-5-(1S,5R 3α-hydroxy-6,8-dioxabicyclo[3.2.1-]octanyl)phenoxy]methyl]-5-oxazolyl]benzenesulfonamide; 4-[4-phenyl-2-[3-[3-(3,4,5,6-tetrahydro-4-methoxy-2H-pyran-4-yl)phenoxy](E-propen)-1-yl]-5-oxazolyl]benzenesulfonamide;

4-phenyl-5-[4-[4-(methylsulfonyl)phenyl]-2-[3-[3-(3,4,5,6-tetrahydro-4-methoxy-2H-pyran-4-yl)phenoxy](E & Z-propen)-1-yl]oxazole;

4-[4-phenyl-2-[3-[3-fluoro-5-(3,4,5,6-tetrahydro-4-methoxy-2H-pyran-4-yl)phenoxy](Z-propen)-1-yl]-5-oxazolyl]benzenesulfonamide;

4-[4-phenyl-2-[3-[3-(3,4,5,6-tetrahydro-4-methoxy-2H-pyran-4-yl)benzyloxy](Z-propen)-1-yl]-5-oxazolyl]benzenesulfonamide;

4-[4-phenyl-2-[3-[3-fluoro-5-(3,4,5,6-tetrahydro-4-methoxy-2H-pyran-4-yl)benzyloxy](Z-propen)-1-yl]-5-oxazolyl]benzenesulfonamide;

4-[4-phenyl-2-[3-[3-(3,4,5,6-tetrahydro-4-methoxy-2H-pyran-4-yl)thiophenyl](E-propen)-1-yl-5-oxazolyl]benzenesulfonamide;

4-[4-phenyl-2-[3-[5-(3,4,5,6-tetrahydro-4-methoxy-2H-pyran-4-yl)pyridin-3-yloxy](Z-propen)-1-yl]-5-oxazolyl]benzenesulfonamide;

4-[4-phenyl-2-[3-[5-(3,4,5,6-tetrahydro-4-methoxy-2H-pyran-4-yl)pyridin-3-ylmethoxy](E-propen)-1-yl]-5-oxazolyl]benzenesulfonamide;

4-[4-phenyl-2-[3-[6-(3,4,5,6-tetrahydro-4-methoxy-2H-pyran-4-yl)pyridin-2-ylmethoxy](Z-propen)-1-yl]-5-oxazolyl[benzenesulfonamide;

4-[4-phenyl-2-[3-[3-(2,6-dimethyl-3,4,5,6-tetrahydro-4-methoxy-2H-pyran-4-yl)benzyloxy](Z-propen)-1-yl]-5-oxazolyl]benzenesulfonamide;

4-[4-phenyl-2-[3-[2-(3,4,5,6-tetrahydro-4-methoxy-2-pyran-4-yl)thiazol-4-ylmethoxy](Z-propen)-1-yl]-5-oxazolyl]benzenesulfonamide;

4-[4-phenyl-2-[3-[3-fluoro-5-(1S,5R 3α-methoxy-6,8-dioxabicyclo[3.2.1]octanyl)phenoxy](Z-propen)-1-yl]-5-oxazolyl]benzenesulfonamide;

4-[4-phenyl-2-[3-[3-(3,4,5,6-tetrahydro-4-hydroxy-2H-pyran-4-yl)phenoxy](E-propen)-1-yl]-5-oxazolyl]benzenesulfonamide;

4-phenyl-5-[4-[4-(methylsulfonyl)phenyl]-2-[3-[3-(3,4,5,6-tetrahydro-4-hydroxy-2H-pyran-4-yl)phenoxy](E-propen)-1-yl]oxazole;

4-[4-phenyl-2-[3-[3-fluoro-5-(3,4,5,6-tetrahydro-4-hydroxy-2H-pyran-4-yl)phenoxy](Z-propen)-yl-1-5-oxazolyl]benzenesulfonamide;

4-[4-phenyl-2-[3-[3-(3,4,5,6-tetrahydro-4-hydroxy-2H-pyran-4-yl)benzyloxy](E-propen)-1-yl]-5-oxazolyl]benzenesulfonamide;

4-[4-phenyl-2-[3-[3-fluoro-5-(3,4,5,6-tetrahydro-4-hydroxy-2H-pyran-4-yl)benzyloxy](Z-propen)-1-yl]-5-oxazolyl]benzenesulfonamide;

4-[4-phenyl-2-[3-[3-(3,4,5,6-tetrahydro-4-hydroxy-2H-pyran-4-yl)thiophenyl](Z-propen)-1-yl]-5-oxazolyl]benzenesulfonamide;

4-[4-phenyl-2-[3-[5-(3,4,5,6-tetrahydro-4-hydroxy-2H-pyran-4-yl)pyridin-3-yloxy](Z-propen)-1-yl]-5-oxazolyl]benzenesulfonamide;

4-[4-phenyl-2-[3-[5-(3,4,5,6-tetrahydro-4-hydroxy-2H-pyran-4-yl)pyridin-3-ylmethoxy](Z-propen)-1-yl]-5-oxazolyl]benzenesulfonamide;

4-[4-phenyl-2-[3-[6-(3,4,5,6-tetrahydro-4-hydroxy-2H-pyran-4-yl)pyridin-2-ylmethoxy](E-propen)-1-yl]-5-oxazolyl]benzenesulfonamide;

4-[4-phenyl-2-[3-[3-(2,6-dimethyl-3,4,5,6-tetrahydro-4-hydroxy-2H-pyran-4-yl)benzyloxy](E-propen)-1-yl]-5-oxazolyl]benzenesulfonamide;

4-[4-phenyl-2-[3-[2-(3,4,5,6-tetrahydro-4-hydroxy-2H-pyran-4-yl)thiazol-4-ylmethoxy](Z-propen)-1-yl]-5-oxazolyl]benzenesulfonamide;

4-[4-phenyl-2-[3-[3-fluoro-5-(1S,5R 3α-hydroxy-6,8-dioxabicyclo[3.2.1]octanyl)phenoxy](E-propen)-1-yl]-5-oxazolyl]benzenesulfonamide;

4-[4-phenyl-2-[[3-(3,4,5,6-tetrahydro-4-methoxy-2H-pyran-4-yl)phenoxy]-1,2,3-triazol-4-ylmethyl-5-]-5-oxazolyl]benzenesulfonamide;

4-[4-phenyl-5-[4-[4-(methylsulfonyl)phenyl]-2-[[3-(3,4,5,6-tetrahydro-4-methoxy-2H-pyran-4-yl)phenoxy)-1,2,3-triazol-4-ylmethyl-5-]-5-oxazolyl]benzenesulfonamide;

4-[4-phenyl-2-[[3-fluoro-5-(3,4,5,6-tetrahydro-4-methoxy-2H-pyran-4-yl)phenoxy]-1,2,3-triazol-4-methoxy-2H-pyran-4-yl)phenoxy]-1,2,3-triazol-4-ylmethyl-5-]-5-oxazolyl]benzenesulfonamide;

4-[4-phenyl-2-[3-(3,4,5,6-tetrahydro-4-methoxy-2H-pyran-4-yl)benzyloxy-1,2,3-triazol]-4-ylmethyl-5-]-5-oxazolyl]benzenesulfonamide;

4-[4-phenyl-2-[[3-fluoro-5-(3,4,5,6-tetrahydro-4-methoxy-2H-pyran-4-yl)benzyloxy]-1,2,3-triazol-4-ylmethyl-5-]-5-oxazolyl]benzenesulfonamide;

4-[4-phenyl-2-[[3-(3,4,5,6-tetrahydro-4-methoxy-2H-pyran-4-yl)thiophenyl]-1,2,3-triazol-4-ylmethyl-5-]-5-oxazolyl]benzenesulfonamide;

4-[4-phenyl-2-[[5-(3,4,5,6-tetrahydro-4-methoxy-2H-pyran-4-yl)pyridin-3-yloxy]-1,2,3-triazol-4-ylmethyl-5-]-5-oxazolyl]benzenesulfonamide;

4-[4-phenyl-2-[[5-(3,4,5,6-tetrahydro-4-methoxy-2H-pyran-4-yl)pyridin-3-ylmethoxy]-1,2,3-triazol-4-ylmethyl-5-]-5-oxazolyl]benzenesulfonamide;

4-[4-phenyl-2-[[6-(3,4,5,6-tetrahydro-4-methoxy-2H-pyran-4-yl)pyridin-2-ylmethoxy]-1,2,3-triazol-4-ylmethyl-5-]-5-oxazolyl]benzenesulfonamide;

4-[4-phenyl-2-[-[3-(2,6-dimethyl-3,4,5,6-tetrahydro-4-methoxy-2H-pyran-4-yl)benzyloxy]-1,2,3-triazol-4-ylmethyl-5-]-5-oxazolyl]benzenesulfonamide;

4-[4-phenyl-2-[[2-(3,4,5,6-tetrahydro-4-methoxy-2H-pyran-4-yl)thiazol-4-ylmethoxy]-1,2,3-triazol-4-ylmethyl-5-]-5-oxazolyl]benzenesulfonamide;

4-[4-phenyl-2-[[3-fluoro-5-(1S,5R 3α-methoxy-6,8-dioxabicyclo[3.2.1]octanyl)phenoxy]-1,2,3-triazol-4-ylmethyl-5-]-5-oxazolyl]benzenesulfonamide;

4-[4-phenyl-2-[[3-(3,4,5,6-tetrahydro-4-hydroxy-2H-pyran-4-yl)phenoxy]-1,2,3-triazol-4-ylmethyl-5-]-5-oxazolyl]benzenesulfonamide;

4-phenyl-5-[4-[4-(methylsulfonyl)phenyl]-2-[[3-(3,4,5,6-tetrahydro-4-hydroxy-2H-pyran-4-yl)phenoxy]-1,2,3-triazol-4-ylmethyl-5-]oxazole;

4-[4-phenyl-2-[[3-fluoro-5-(3,4,5,6-tetrahydro-4-hydroxy-2H-pyran-4-yl)phenoxy]-1,2,3-triazol-4-ylmethyl-5-]-5-oxazolyl]benzenesulfonamide;

4-[4-phenyl-2-[[3-(3,4,5,6-tetrahydro-4-hydroxy-2H-pyran-4-yl)benzyloxy]-1,2,3-triazol-4-ylmethyl-5-]-5-oxazolyl[benzenesulfonamide;

4-[4-phenyl-2-[[3-fluoro-5-(3,4,5,6-tetrahydro-4-hydroxy-2H-pyran-4-yl)benzyloxy]-1,2,3-triazol-4-ylmethyl-5-]-5-oxazolyl]benzenesulfonamide;

4-[4-phenyl-2-[[3-(3,4,5,6-tetrahydro-4-hydroxy-2H-pyran-4-yl)thiophenyl]-1,2,3-triazol-4-ylmethyl-5-]-5-oxazolyl]benzenesulfonamide;

4-[4-phenyl-2-[[5-(3,4,5,6-tetrahydro-4-hydroxy-2H-pyran-4-yl)pyridin-3-yloxy]-1,2,3-triazol-4-ylmethyl-5-]-5-oxazolyl]benzenesulfonamide;

4-[4-phenyl-2-[[5-(3,4,5,6-tetrahydro-4-hydroxy-2H-pyran-4-yl)pyridin-3-ylmethoxy]-1,2,3-triazol-4-ylmethyl-5-]-5-oxazolyl]benzenesulfonamide;

4-[4-phenyl-2-[[6-(3,4,5,6-tetrahydro-4-hydroxy-2H-pyran-4-yl)pyridin-2-ylmethoxy]-1,2,3-triazol-4-ylmethyl-5-]-5-oxazolyl]benzenesulfonamide;

4-[4-phenyl-2-[[3-(2,6-dimethyl-3,4,5,6-tetrahydro-4-hydroxy-2H-pyran-4-yl)benzyloxy]-1,2,3-triazol-4-ylmethoxy-5-]-5-oxazolyl]benzenesulfonamide;

4-[4-phenyl-2-[[2-(3,4,5,6-tetrahydro-4-hydroxy-2H-pyran-4-yl)thiazol-4-ylmethoxy]-1,2,3-triazol-4-ylmethyl-5-]-5-oxazolyl]benzenesulfonamide;

4-[4-phenyl-2-[[3-fluoro-5-(1S,5R 3α-hydroxy-6,8-dioxabicyclo[3.2.1]octanyl)phenoxy]-1,2,3-triazol-4-ylmethyl-5-]-5-oxazolyl]benzenesulfonamide;

4-[4-phenyl-2-[[3-(3,4,5,-tetrahydro-2H-pyran-4-yl)]E-oximinomethyl]phenoxy]acetyl]-5-oxazolyl]benzenesulfonamide;

4-[4-methyl-2-[[[3-(3,4,5,6-tetrahydro-2H-pyran-4-yl)]Z-oximinomethyl]phenoxy]acetyl]-5-oxazolyl]benzenesulfonamide;

4-[4-phenyl-2-[[E-O-methyl-[3-(3,4,5,6-tetrahydro-2H-pyran-4-yl)]oximinomethyl]phenoxy]acetyl]-5-oxazolyl]benzenesulfonamide;

4-[4-phenyl-2-[[Z-O-methyl-[3-(3,4,5,6-tetrahydro-2H-pyran-4-yl)oximinomethyl]phenoxy]acetyl]-5-oxazolyl]benzenesulfonamide;

4-[4-phenyl-2-[3-[[3-(3,4,5,6-tetrahydro-2H-pyran-4-yl)]Z-oximinomethyl]phenoxy]propyn-1-yl]-5-oxazolyl]benzenesulfonamide;

4-[4-phenyl-2-[3-[[3-(3,4,5,6-tetrahydro-2H-pyran-4-yl)]E-oximinomethyl]phenoxy]propyn-1-yl]-5-oxazolyl]benzenesulfonamide;

4-[4-phenyl-2-[3-[E-O-methyl-[3-(3,4,5,6-tetrahydro-2H-pyran-4-yl)]oximinomethyl]phenoxy]propyn-1-yl]-5-oxazolyl]benzenesulfonamide;

4-[4-phenyl-2-[3-[Z-O-methyl-[3-(3,4,5,6-tetrahydro-2H-pyran-4-yl)]oximinomethyl]phenoxy]propyn-1-yl]-5-oxazolyl]benzenesulfonamide;

4-[4-phenyl-2-[3-[3-(3,4,5,6-tetrahydro-4-methoxy-2H-pyran-4-yl)phenyl]propyn-1-yl]-5-oxazolyl]benzenesulfonamide;

4-phenyl-5-[4-[4-(methylsulfonyl)phenyl]-2-[3-[3-(3,4,5,-tetrahydro-4-methoxy-2H-pyran-4-yl)phenyl]propyn-1-yl]oxazole;

4-[4-phenyl-2-[3-[3-fluoro-5-(3,4,5,6-tetrahydro-4-methoxy-2H-pyran-4-yl)phenyl]propyn-1-yl]-5-oxazolyl]benzenesulfonamide;

4-[4-phenyl-2-[3-[5-(3,4,5,6-tetrahydro-4-methoxy-2H-pyran-4-yl)pyridin-3-yl]propyn-1-yl]-5-oxazolyl]benzenesulfonamide;

4-[4-phenyl-2-[3-[3-(2,6-dimethyl-3,4,5,6-tetrahydro-4-methoxy-2H-pyran-4-yl)phenyl]propyn-1-yl]-5-oxazolyl]benzenesulfonamide;

4-[4-phenyl-2-[3-[2-(3,4,5,6-tetrahydro-4-methoxy-2H-pyran-4yl)thiazol-4-yl]propyn-1-yl]-5-oxazolyl]benzenesulfonamide;

4-[4-phenyl-2-[3-[3-flouro-5-(1S,5R 3α-methoxy-6,8-dioxabicyclo[3.3.1]octanyl)phenyl]propyn-1-yl]-5-oxazolyl]benzenesulfonamide;

4-[4-phenyl-2-[3-[3-(3,4,5,6-tetrahydro-4-hydroxy-2H-pyran-4-yl)phenyl]propyn-1-yl]-5-oxazolyl]benzenesulfonamide;

4-phenyl-5-[4-[4-(methylsulfonyl)phenyl]-2-[3-[3-(3,4,5,6-tetrahydro-4-hydroxy-2H-pyran-4-yl)phenyl]propyn-1-yl]oxazole;

4-[4-phenyl-2-[3-[3-fluoro-5-(3,4,5,6-tetrahydro-4-hydroxy-2H-pyran-4-yl)phenyl]propyn-1-yl]-5-oxazolyl]benzenesulfonamide;

4-[4-phenyl-2-[3-[5-(3,4,5,6-tetrahydro-4-hydroxy-2H-pyran-4-yl)pyridin-3-y]propyn-1-yl]-5-oxazolyl]benzenesulfonamide;

4-[4-phenyl-2-[3-[3-(2,6-dimethyl-3,4,5,6-tetrahydro-4-hydroxy-2H-pyran-4-yl)phenyl]propyn-1-yl]-5-oxazolyl]benzenesulfonamide;

4-[4-phenyl-2-[3-[2-(3,4,5,6-tetrahydro-4-hydroxy-2H-pyran-4-yl)thiazol-4-yl]propyn-1-yl]-5-oxazolyl]benzenesulfonamide;

4-[4-phenyl-2-[3-[3-fluoro-5-(1S,5R 3α-hydroxy-6,8-dioxabicyclo[3.2.1]octanyl)phenyl]propyn-1-yl]-5-oxazolyl]benzenesulfonamide;

4-[4-phenyl-2-[3-[3-(3,4,5,6-tetrahydro-4-methoxy-2H-pyran-4-4-yl)phenyl]propyl]-5-oxazolyl]benzenesulfonamide;

4-phenyl-5-[4-[4-(methylsulfonyl)phenyl]-2-[3-[3-(3,4,5,6-tetrahydro-4-methoxy-2H-pyran-4-yl)phenyl]propyl]oxazole;

4-[4-phenyl-2-[3-[3-fluoro-5-(3,4,5,6-tetrahydro-4-methoxy-2H-pyran-4-yl)phenyl]propyl]y-5-oxazolyl]benzenesulfonamide;

4-[4-phenyl-2-[3-[5-(3,4,5,6-tetrahydro-4-methoxy-2H-pyran-4-yl)pyridin-3-yl]propyl]-5-oxazolyl]benzenesulfonamide;

4-[4-phenyl-2-[3-[3-(2,6-dimethyl-3,4,5,6-tetrahydro-4-methoxy-2H-pyran-4-yl)phenyl]propyl]-5-oxazolyl]benzenesulfonamide;

4-[4-phenyl-2-[3-[2-(3,4,5,6-tetrahydro-4-methoxy-2H-pyran-4-yl)thiazol-4-yl]propyl]-5-oxazolyl]benzenesulfonamide;

4-[4-phenyl-2-[3-[3-fluoro-5-(1S,5R 3α-methoxy-6,8-dioxabicyclo[3.2.1]octanyl)phenyl]propyl]-5-oxazolyl]benzenesulfonamide;

4-[4-phenyl-2-[3-[3-(3,4,5,6-tetrahydro-4-hydroxy-2H-pyran-4-yl)phenyl]propyl]-5-oxazolyl]benzenesulfonamide;

4-phenyl-5-[4-[4-(methylsulfonyl)phenyl]-2-[3-[3-(3,4,5,6-tetrahydro-4-hydroxy-2H-pyran-4-yl)phenyl]propyl]oxazole;

4-[4-phenyl-2-[3-[3-fluoro-5-(3,4,5,6-tetrahydro-4-hydroxy-2H-pyran-4-yl)phenyl]propyl]-5-oxazolyl]benzenesulfonamide;

4-[4-phenyl-2-[3-[5-(3,4,5,6-tetrahydro-4-hydroxy-2H-pyran-4-yl)pyridin-3-yl]propyl]-5-oxazolyl]benzenesulfonamide;

4-[4-phenyl-2-[3-[3-(2,6-dimethyl-3,4,5,6-tetrahydro-4-hydroxy-2H-pyran-4-yl)phenyl]propyl]-5-oxazolyl]benzenesulfonamide;

4-[4-phenyl-2-[3-[2-(3,4,5,6-tetrahydro-4-hydroxy-2H-pyran-4-yl)thiazol-4-yl]propyl]-5-oxazolyl]benzenesulfonamide; and 4-[4-phenyl-2-[3-[3-fluoro-5-(1S,5R 3α-hydroxy-6,8-dioxabicyclo[3.2.1]octanyl)phenyl]propyn-1-yl]-5-oxazolyl]benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—CH₂—) radical. Where used, either alone or within ocher terms such as "haloalkyl", "alkylsulfonyl", "alkoxyalkyl" and "hydroxyalkyl", the term "alkyl" embraces linear or branched radicals having one to about twenty carbon atoms or, preferably, one to about towel carbon atoms. More preferred alkyl radicals are "lower alkyl" radicals having one to about ten carbon atoms. Most preferred are lower alkyl radicals having one to about six carbon atoms. Example of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms. More preferred alkyl radicals are "lower alkenyl" radicals having two to about six carbon atoms. Examples of alkenyl radicals include ethenyl, propenyl, alkenyl, propenyl, butenyl and 4-methylbutenyl. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. alkynyl radicals of such radicals include propargyl, butynyl, and the like. The terms "alkenyl", "lower alkenyl", embrace radicals having "cis" and "trans" orientations, or alternatively, "E" and "Z" orientations. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term. "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxpropyl, hydroxybutyl and hydroxyhexyl. The term "cyanoalkyl" embraces linear or branched alkyl radicals having one to about ten carbon atoms any one of which may be substituted with one or more cyano radicals. More preferred cyanoalkyl radicals are "lower cyanoalkyl" radicals having one to six carbon atoms and one or more cyano radicals. Examples of such radicals include cyanomethyl, cyanoethyl, cyanopropyl, cyanobutyl and cyanohexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals, or with hydroxyl radicals to from "hydroxyalkyloxy" radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. More preferred hydroxyalkyloxy radicals are "lower hydroxyalkyloxy" radicals having alkyl portions of 1 to 6 carbons. The term "alkenyloxy" embraces radicals having alkenyl portions of two to about ten carbon atoms attached to an oxygen atom. More preferred alkenyloxy radicals are "lower alkenyloxy" radicals having two to six carbon atoms. The term "alkynyloxy" embraces radicals having alkynyl portions of two to about ten carbon atoms attached to an oxygen atom. More preferred alkynyloxy radicals are "lower alkynyloxy" radicals having two to six carbon atoms. Examples of such lower alkynyloxy radicals include propynyloxy, and butynyloxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclyl" embraces saturated, partially unsaturated and unsaturated heteroatom-containing ring-shaped radicals, where the heteroatoms may be selected from nitrogen, sulfur and oxygen. Examples of saturated heterocyclyl radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. The term "heteroaryl" embraces unsaturated heterocyclyl radicals. Examples of unsaturated heterocyclyl radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term also embraces radicals where heterocyclyl radicals are fused with aryl radicals. Examples of such fused bicyclic radicals include benzofuran, benzothiophene, and the like.

Said "heterocyclyl group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "oximinoalkoxy" embraces alkyloxy radicals having one to about ten carbon atoms any one or which may be substituted with one or more oximino radicals (—C=NOH). More preferred oximinoalkoxy radicals are "lower oximinoalkoxy" radicals having alkoxy radicals containing one to six carbon atoms. Examples of such radicals include oximinomethoxy, oximinopropoxy, and oximinobutoxy. The term "oximinoalkoxyalkyl" embraces alkyloxyalkyl radicals with alkyl and portions having one to about ten carbon atoms any one of which may be substituted with an oximino radical (—C=NOH). More preferred oximinoalkoxyalkyl radicals are "lower oximinoalkoxyalkyl" radicals having alkyl radicals containing one to six carbon atoms. The terms "(alkyl)oximinoalkoxyalkyl" and "(alkyl)oximinoalkoxy" embrace oximinoalkoxyalkyl and oximinoalkoxy radicals, as defined above, where the oximino portion is substituted on the oxygen atom with alkyl radicals having one to about ten carbon atoms. More preferred oximinoalkoxyalkyl radicals are "lower "(alkyl)oximinoalkoxyalkyl" and "lower (alkyl)oximinoalkoxy" radicals having alkyl radicals containing one to six carbon atoms. The term "alkenylthio" embraces radicals containing a linear or branched alkenyl radical, of two to about ten carbon atoms attached to a divalent sulfur atom. More preferred alkenylthio radicals are "lower alkenylthio" radicals having alkenyl radicals of two to six carbon atoms. The term "alkynylthio" embraces radicals containing a linear or branched alkynyl radical, of two to about ten carbon atoms attached to a divalent sulfur atom. More preferred alkynylthio radicals are "lower alkynylthio" radicals having alkynyl radicals of two to six carbon atoms. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote NH$_2$O$_2$S—. The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl. The term "carbonyl", whether used alone or with other terms, such as "alkoxycarbonyl", denotes —(C=O)—. The term "aroyl" embraces aryl radicals with a carbonyl radical as defined above. Examples of aroyl include benzoyl, naphthoyl, and the like and the aryl in said aroyl may be additionally substituted. The terms "carboxy" or "carboxyl", whether used alone or with other terms, such as "carboxyalkyl", denotes —CO$_2$H. The term "carboxyalkyl" embraces alkyl radicals substituted with a carboxy radical. More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl portions having 1 to 6 carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined above, to a carbonyl radical. Examples of such radicals include substituted or unsubstituted methylcarbonyl, ethylcarbonyl, phenylcarbonyl and benzylcarbonyl. The term "aralkyl" embraces arylsubstituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heteroaralkyl" embraces heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "aralkoxy" embraces aralkyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "heteroaralkoxy" embraces heteroaralkyl radicals attached through an oxygen atom to other radicals. The term "heteroaralkylthio" embraces heteroaralkyl radicals attached through a sulfur atom to other radicals. The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which have been substituted with one or two alkyl radicals. Preferred are "lower N-alkylamino" radicals having alkyl portions having 1 to 6 carbon atoms. Suitable lower alkylamino may be mono or dialkylamino such as N-methylamino, N-ethylamino, N,N-dimethylamino, N,N-diethylamino or the like. The term "cycloalkylamino" denotes amino groups which have been substituted with one or two cycloalkyl radicals, as defined above. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an nitrogen atom to other radicals. The terms "N-arylaminoalkyl" and "N-aryl-N-alkyl-aminoalkyl" denote amino groups which have been substituted with one aryl radical or one aryl and one alkyl radical, respectively, and having the amino group attached to an alkyl radical. Examples of such radicals include N-phenylaminomethyl and N-phenyl-N-methylaminomethyl. The term "aminocarbonyl" denotes an amide group of the formula —C(=O)NH$_2$. The term "alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined above. The term "alkylaminocarbonylhaloalkyl" denotes an aminocarbonyl group which has been substituted with one or two alkyl radicals on the amino nitrogen atom, attached to an haloalkyl radical. Preferred are "N-alkylaminocarbonylhaloalkyl" "N,N-alkylaminocarbonylhaloalkyl" radicals. More preferred are "lower N-alkylaminocarbonylhaloalkyl" "lower N,N-alkylaminocarbonylhaloalkyl" radicals with lower alkyl and lower haloalkyl portions as defined above. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom.

When the above radicals are included as linker moiety "Y" in Formulas I–II, such radicals are divalent radicals. In addition, the orientation of the radicals between "A" and "Ar" are reversible. For example, the term "alkylthio" represents both —CH$_2$S— and —SCH$_2$—, and "carbonylmethyloxy" represents both —C(O)CH$_2$O— and —OCH$_2$C(O)—. For terms such as aralkyl, and heteroarylalkyl, the moiety may be linked to "A" and "Ar" through a divalent alkyl radical, or through the alkyl radical at one end and the aryl or heteroaryl portion at the other. The use of heterocyclyl and aryl moieties includes divalent attachment at substitutable sites. The use of a substituted amine group, does not include attachment through a divalent nitrogen atom (i.e., —N(CH$_3$)—) but instead (—N(H)CH$_2$—).

The present invention comprises a pharmaceutical composition comprising a therapeutically-effective amount of a compound of Formulas I–II in association with at least one pharmaceutically-acceptable carrier, adjuvant or diluent.

The present invention also comprises a method of treating inflammation or inflammation-associated disorders in a subject, the method comprising treating the subject having or susceptible to such inflammation or disorder, with a therapeutically-effective amount of a compound of Formulas I–II. The method includes prophylactic or chronic treatment, especially in the case of arthritis and other inflammatory conditions which can lead to deterioration in the joints.

Also included in the family of compounds of Formula I are the stereoisomers and tautomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula I with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a calt.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclyl, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I–XXIII, wherein the R$^1$–R$^9$ substituents are as defined for Formula I–II, above, except where further noted.

Scheme I

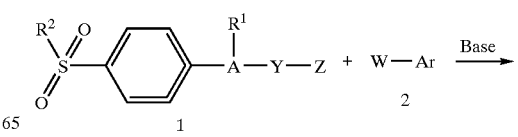

-continued

Synthetic Scheme I shows the preparation of sulfonylphenyl derivatives 3, where one of Z or W is a leaving group. A substituted aromatic or heteroaryl 2, such a tetrahydropyran substituted aryl, and a base such as anhydrous potassium carbonate are dissolved in anhydrous solvent such as DMF. A solution of sulfonylphenyl derivative 1 in anhydrous DMF is added and stirred at room temperature to provide the sulfonylphenyl derivatives 3.

Scheme II

Synthetic Scheme II shows the preparation or pyrazole compounds embraced by Formula I where R is Ar or Z (as defined in Scheme I), and $R^a$ is a radical defined above for the substituents optionally substituted on A. In step 1, ketone 4 is treated with a base, preferably NaOMe or NaH, and an ester, or ester equivalent, to form the intermediate diketone 5 (in the enol form) which is used without further purification. In step 2, diketone 5 in an anhydrous protic solvent, such as absolute ethanol or acetic acid, is treated with the hydrochloride salt or the free base of a substituted hydrazine at reflux to afford a mixture of pyrazoles 6 and 7. Recrystallization from diethyl ether/hexane or chromatography affords 6 usually as a solid. Similar pyrazoles can be prepared by methods described in U.S. Pat. Nos. 4,146,721, 5,051,518, 5,134,142 and 4,914,121 which are incorporated by reference.

Scheme III

Scheme III shows the four step procedure for forming pyrazoles 11 of the present invention (where $R^b$ is alkyl) from ketones 8. In step 1, ketone 8 is reacted with a base, such as lithium bis(trimethylsilyl)amide or lithium diisopropylamide (LDA) to form the anion. In step 2, the anion is reacted with an acetylating reagent to provide diketone 9. In step 3, the reaction of diketone 9 with hydrazine or a substituted hydrazine, gives pyrazole 10. In step 4, the pyrazole 10 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 11 and the 5-(alkylsulfonyl)phenyl-pyrazole isomer. The desired pyrazole 11, usually a white or pale yellow solid, is obtained in pure form either by chromatography or recrystallization.

Alternatively, diketone 9 can be formed from ketone 8 by treatment with a base, such as sodium hydride, in a solvent, such as dimethylformamide, and further reacting with a nitrile to form an aminoketone. Treatment of the aminoketone with acid forms the diketone 9. Similar pyrazoles can be prepared by methods described in U.S. Pat. No. 3,984,431 which is incorporated by reference.

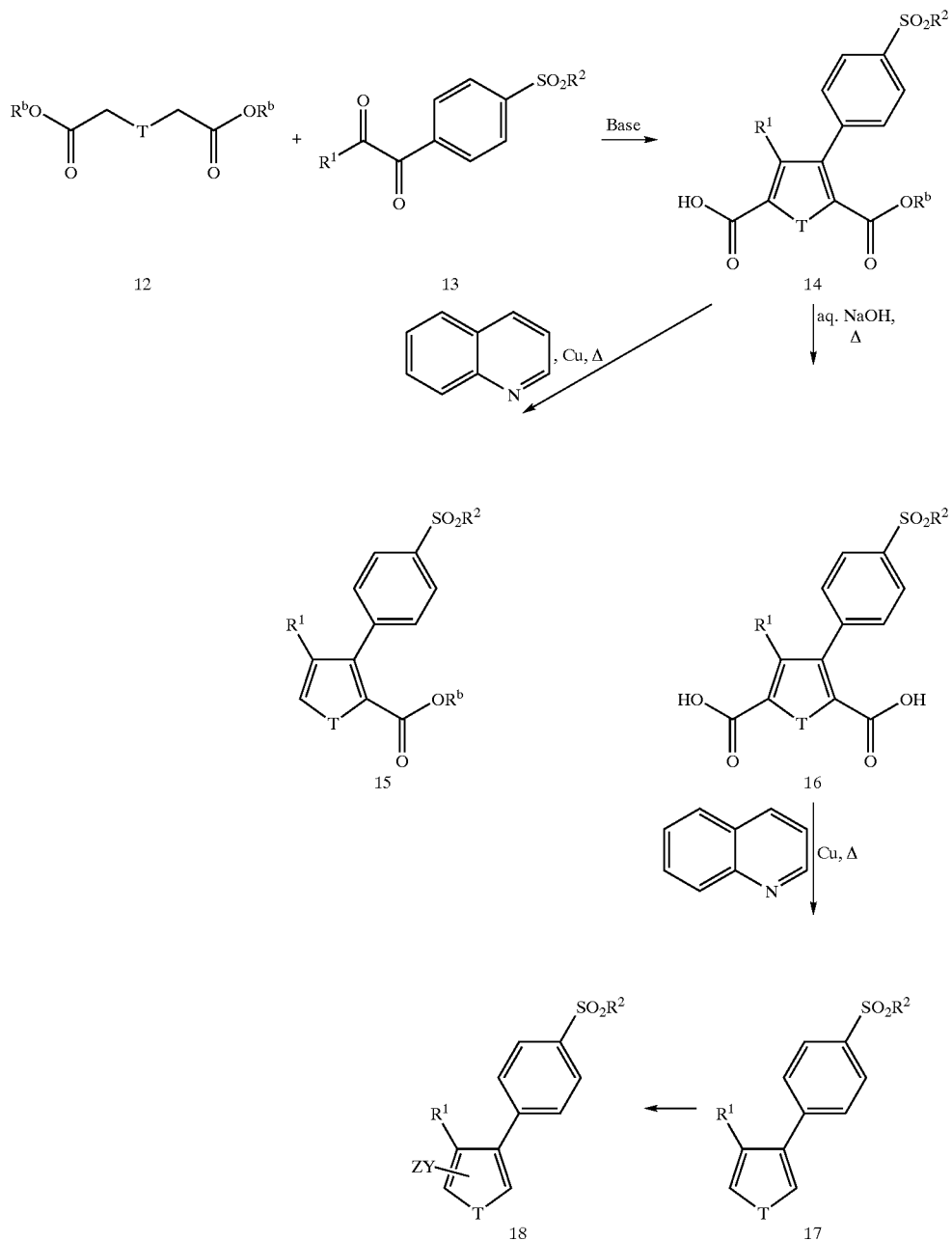

Scheme IV

Diaryl/heteroaryl thiophenes (where T is S, and R^b is alkyl) can be prepared by the methods described in U.S. Pat. Nos. 4,427,693, 4,302,461, 4,381,311, 4,590,205, and 4,820,827, and PCT documents WO 95/00501 and WO94/15932, which are incorporated by reference. Similar pyrroles (where T is N), furanones and furans (where T is O) can be prepared by methods described in PCT documents WO 95/00501 and WO94/15932.

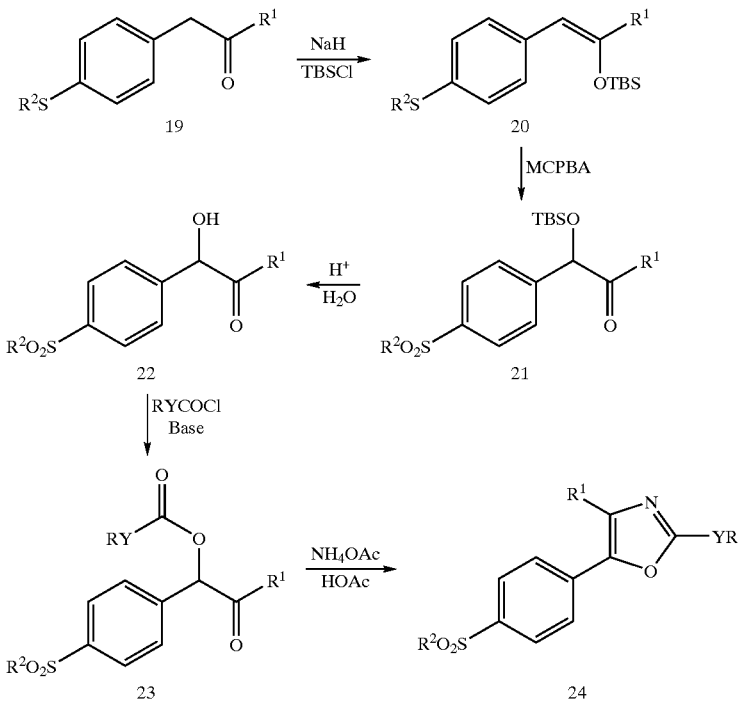

Scheme V

Diaryl/heteroaryl oxazoles can be prepared by the methods described in U.S. Pat. Nos. 3,743,656, 3,644,499 and 3,647,850, and PCT documents WO 95/00501 and WO94/15932, which are incorporated by reference.

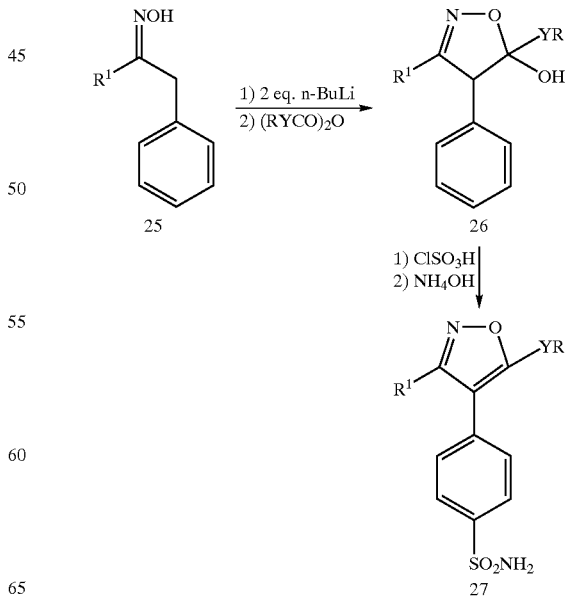

Scheme VI

Diaryl/heteroaryl isoxazoles can be prepared by the methods described in PCT documents WO92/05162, and WO92/19604, and European Publication EP 26928 which are incorporated by reference. Sulfonamides 27 can be formed from the hydrated isoxazole 26 in a two step procedure. First, hydrated isoxazole 26 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 27.

Scheme VII

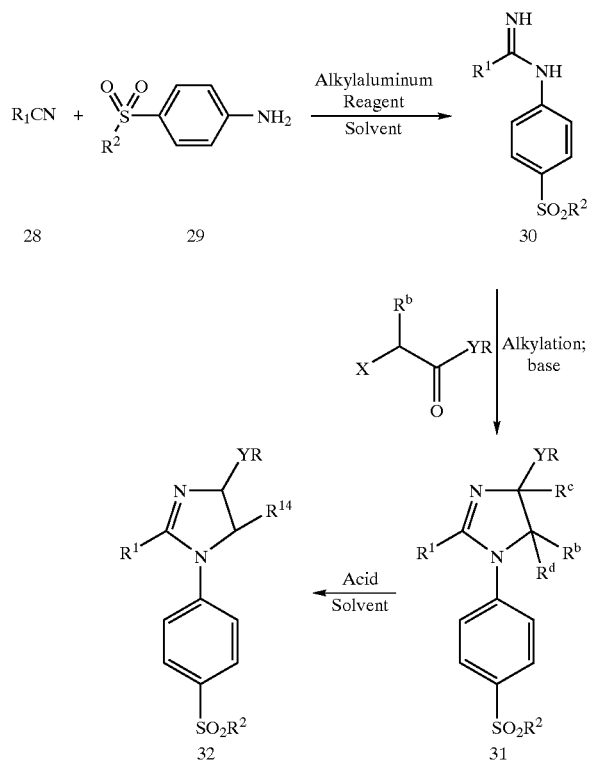

Scheme VII shows the three step preparation of the substituted imidazoles 32 of the present invention. In step 1, the reaction of substituted nitriles ($R^1CN$) 28 with primary phenylamines 29 in the presence of alkylaluminum reagents such as trimethylaluminum, triethylaluminum, dimethylaluminum chloride, diethylaluminum chloride in the presence of inert solvents such as toluene, benzene, and xylene, gives amidines 30. In step 2, the reaction of amidine 30 with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 31 (where $R^b$ is alkyl, $R^c$ is hydroxyl and $R^d$ is hydrido). Some of the suitable solvents for this reaction are isopropanol, acetone and dimethylformamide. The reaction may be carried out at temperatures of about 20° C. to about 90° C. In step 3, the 4,5-dihydroimidazoles 31 may be dehydrated in the presence of an acid catalyst such as 4-toluenesulfonic acid or mineral acids to form the 1,2-disubstituted imidazoles 32 of the invention. Suitable solvents for this dehydration step are e.g., toluene, xylene and benzene. Trifluoroacetic acid can be used as solvent and catalyst for this dehydration step.

In some cases (e.g., where YR=methyl or phenyl) the intermediate 31 may not be readily isolable. The reaction, under the conditions described above, proceeds to give the targeted imidazoles directly.

Similarly, imidazoles can be prepared having the sulfonylphenyl moiety attached at position 2 and $R^1$ attached at the nitrogen atom at position 1. Diaryl/heteroaryl imidazoles can be prepared by the methods described in U.S. Pat. Nos. 4,822,805, and PCT document WO 93/14082, which are incorporated by reference.

Scheme VIII

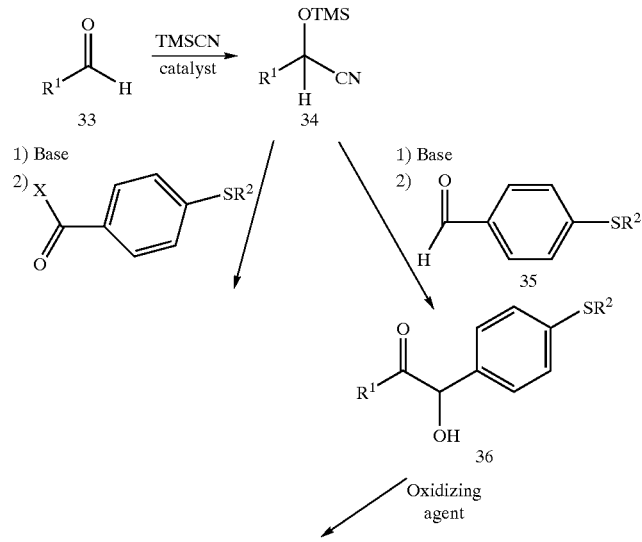

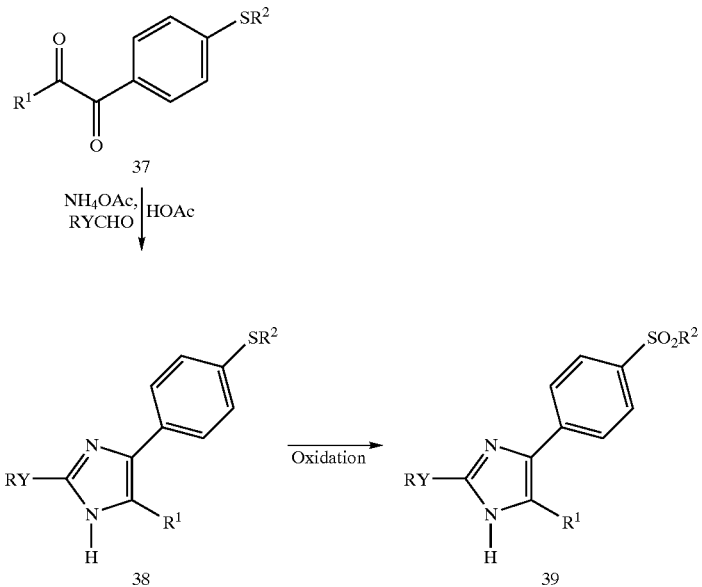

The subject imidazole compounds 39 of this invention may be synthesized according to the sequence outlined in Scheme VIII. Aldehyde 33 may be converted to the protected cyanohydrin 34 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 34 with a strong base followed by treatment with benzaldehyde 35 (where $R^2$ is alkyl) and using both acid and base treatments, in that order, on workup gives benzoin 36. Examples of strong bases suitable for this reaction are lithium diisopropylamide (LDA) and lithium hexamethyldisilazane. Benzoin 36 may be converted to benzil 37 by reaction with a suitable oxidizing agent, such as bismuth oxide or manganese dioxide, or by a Swern oxidation using dimethyl sulfoxide (DMSO) and trifluoroacetic anhydride. Benzil 37 may be obtained directly by reaction of the anion of cyanohydrin 34 with a substituted benzoic acid halide. Any of compounds 36 and 37 may be used as intermediates for conversion to imidazoles 38 (where $R^2$ is alkyl) according to chemical procedures known by those skilled in the art and described by M. R. Grimmett, "Advances in Imidazole Chemistry" in Advances in Heterocyclic Chemistry, 12, 104 (1970). The conversion of 37 to imidazoles 38 is carried out by reaction with ammonium acetate and an appropriate aldehyde (RYCHO) in acetic acid. Benzoin 36 may be converted to imidazoles 38 by reaction with formamide. In addition, benzoin 36 may be converted to imidazoles by first acylating with an appropriate acyl group (RYCO—) and then treating with ammonium hydroxide. Those skilled in the art will recognize that the oxidation of the sulfide (where $R^2$ is methyl) to the sulfone may be carried out at any point along the way beginning with compounds 35, and including oxidation of imidazoles 38, using, for examples, reagents such as hydrogen peroxide in acetic acid, m-chloroperoxybenzoic acid (MCPBA) and potassium peroxymonosulfate (OXONE®).

Diaryl/heteroaryl imidazoles can be prepared by the methods described in U.S. Pat. Nos. 3,707,475, 4,686,231, 4,503,065, 4,472,422, 4,372,964, 4,576,958, 3,901,908, European publication EP 372,445, and PCT document WO 95/00501, which are incorporated by reference.

Scheme IX

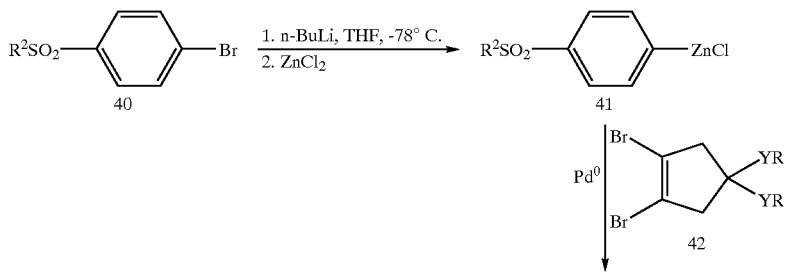

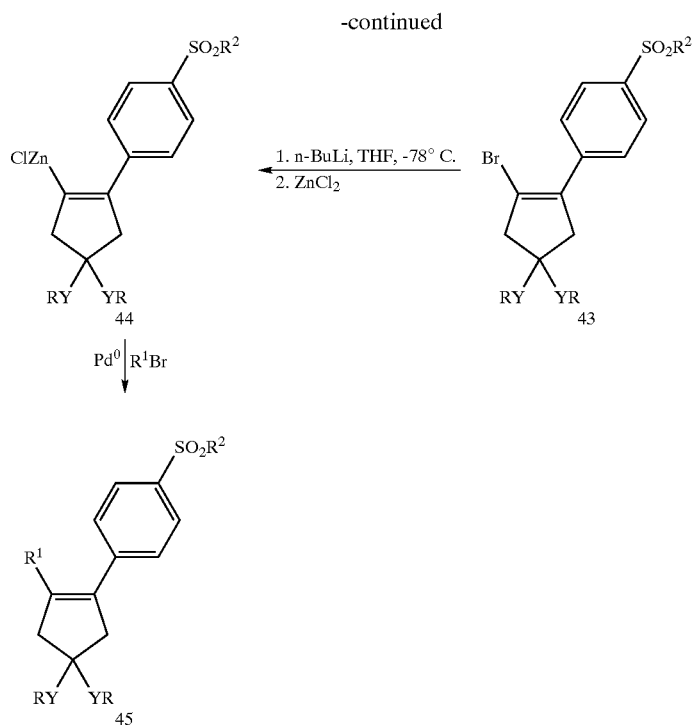

Diaryl/heteroaryl cyclopentenes can be prepared by the methods described in U.S. Pat. No. 5,344,991, and PCT document WO 95/00501, which are incorporated by reference.

Scheme X

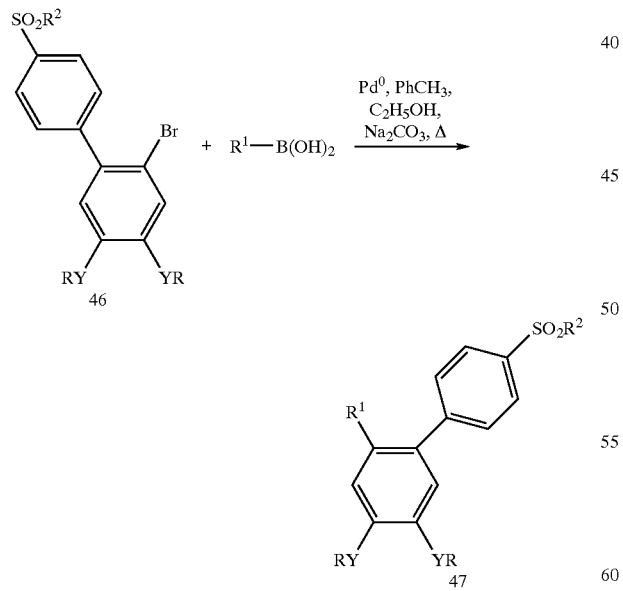

Similarly, Synthetic Scheme X shows the procedure for the preparation of 1,2-diarylbenzene antiinflammatory agents 47 from 2-bromo-biphenyl intermediates 46 (prepared similar to that described in Synthetic Scheme IX) and the appropriate substituted phenylboronic acids. Using a coupling procedure similar to the one developed by Suzuki et al. [*Synth. Commun.*, 11, 513 (1981)], intermediates 46 are reacted with the boronic acids in toluene/ethanol at reflux in the presence of a Pd° catalyst, e.g., tetrakis(triphenylphosphine) palladium (0), and 2M sodium carbonate to give the corresponding 1,2-diarylbenzene antiinflammatory agents 47 of this invention.

Scheme XI

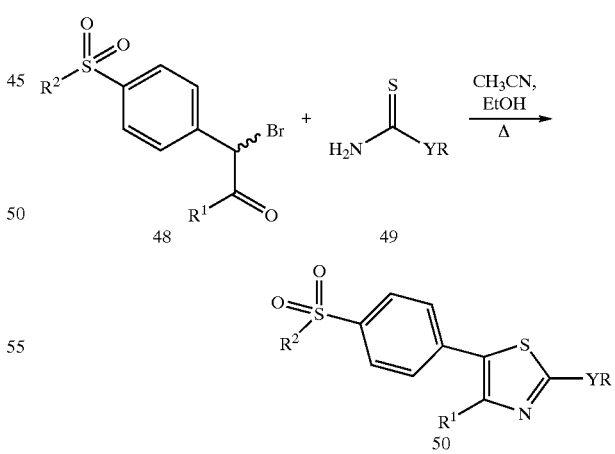

Diaryl/heteroaryl thiazoles can be prepared by the methods described in U.S. Pat. No. 4,051,250, 4,632,930, European Application EP 592,664, and PCT document WO 95/00501, which are incorporated by reference. Isothiazoles can be prepared as described in PCT document WO 95/00501.

Scheme XII

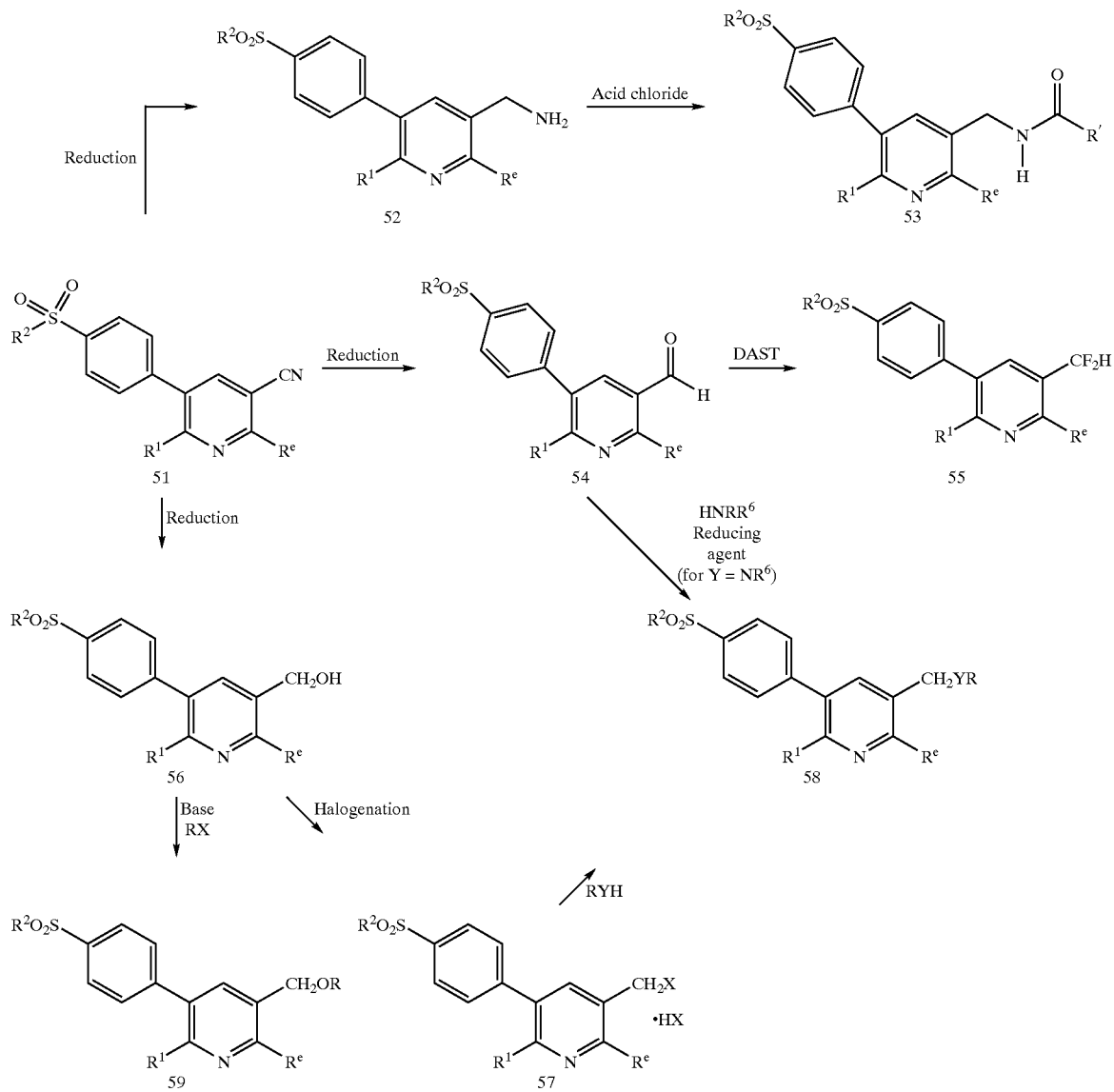

Diary/heteroaryl pyridines can be prepared by the methods described in U.S. Pat. Nos. 5,169,857, 4,011,328, and 4,533,666, which are incorporated by reference. For example, Synthetic Scheme XII shows the procedure used to prepare 3-alkylcarbonylaminoalkyl pyridine antiinflammatory agents 53, 3-haloalkyl pyridine antiinflammatory agents 55, 3-hydroxyalkyl pyridine antiinflammatory agents 56, heteroatom substituted 3-alkyl pyridine antiinflammatory agents 58 and 3-aryloxyalkyl pyridine antiinflammatory agents 59 from the corresponding carbonitriles 51. The 3-alkylcarbonylaminoalkyl pyridine antiinflammatory agents 53 (where R' is alkyl) are prepared in a two step procedure from the carbonitriles 51. In step one, the carbonitrile 51 is reduced using reducing agents, such as diisobutyl aluminum hydride (DIBAL) in a solvent such as toluene or boranes in a solvent such as tetrahydrofuran, at room temperature or reflux to form the aminoalkyl pyridine 52. Additional reducing reagent may be added to the solution. In step two, an acid chloride is added to the aminoalkyl pyridine 52 in a solvent such as ethyl ether or tetrahydrofuran and stirred to form the alkylcarbonylaminoalkyl pyridines 53. The 3-haloalkyl pyridine antiinflammatory agents 55 are prepared in a two step procedure from the carbonitriles 51. In step one, the carbonitriles 51 are reduced using agents, such as diisobutyl aluminum hydride (DIBAL) in a solvent such as toluene, at room temperature to form the aldehydes 54. The 3-hydroxyalkyl pyridines 56 also can be isolated from this reaction. In step two, a halogenating agent, such as diethylamino sulfur trifluoride (DAST) is added to the aldehyde 54 to form the haloalkyl pyridines 55. Reduction of aldehydes 54 with agents such as diisobutyl aluminum hydride (DIBAL) followed by methanol and water in methanol to yield the 3-hydroxyalkyl pyridines 56. Compound 56 is convertible to alkoxyalkyl and aralkoxyalkyl compounds 59 by sequential treatment first with a base and then with an alkyl or aralkyl halide. An example of a suitable base is sodium hydride. Examples of alkyl and aralkyl halides are methyl iodide and benzyl chloride. Alternatively, compound 56 may be converted to the haloalkyl compound 57 using a suitable halogenating agent, such as thionyl chloride. Under such circumstances, the hydrochloride salt may be isolated. This in turn may be converted to compounds 58 by reaction with the appropriate alcohol, thiol, or amine. It may be advantageous to carry out this reaction in the presence of a base. Examples of suitable alcohols are methanol, ethanol, benzyl alcohol and phenol. Examples of suitable thiols are n-butyl mercaptan, benzylthiol and thiophenol. Examples of suitable amines are dimethylamine, benzylamine, N-methylbenzylamine, aniline, N-methylaniline and diphenylamine. Examples of suitable bases are sodium hydride and potassium carbonate. Alternatively, amines are accessible by reaction of aldehyde 54 with a primary or secondary amine in the presence of a reducing agent. Examples of suitable primary amines are methyl amine and ethylamine. An example of a suitable secondary amine is dimethylamine. Suitable reducing agents include sodium cyanoborohydride and sodium borohydride.

Scheme XIII

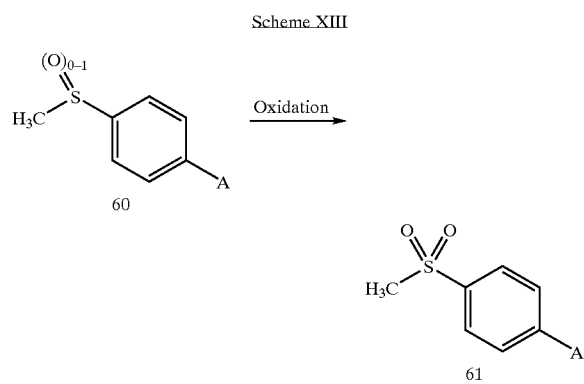

Scheme XIII shows a method to form the alkylsulfonylphenyl substituted heterocycles 61 of the current invention by oxidation of alkylthio or alkylsulfinyl derivatives 60. Aqueous hydrogen peroxide (30%) is added to a suspension of a (methylthio)phenyl substituted heterocycle 60 in acetic acid. The mixture is stirred while heating to about 100° C. for about 2 hours. Alternatively, m-chloroperoxybenzoic acid (MCPBA), and other oxidizing agents [potassium peroxymonosulfate (OXONE®)] can be used to form the sulfonyl radicals 61.

Scheme XIV

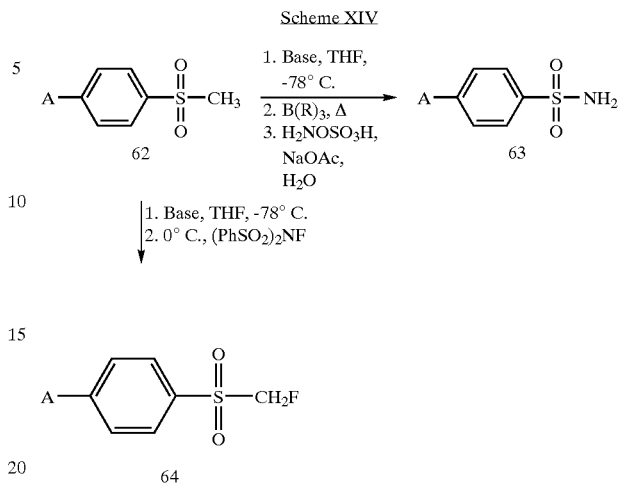

Synthetic Scheme XIV shows the three step procedure used to prepare sulfonamide antiinflammatory agents 63 and the two step procedure used to prepare fluoromethyl sulfone antiinflammatory agents 64 from their corresponding methyl sulfones 62. In step one, THF solutions of the methyl sulfones 62 at −78° C. are treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxylamine-O-sulfonic acid is added to provide the corresponding sulfonamide antiinflammatory agents 63 of this invention. As an alternative to the borane chemistry found in step two above, the base treated sulfone is reacted with an alkylsilane, such as (iodomethyl)trimethylsilane or (chloromethyl) trimethylsilane, at room temperature to give a silylalkylsulfone. The silylalkylsulfone is converted to a sulfinic acid salt by heating to about 90° C. with tetrabutylammonium fluoride. Treatment proceeds as in step three above to produce the sulfonamide.

Alternatively, the anion solutions generated in step one may be warmed to 0° C. and treated with N-fluorodibenzenesulfonamide to provide the corresponding fluoromethyl sulfone antiinflammatory agents 64 of this invention.

Scheme XV

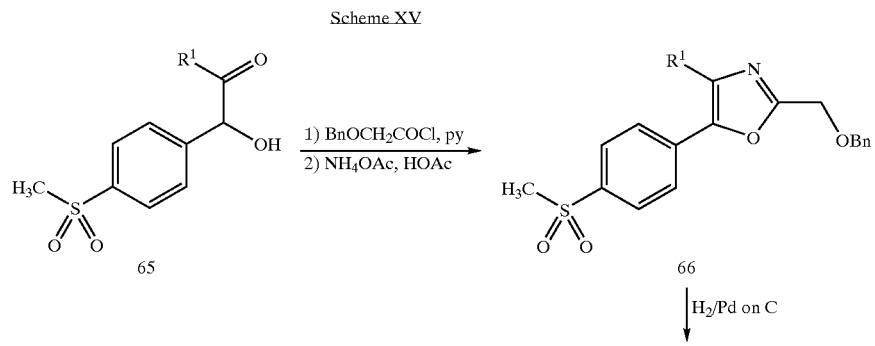

-continued

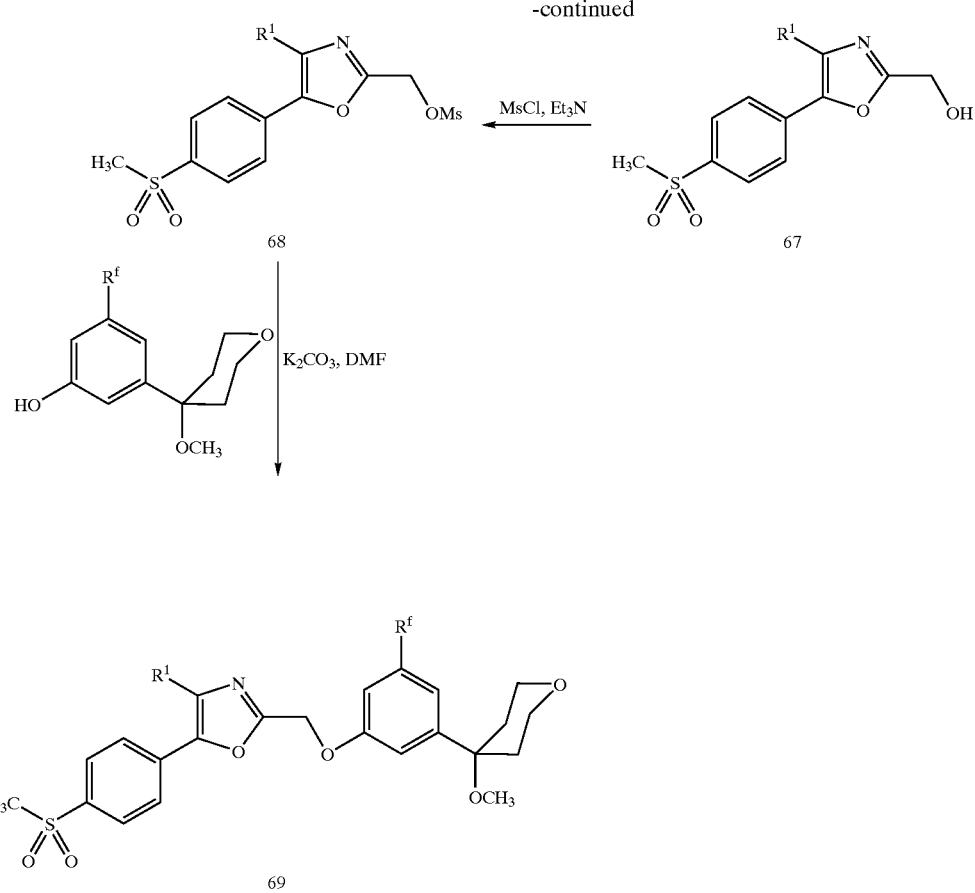

Synthetic Scheme XV shows the four step procedure used to prepare anti-inflammatory compound of Formula II. In step one, a dichloromethane solution of 1-(substitutedphenyl)-2-hydroxy-2-[4-(methylsulfonyl)phenyl]ethanone 65 (described in U.S. Pat. No. 5,380,738) is treated with benzyloxyacetyl chloride in the presence of pyridine base to provide 2-benxyloxymethyl-4-(substitutedphenyl)-5-[4-(methylsulfonyl)phenyl]oxazole 66 in good yield. In step two, the benzyloxy group is removed by hydrogenolysis in the presence of a catalytic amount of 10% palladium on charcoal to provide the hydroxymethyl compound 67. In step three, the hydroxymethyl compound 67 is treated with a solution of methanesulfonyl chloride in the presence of triethylamine base to produce the unstable mesylate 68 that is used directly in the next step. In step four, a mixture of the mesylate and a 3,4,5,6-tetrahydro-2H pyran in dimethylformamide (DMF) is treated with potassium carbonate to effect ether formation and provide the anti-inflammatory agents 69 (where $R^f$ is halo, alkoxy, or alkyl) of the present invention.

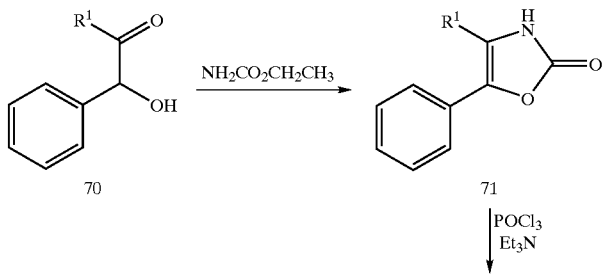

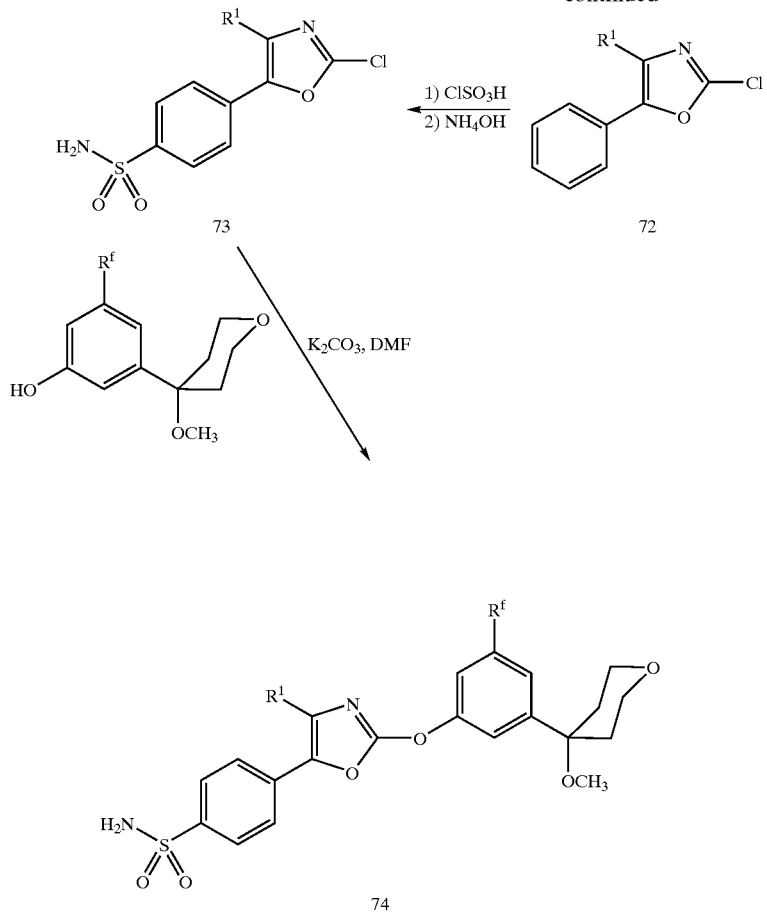

Synthetic Scheme XVI shows the four step procedure that is used to prepare anti-inflammatory compound of Formula II. In step one, benzoin 70 is mixed with ethyl carbamate (urethane) and heated to reflux to provide oxazolone 71 in high yield. In step two, oxazolone 71 is treated with a mixture of phosphorus oxychloride and triethylamine base to produce 2-chloro-5-phenyloxazole 72. In step three, 2-chloro-5-phenyloxazole 72 is treated first with chlorosulfonic acid to effect regioselective chlorosulfonation, followed by treatment with aqueous ammonia provides 2-chloro-5-(4-sulfonamido)phenyloxazole 73 in high yield. In step four, 2-chloro-5-(4-sulfonamido)phenyloxazole 73 and a tetrahydro-2H-pyran-substituted phenol is treated with potassium carbonate to effect ether formation and provide the anti-inflammatory agents of the present invention 74.

Scheme XVII

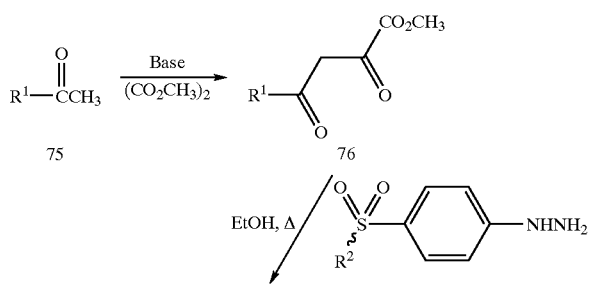

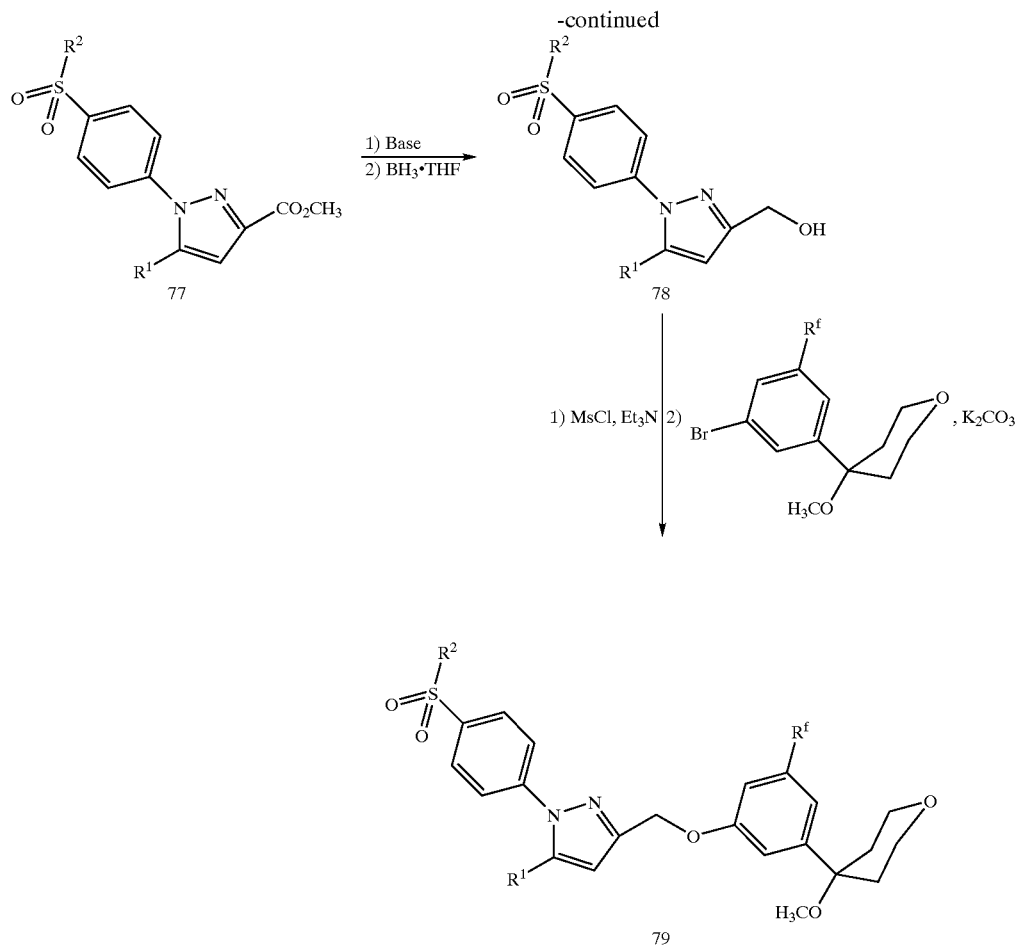

Synthetic Scheme XVII shows a four step method of making the pyrazole phenylethers 79 of the present invention. In step 1, the dione 76 is formed from ketone 75 through the addition of a base, such as lithium bis(trimethylsilyl)amide or lithium diisopropylamide (LDA), followed by reacting with an appropriate acetylating reagent, such as $(CO_2CH_3)_2$. Treatment of the dione 76 with a phenylhydrazine yields the pyrazole ester 77. The pyrazole ester 77 is first treated with base to hydrolyze the ester and is then reduced to the alcohol 78 by treatment with borane in THF. In step four, the alcohol 78 is treated with methanesulfonyl chloride in the presence of triethylamine base to produce the unstable mesylate that is directly reacted with a 3,4,5,6-tetrahydro-2H pyran in dimethylformamide and $K_2CO_3$ to effect ether formation and provide the anti-inflammatory agents 79 of the present invention.

Scheme XVIII

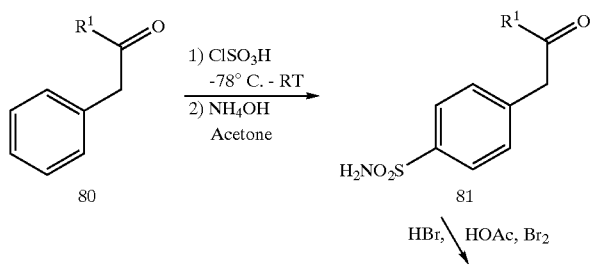

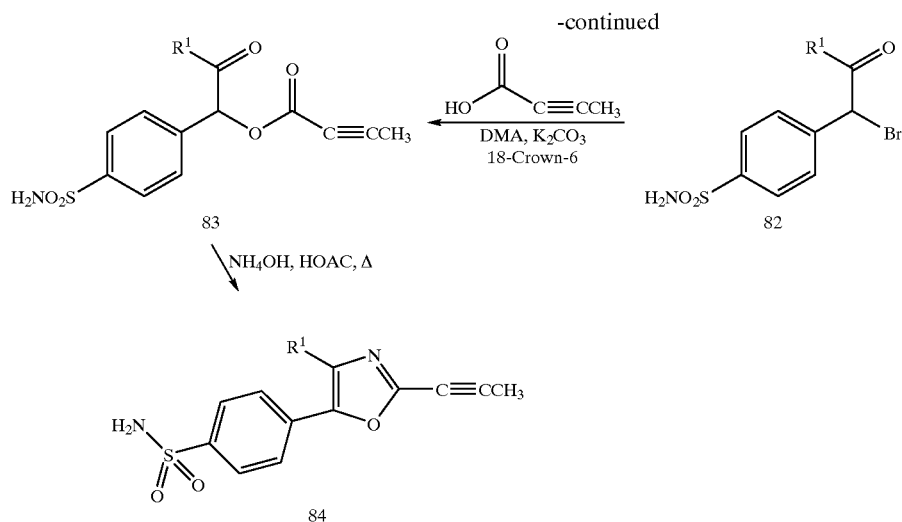

Scheme XVIII shows a procedure for forming an alkynyl oxazole 84 (where $R^2$ is amino), similar to that shown in Scheme V above. The ketone sulfonamide 81 is formed from ketone 80 through chlorosulfonation and ammonolysis with ammonium hydroxide in a solvent such as acetone. The ketone sulfonamide 81 is halogenated, such as with HBr in acetic acid and bromine, to form the haloketone sulfonamide 82. Substitution with butynoic acid in the presence of $K_2CO_3$, a crown ether, such as 18-crown-6, and dimethylacetamide (DMA) yields the alkynyl ketoester 83. Conversion of the alkynyl ester 83 to the alkynyl oxazole 84 proceeds as previously described in Scheme V.

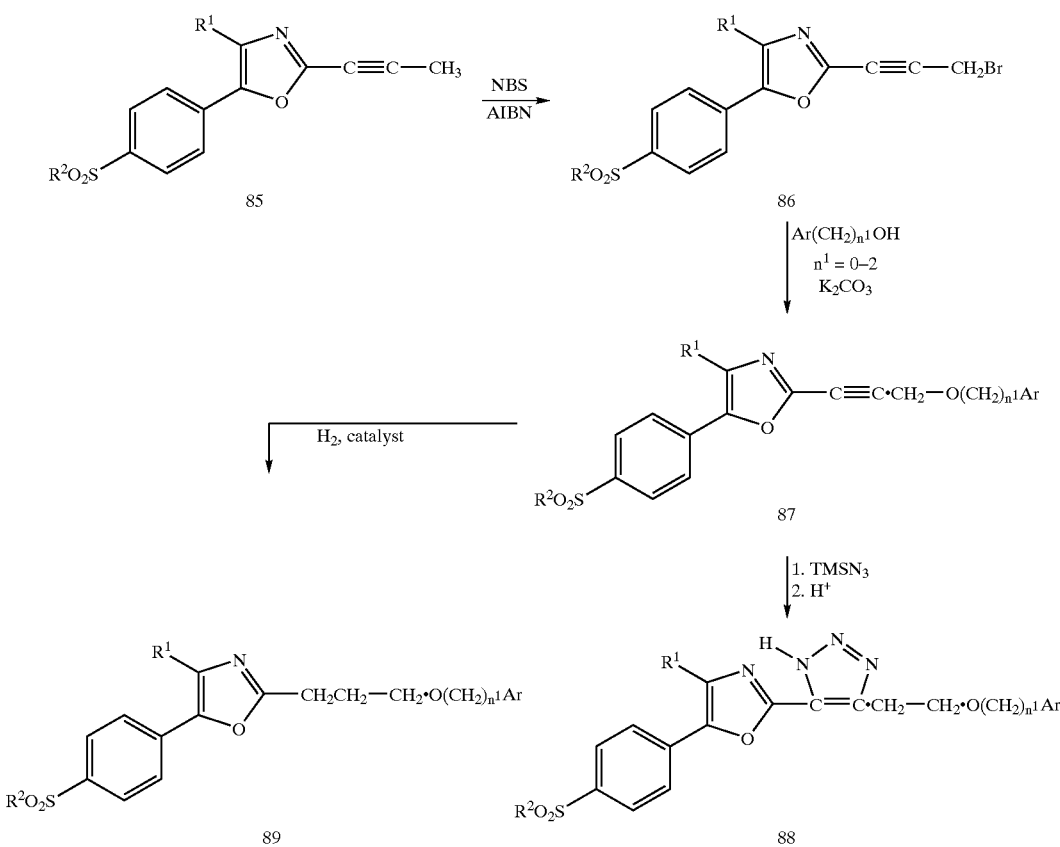

Synthetic Scheme XIX shows the procedures for forming heterocycloalkynylethers 87, heterocyclotriazole ethers 88 and heterocycloalkylethers 89, from the corresponding alkynes 85. The alkynes 85 are halogenated such as with N-bromosuccinimide (NBS) and 2,2'-azobis(2-methylpropionitrile) (AIBN) to form the haloalkynes 86. Substitution with the appropriate aryl or aralkyl alcohols in the presence of potassium carbonate yields the alkynyl ethers 87 of the present invention. The alkynylethers 87 can be converted to heterocyclo-containing spacers 88 by treatment with azidotrimethylsilane, followed by acid. Alternatively, the alkynylethers 87 can be reduced, such as with hydrogen in the presence of catalyst, such as palladium, to yield the heterocycloalkylethers 89.

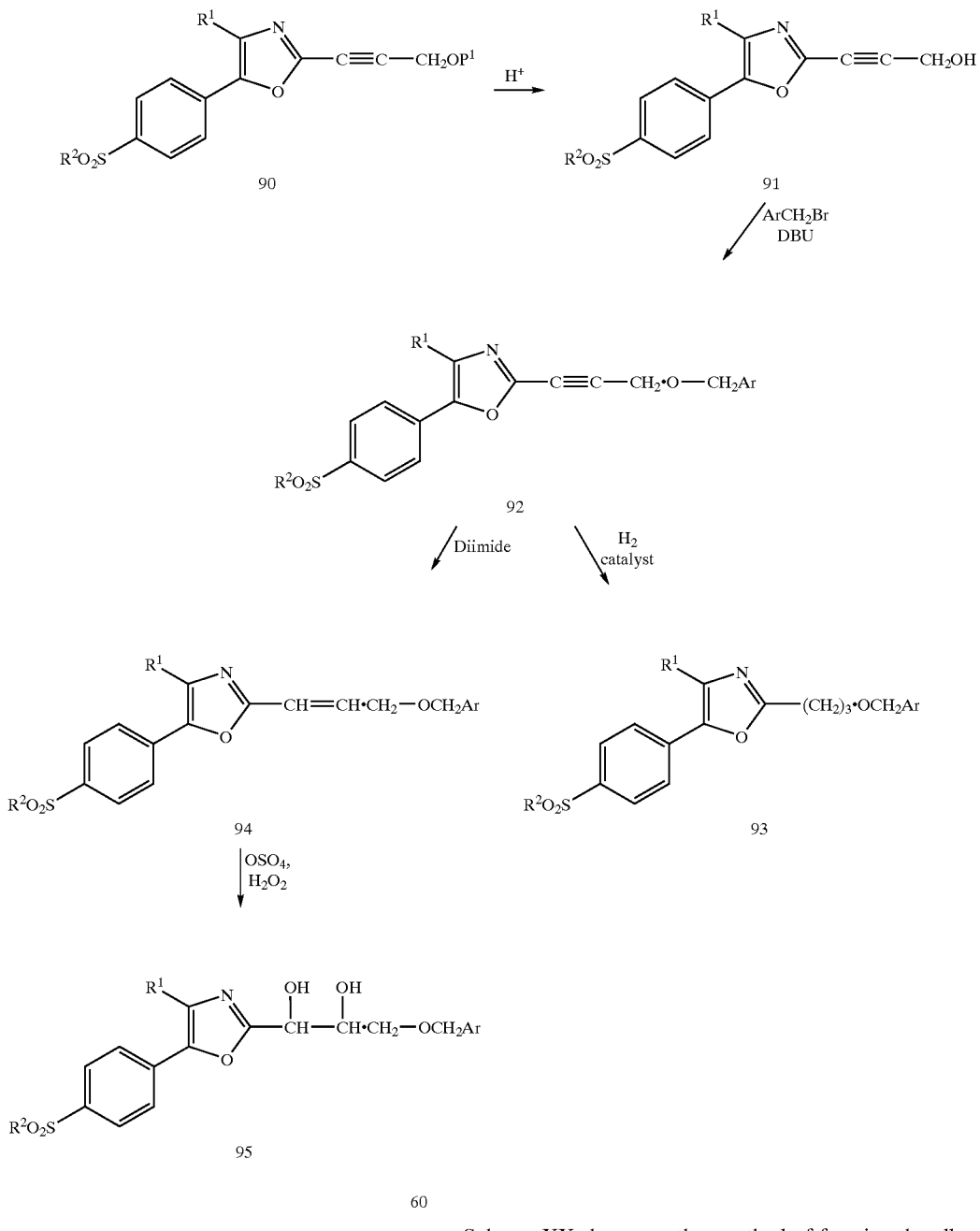

Scheme XX shows another method of forming the alkynylethers 92, alkylethers 93, alkenylethers 94 and the diols 95 of the present invention from the appropriate alkynes 90. In Step one, the alkynes 90 (where P is a protecting group such as tetrahydropyranyl, trialkylsilyl, tert-butyldimethylsilyl or diphenylalkylsilyl) are acid treated to form the alkynyl alcohols 91. Substitution of the alcohol 91 with aralkyl halides or heteroaryl halides in the presence of 1,8-diazabicyclo[5.4.0]undecane (DBU) yields the propynylethers 92 of the present invention. Reduction of the alkynylethers 92 with hydrogen in the presence of metal catalyst yields the alkylethers 93. Alternatively, treatment with diimide reduces the alkynylethers 92 to the alkenylethers 94. Oxidation of the alkenylether 94, such as with osmium tetraoxide and hydrogen peroxide, yields the diols 95 of the present invention.

Additional antiinflammatory agents containing various substituted alkylether spacer radicals including carbonylalkylethers 98, aminoalkylethers 100, hydroxyalkylethers 101, oxyiminoalkylethers 99, and amidoalkylethers 102, can be prepared from ketones 96, by the procedures shown in Scheme XXI. The ketones 96 are halogenated to form halomethylketone 97 such as by treatment with NBS in the presence of AIBN. Substitution of appropriate alcohols with the halides 97 in the presence of base, such as potassium

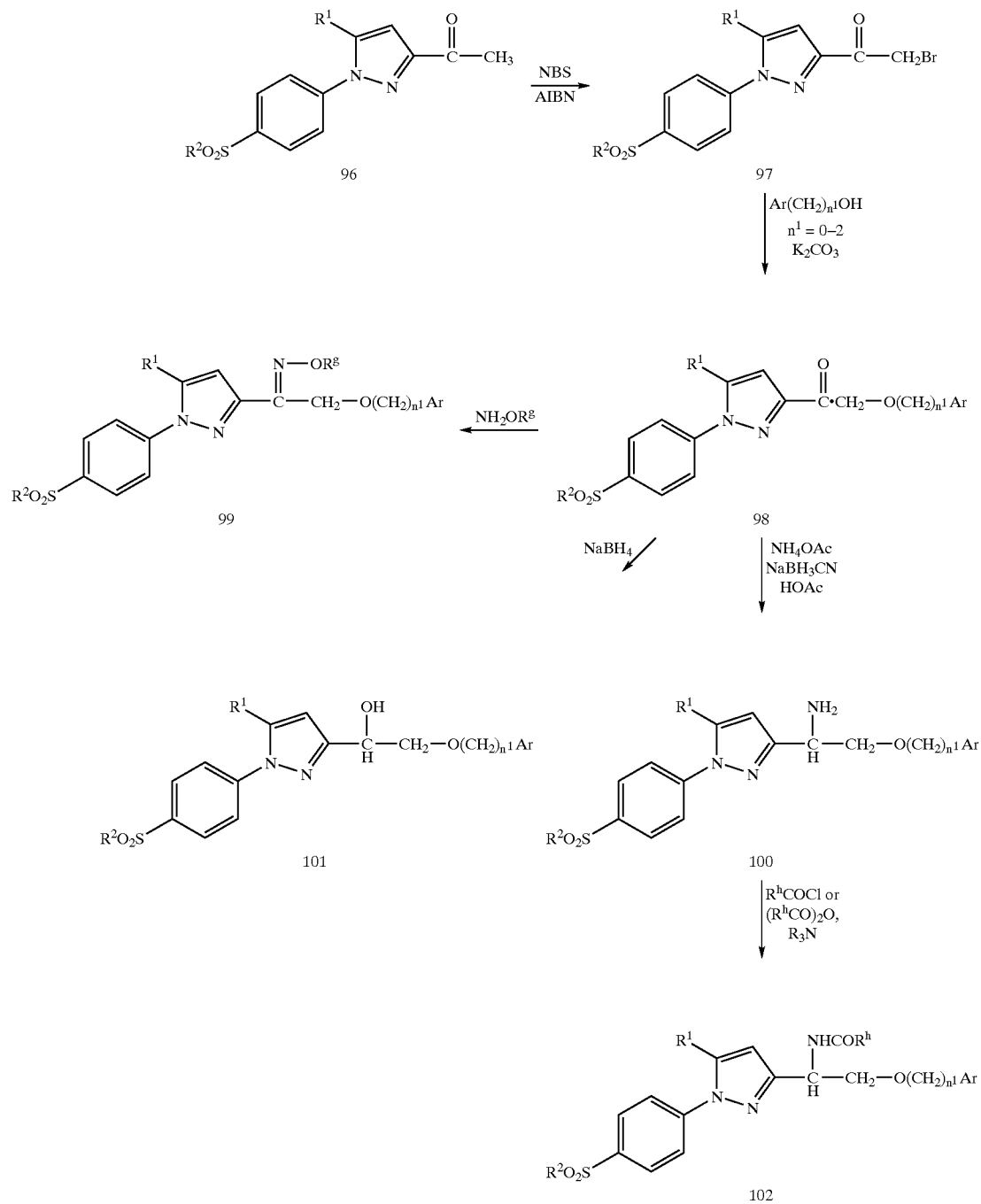

carbonate, generates the ketoalkylethers 98. The ketoalkylethers 98 can be converted to the oxyimino-containing spacers 99 (where $R^g$ is alkyl) by treatment with substituted oxyamines, such as hydroxylamine. Hydroxyalkyl spacers 101 can be prepared by reducing the carbonyl in the ketoalkylethers 99 such as with sodium borohydride. Amination of the ketoalkylethers 99 by reaction with ammonium acetate and sodium cyanoborohydride in the presence of acetic acid generates the aminoalkylethers 100. Acetylation of the aminoethers 100 by acid chlorides or anhydrides in the presence of base, such as trialkylamines, produces the amidoalkylethers 102.

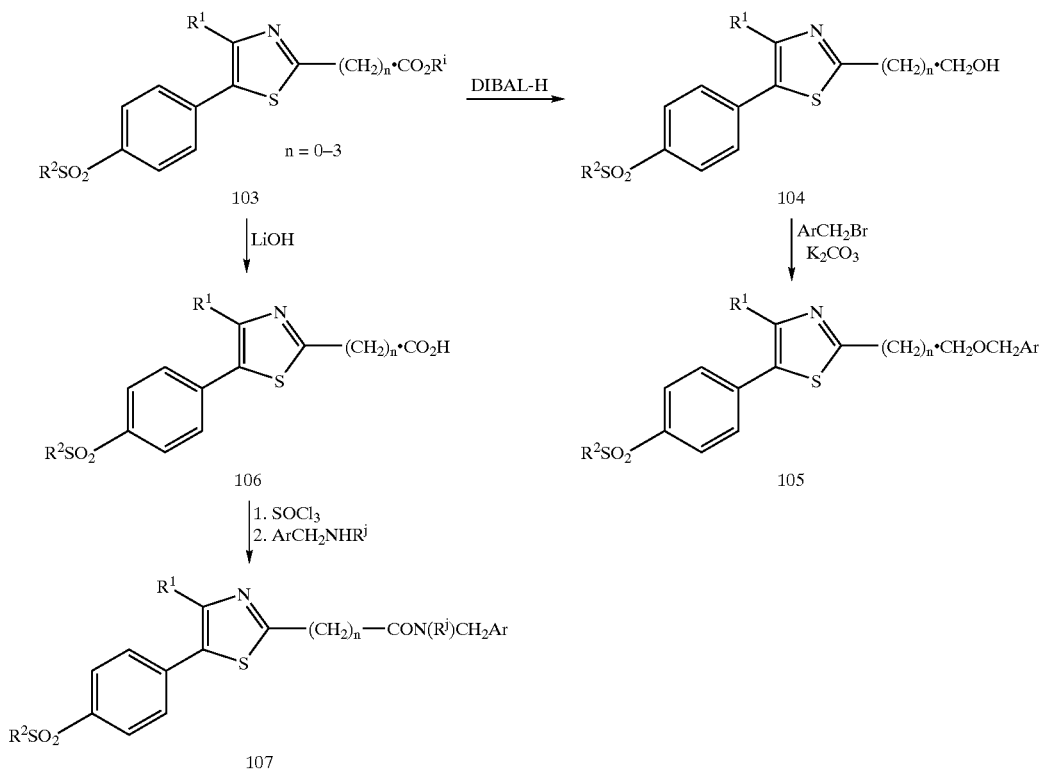

Scheme XXII

Scheme XXII shows the preparation of ethers 105 and amides 107 antiinflammatory agents of the present invention. Esters 103 where $R^i$ is alkyl, can be converted to the alcohols 104 by treatment with a reducing agent, such as DIBAL-H. The ethers 105 are formed by reacting with an aralkyl halide in the presence of base. Alternatively, the esters 103 can be hydrolyzed to the acids 106 with base such as LiOH. Amides 107 are formed from the acid 106 by treatment with thionyl chloride to form the acid chlorides, followed by substitution with aralkylamines.

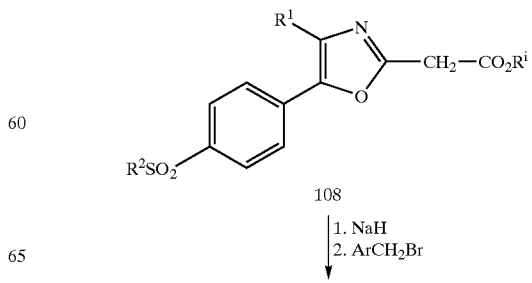

Scheme XXIII

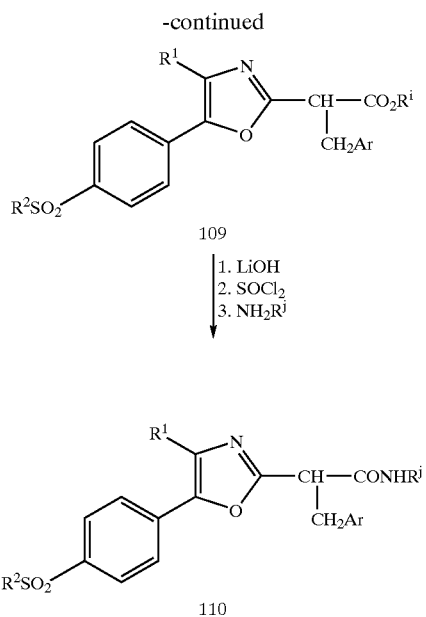

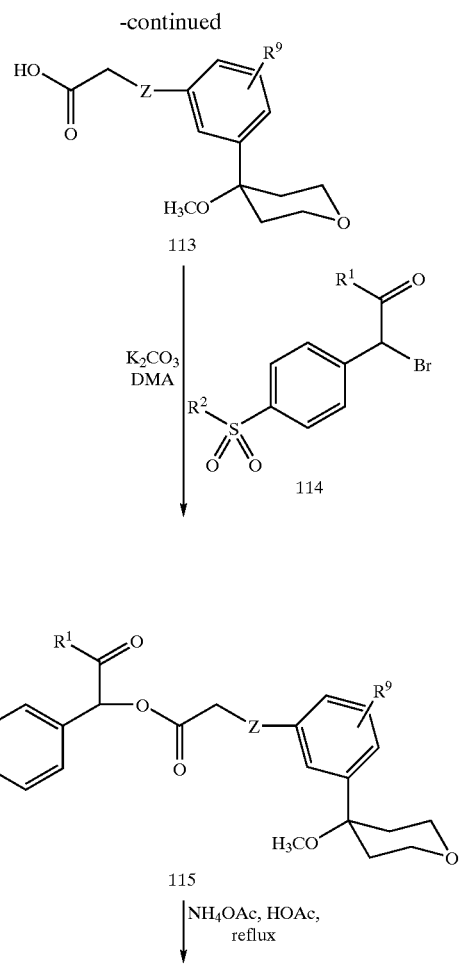

Scheme XXIII shows the preparation of the antiinflammatory esters 109 and amides 110 of the present invention. Base treatment of ester 108, such as with sodium hydride, followed by addition of an aralkyl halide or heteroaralkyl halide forms the ester 109. Formation of the amide 110 from the esters 109 occurs in a three step procedure. Treatment with base, such as lithium hydroxide, and thionyl chloride yields the acid chloride. Addition of an amine yields the amide 110.

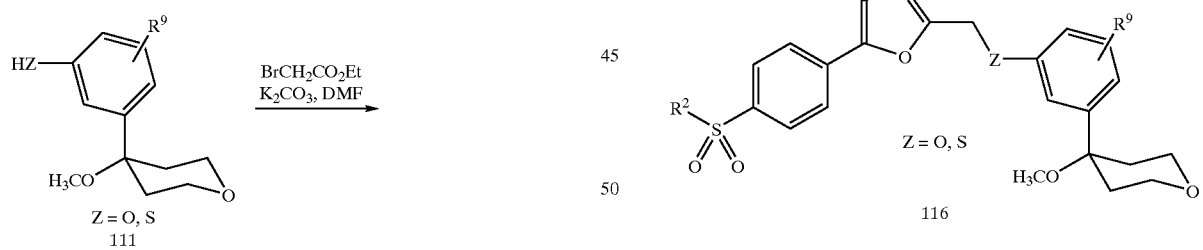

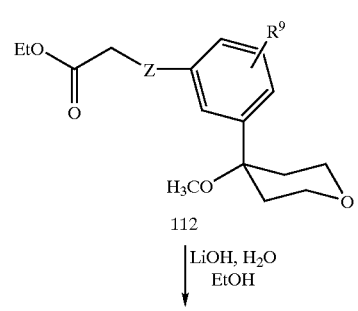

Scheme XXIV shows the preparation of the antiinflammatory ethers and thioethers 116 of the present invention. Ethyl bromoacetate is added to a mixture of hydroxy or mercaptan-substituted-(tetrahydro-2H-pyran-4-yl)benzene 111 and base to give the acetate 112. The acid 113 is formed from acetate 112 such as by treatment with ethanolic LiOH. Addition of bromoethanone 114 to the acid 115 in a solvent such as dimethylformamide gives the benzoin ester 115. The benzoin ester 115 is heated with acetic acid and ammonium acetate to give the oxazole 116.

Scheme XXV

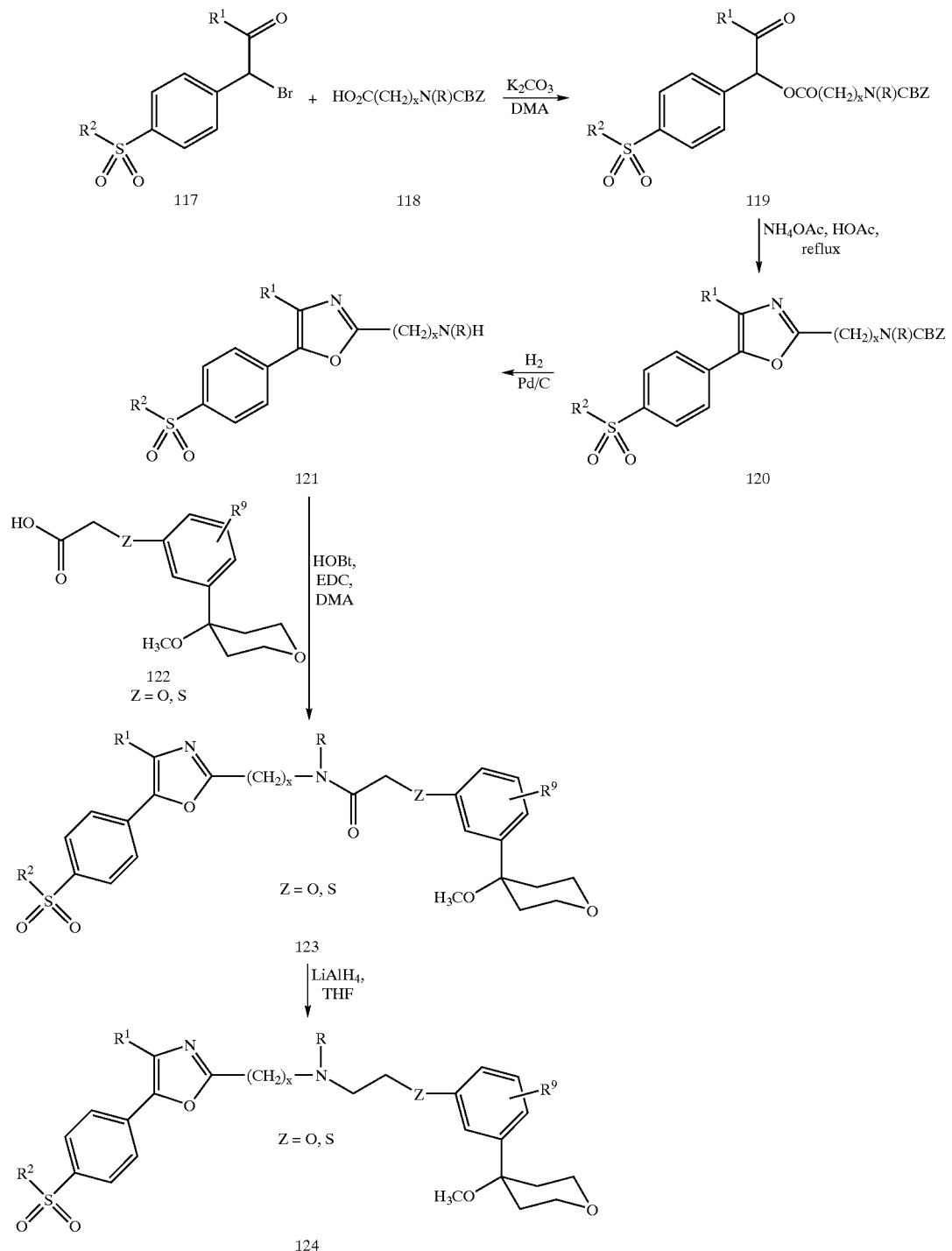

Scheme XXV shows the preparation of the antiinflammatory amides 123 and amines 124 of the present invention. Protected amino acid 118 and bromoethanone 117 is treated with base and 18-crown-6 to afford the benzoin ester 119. This benzoin ester 119 is treated with acetic acid and ammonium acetate and heated to provide the protected 2-(aminoalkyl)oxazole 120. The protected 2-(aminoalkyl) oxazole 120 is deprotected, such as by hydrogenation with 10% Pd on carbon, to give the 2-(aminoalkyl)oxazole 121. (Tetrahydro-2H-pyran-4-yl)phenoxyacetic acid derivative 122 is coupled with 2-(aminoalkyl)oxazole 121 such as with HOBt and EDC to afford amide 123. Reduction of amide 123 such as with LiAlH$_4$ provides the amine 124.

Scheme XXVI

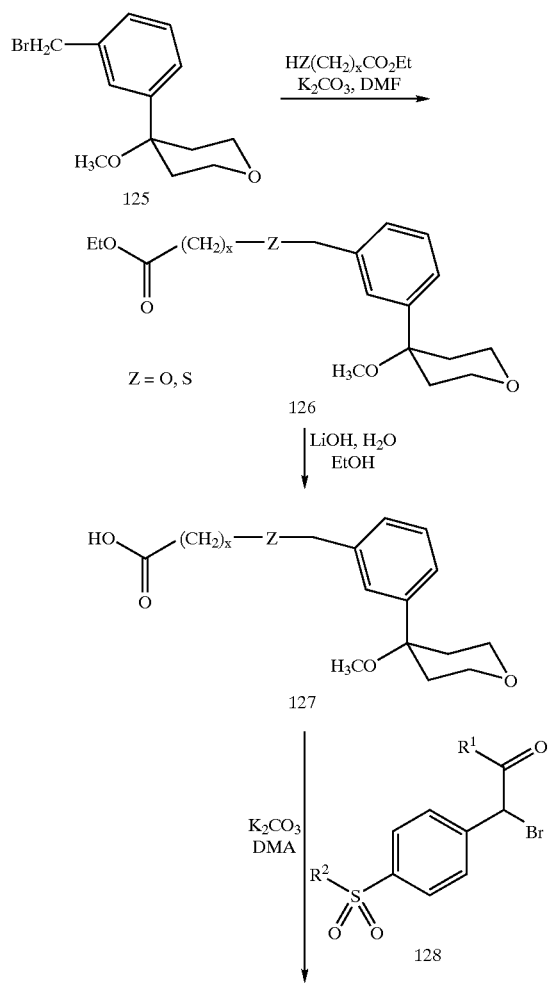

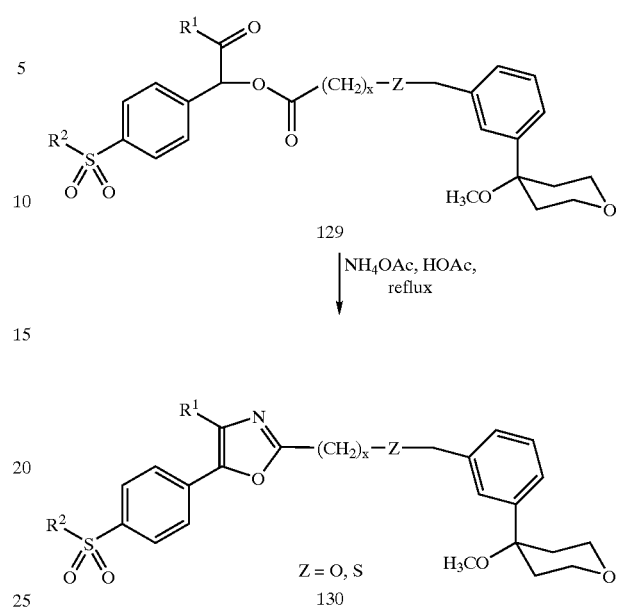

Scheme XXVI shows the preparation of the antiinflammatory ether derivatives 130 of the present invention. A solution of the appropriate hetero-substituted ester and base is added to a [tetrahydropyran-4-yl]-α-bromotoluene 125 to give the [tetrahydropyran-4-yl]phenylmethyl ester 126. The acid 127 is formed from ester 126 such as by treatment with ethanolic LiOH. Base is added to acid 127 and 2-bromoethanone 128 is added to form the benzoin ester 129. Acetic acid and ammonium acetate are added to benzoin ester 129 and heated to give the oxazole 130.

Scheme XXVII

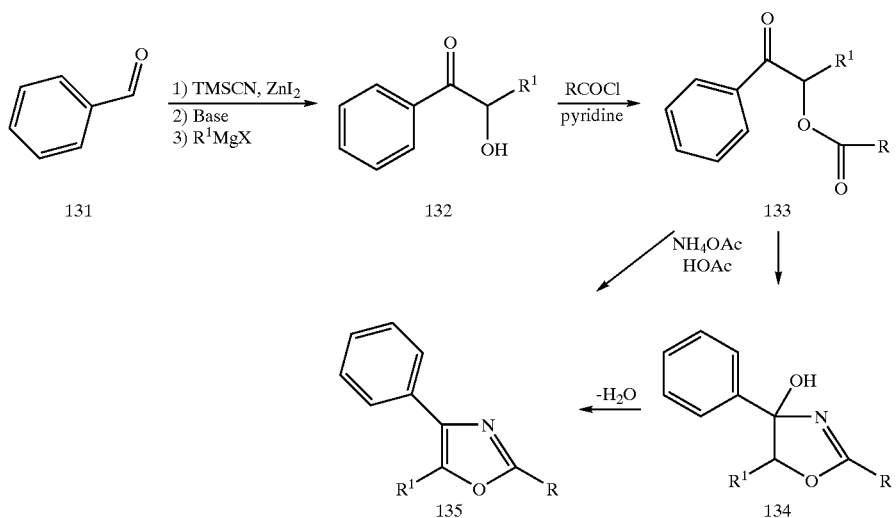

69

Scheme XXVII shows a method for preparing oxazoles 135. A solution of aldehyde 131 and zinc iodide in an organic solvent such as dichloromethane is treated with trimethylsilylcyanide to give the trimethylsilyl cyanohydrin. The trimethylsilyl cyanohydrin is added to a solution of $R^1$-magnesium bromide in diethyl ether while maintaining the temperature between 25–35° C. to give the benzoin 132. The benzoin 132, pyridine, and acid chloride are reacted at room temperature to yield the benzoin ester 133. Addition of ammonium acetate to the benzoin ester 133 and heating yields the oxazole 135. Alternatively, the hydroxy-oxazoline 134 is isolated. Dehydraton of the hydroxy-oxazoline 134 yields the oxazoles 135. By reversing the positions of $R^1$ and the phenyl group in benzoin 132, oxazoles can be prepared where $R^1$ is at position 4.

Scheme XXVIII

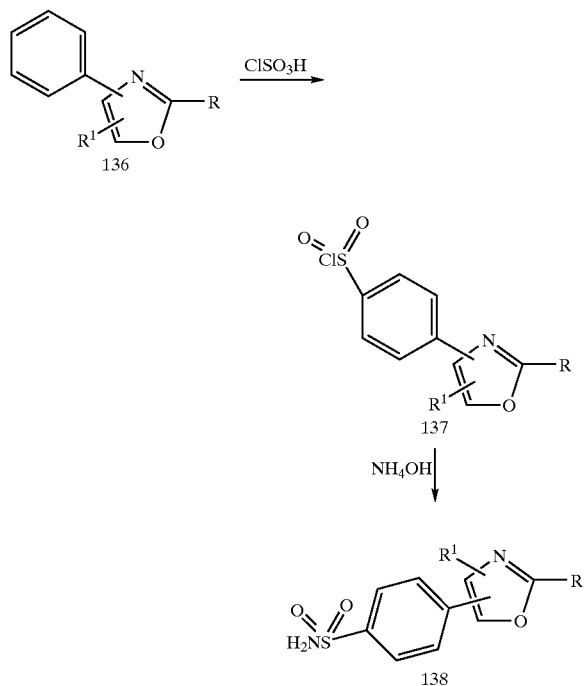

Scheme XXVIII shows a method of preparing oxazolyl-benzenesulfonamides 138 of the present invention. The oxazole 136 is stirred with chlorosulfonic acid at about 5° C. to give the sulfonyl chlorides 137. The sulfonyl chloride 137 is reacted at about 5° C. with ammonium hydroxide to give the sulfonamides 138 of the current invention.

The following examples contain detailed descriptions of the methods of preparation of compounds of Formulas I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

70

EXAMPLE 1

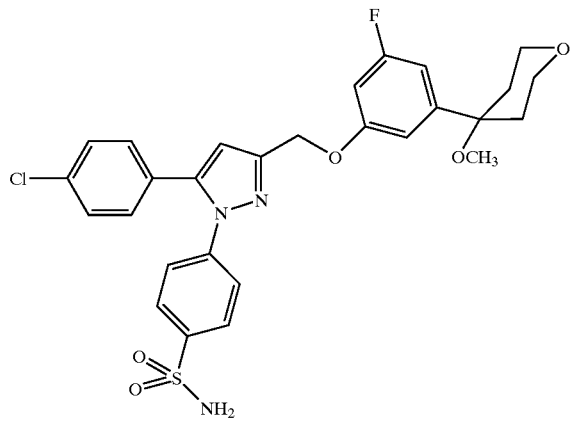

4-[5-(4-Chlorophenyl)-3-[[3-fluoro-5-(3,4,5,6-tetrahydro-4-methoxy-2H-pyran-4-yl)phenoxy]methyl]-1H-pyrazol-1-yl]benzenesulfonamide Step 1. Preparation of Methyl-4-(4-chlorophenyl)-2,4-dioxobutanoate.

Dimethyl oxalate (15.27 g, 0.129 mol) and 4'-chloroacetophenone (20.0 g, 0.129 mol) were diluted with methanol (300 mL) and sodium methoxide (25 wt % in methanol, 70 mL) was added in one portion. The reaction was stirred at room temperature for 16 hours (the reaction became an insoluble mass during this time). The solid was mechanically broken up, hydrochloric acid (conc. 70 mL) was added, and the white suspension was stirred vigorously at room temperature for 1 hour. The suspension was cooled to 0° C. and held for 0.5 hour. The solid was filtered, and the filter cake was washed with cold water (100 mL). Upon drying, methyl-4-[4-(chloro)phenyl]-2,4-dioxobutanoate was obtained (16.94 g, 54.4%) as the enol: mp 108.5–110.5° C. $^1$H NMR (CDCl$_3$/300 MHz) δ 7.94 (d, J=8.66 Hz, 2H), 7.48 (d, J=8.66 Hz, 2H), 7.04 (s, 1H), 3.95 (s, 3H), 3.48 (s, 1H).

Step 2. Preparation of methyl 1-(4-aminosulfonylphenyl)-5-(4-chlorophenyl)-1H-pyrazole-3-carboxylate Methyl-4-[4-(chloro)phenyl]-2,4-dioxobutanoate (5.0 g, 20.78 mmol) was added to 4-sulfonamidylphenyl hydrazine hydrochloride (5.11 g, 22.86 mmol) and methanol (50 mL). The reaction vessel was heated to reflux and held for 16 hours. A precipitate formed overnight. The suspension was cooled to 0° C., held for 0.5 hour, filtered and washed with cold water to provide, after air drying, 7.91 g, 91% of crude pyrazole. Recrystallized 3.50 g from boiling ethanol to yield 3.14 g (90%) of pure methyl 1-(4-aminosulfonylphenyl)-5-(4-chlorophenyl)-1H-pyrazole-3-carboxylate: mp 227° C.; $^1$H NMR (CDCl$_3$/300 MHz) δ 7.91 (d, J=8.86 Hz, 2H), 7.44 (d, J=8.86 Hz, 2H), 7.33 (d, J=8.66 Hz, 2H), 7.14 (d, J=8.66 Hz, 2H), 7.03 (s, 1H), 3.96 (s, 3H). Mass Spectrum, MH+=392. Anal. Calc'd for $C_{17}H_{14}N_3O_4ClS$: C, 52.11; H, 3.60; N, 10.72; Cl, 9.05; S, 8.18. Found: C, 52.07; H, 3.57; N, 10.76; Cl, 9.11; S, 8.27.

Step 3. Preparation of 1-(4-aminosulfonylphenyl)-5-(4-chlorophenyl)-1H-pyrazole-3-carboxylic acid Methyl 1-(4-aminosulfonylphenyl)-5-(4-chlorophenyl)-1H-pyrazole-3-carboxylate (1.0 g, 2.66 mmol) was added to tetrahydrofuran (20 mL). Aqueous sodium hydroxide (2.5 N, 2.7 mL) and water (2.5 mL) were added, and the suspension was heated to reflux and held for 16 hours. The solids all dissolved during this time. The reaction was cooled to room temperature, and hydrochloric acid solution (1 N, 11 mL) was added. The aqueous suspension was extracted with methylene chloride (2×20 mL). The combined organic solution was dried over anhydrous magnesium sulfate, filtered, and concentrated in vacuo to an oil. Trituration with 30 mL of dichloromethane yielded, upon filtration and drying, 0.90 g (94%) of 1-(4-aminosulfonylphenyl)-5-(4-chlorophenyl)-1H-pyrazole-3-carboxylic acid as a white solid: mp 126–128° C.

Step 4. Preparation of 4-[5-(4-chlorophenyl)-3-hydroxymethyl-1H-pyrazol-1-yl]benzenesulfonamide.

4-[4-(Aminosulfonyl)phenyl-5-(4-chlorophenyl)-1H-pyrazole-3-carboxylic acid (3.8 g, 10 mmol) and tetrahydrofuran (100 mL) was stirred at room temperature during the dropwise addition of 1.0 M borane-tetrahydrofuran complex (30 mL, 30 mmol). The mixture was allowed to reflux for 16 hours. The solution was cooled and methanol was added dropwise until gas evolution ceased. Ethyl acetate (100 mL) was added and the solution washed with 1N hydrochloric acid, brine, sat. aq. sodium bicarbonate solution, dried over magnesium sulfate, filtered and concentrated. The resultant material was recrystallized from ethanol:water to yield 4-[5-(4-chlorophenyl)-3-hydroxymethyl-1H-pyrazol-1-yl]benzenesulfonamide (2.6 g, 71%) as a white solid: mp 192–194° C.; $^1$H NMR (DMSO-$d_6$/300 MHz) δ 7.81 (d, j=8.7 Hz, 2H), 7.46 (d, J=8.4 Hz, 2H), 7.42 (brs, 2H), 7.40 (d, J=8.7 Hz, 2H), 7.26 (d, J=8.4 Hz, 2H), 6.63 (s, 1H), 5.35 (t, J=8.0 Hz, 1H), 4.50 (d, J=8.0 Hz, 2H). Anal. Calc'd for $C_{16}H_{14}N_3SO_2Cl$: C, 52.82; H, 3.88; N, 11.55. Found: C, 52.91; H, 3.88; N, 11.50.

Step 5. Preparation of 4-[5-(4-chlorophenyl)-3-[[3-fluoro-5-(3,4,5,6-tetrahydro-4-methoxy-2H-pyran-4-yl)phenoxy]methyl]-1H-pyrazol-1-yl]benzenesulfonamide.

A solution of (569 mg, 1.56 mmol) of 4-[5-(4-chlorophenyl)-3-hydroxymethyl-1H-pyrazol-1-yl]benzenesulfonamide in 50 mL of dichloromethane was stirred at 25° C. as triethylamine (315 mg, 3.12 mmol) was added dropwise, followed by the addition of methanesulfonyl chloride (215 mg, 1.88 mmol). The reaction was stirred for 5 minutes, after which the organic solution was washed with 1N HCl, dried over sodium sulfate and concentrated in vacuo to give a yellow oil (500 mg), which was characterized as the expected mesylate by its NMR spectrum. This material was used without further purification. 4-(5-Fluoro-3-hydroxyphenyl)-4-methoxytetrahydropyran (373 mg, 1.649 mmol) and anhydrous potassium carbonate (228 mg, 1.649 mmol) were dissolved in 25 mL of anhydrous DMF. The solution was stirred at room temperature under a blanket of dry nitrogen for 20 minutes, then a solution of mesylate (500 mg, 1.374 mmol) in anhydrous DMF (15 mL) was added in one portion. The resulting solution was stirred at room temperature for 72 hours, then 1N HCl (30 mL) was added. After stirring an additional 0.5 hour, the system was extracted with ethyl acetate (2×40 mL). The combined organic solution was sequentially washed with 1 N HCl (40 mL), saturated aqueous NaHCO$_3$ (2×40 mL), 50% saturated NaCl (2×40 mL), and brine (40 mL), dried over MgSO$_4$ and filtered. The solvents were evaporated under reduced pressure to yield an oil. The oil was purified by flash chromatography on silica gel eluting with 40% ethyl acetate in hexane to yield, upon concentration of the appropriate fractions (200 mg, 25%) of 4-[5-(4-chlorophenyl)-3-[[3-fluoro-5-(3,4,5,6-tetrahydro-4-methoxy-2H-pyran-4-yl)phenoxy]methyl]-1H-pyrazol-1-yl]benzenesulfonamide as a foam: Mass Spectrum: 572 (M+). High resolution mass spectrum Calc'd for $C_{28}H_{27}N_3O_4ClFS$: 572.1422. Found: 572.1361. Anal. Calc'd. for $C_{28}H_{27}N_3O_4ClFS.1.4\ H_2O$: C, 57.86; H, 5.17; N, 7.23; Cl, 6.10; S, 5.52. Found: C, 57.87; H, 4.92; N, 6.97; Cl, 6.10; S, 5.71.

EXAMPLE 2

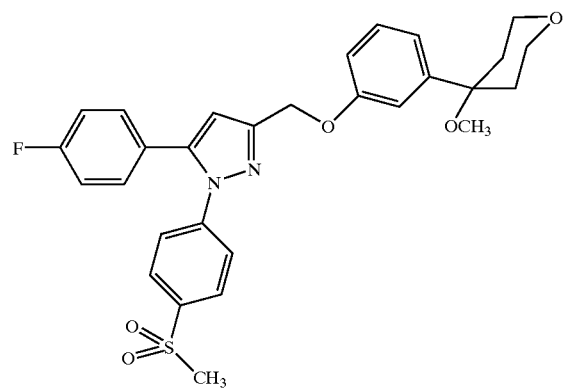

4-(4-Fluorophenyl)-5-(4-(methylsulfonyl)phenyl)-2-[[3-(3,4,5,6-tetrahydro-4-methoxy-2H-pyran-4-yl)phenoxy]methyl]oxazole Step 1. Esterification of 1-(4-fluorophenyl)-2-hydroxy-2-[4-(methylsulfonylphenyl)ethanone A solution containing (2.07 g, 6.71 mmol) of 1-(4-fluorophenyl)-2-hydroxy-2-[4-(methylsulfonylphenyl)ethanone (U.S. Pat. No. 5,380,738, Jan. 10, 1995) in 100 mL of dichloromethane was stirred at 25° C. as (2.71 mL, 33.55 mmol) of pyridine was added, followed by the addition of (1.27 mL, 8.05 mmol) of benzyloxyacetyl chloride. The reaction was stirred at 25° C. for 48 hours, after which the resulting yellow solution was washed with 1N HCl, dried over Na$_2$SO$_4$ and concentrated in vacuo. The oily yellow solid was purified via flash chromatography on a silica gel column using 20% ethyl acetate/hexane as the eluent. This provided 2.22 g (73%) of a white foam, which was characterized as the benzoin ester on the basis of its NMR spectra: $^1$H-NMR (CDCl$_3$, 300 MHz) δ 3.03 (s, 3H), 4.23 (d, 1H, J=17.0 Hz), 4.33 (d, 1H, J=17.0 Hz), 4.67 (s, 2H), 6.95 (s, 1H), 7.13 (t, 2H, J=8.5 Hz), 7.35 (m, 5H), 7.66 (d, 2H, J=8.1 Hz) and 7.98 (m, 4H). $^{19}$F-NMR (CDCl$_3$, 280 MHz) δ −102.5.

Step 2. Preparation of 2-benzyloxymethyl-4-(4-fluorophenyl)-5-[4-(methylsulfonyl)phenyl]oxazole.

A solution containing (2.22 g, 4.86 mmol) of the benzoin ester from Step 1 and (3.74 g, 48.6 mmol) of ammonium acetate in 100 mL of acetic acid was heated to 80° C. for 2 hours. The reaction was cooled to 25° C. and poured into water. The product was extracted into ethyl acetate and the combined organic extracts were washed with an aqueous solution of sodium bicarbonate. The solution was dried over sodium sulfate and concentrated in vacuo to give a yellow oil. This crude material was purified by flash chromatography on a silica gel column using 25% ethyl acetate/hexane as the eluent to give 2-benxyloxymethyl-4-(4-fluorophenyl)-5-[4-(methylsulfonyl)phenyl]oxazole (1.92 g, 90%) as a clear oil: $^1$H-NMR (CDCl$_3$, 300 MHz) δ 3.07 (s, 3H), 4.70 (s, 2H), 4.72 (s, 2H), 7.11 (t, 2H, J=8.8 Hz), 7.22–7.40 (m, 5H), 7.58 (m, 2H), 7.76 (d, 2H, J=8.8 Hz) and 7.91 (d, 2H, J=8.8 Hz). $^{19}$F-NMR (CDCl$_3$, 280 MHz) δ −111.88.

Step 3. Preparation of 4-(4-fluorophenyl)-2-hydroxymethyl-5-[4-(methylsulfonyl)phenyl]oxazole.

To a solution containing 2-benxyloxymethyl-4-(4-fluorophenyl)-5-[4-(methylsulfonyl)phenyl]oxazole from Step 2 (5.0 g, 11.4 mmol) in 20 mL of 50% THF/methanol was added 100 mg of 10% Pd on charcoal in a Fisher-Porter bottle. The reaction vessel was evacuated and charged with hydrogen at 50 psi for 24 hours. The Pd on carbon was removed by filtration through diatomaceous earth and the filtrate was concentrated in vacuo to give 4-(4-fluorophenyl)-2-hydroxymethyl-5-[4-(methylsulfonyl)phenyl]oxazole (3.8 g, 97%) as a white crystalline solid (recrystallized from 50% ethyl acetate-isooctane): mp 156–157° C.; $^1$H-NMR (CDCl$_3$, 300 MHz) δ 3.07 (s, 3H), 3.21 (bs, 1H), 4.81 (s, 2H), 7.10 (t, 2H, J=8.5 Hz), 7.56 (m, 2H), 7.72 (d, 2H, J=8.8 Hz) and 7.90 (d, 2H, J=8.8 Hz); $^{19}$F-NMR (CDCl$_3$, 280 MHz) δ −111.5. LRMS m/z 348 (M+H). HRMS Calc'd. for C$_{17}$H$_{14}$NO$_4$FS: 348.0706. Found: 348.0681. Anal. Calc'd. for C$_{17}$H$_{14}$NO$_4$FS: C, 58.78; H, 4.06; N, 4.03. Found: C, 58.67; H, 4.02; N, 4.01.

Step 4. Preparation of 4-(4-fluorophenyl)-5-(4-(methylsulfonyl)phenyl)-2-[[3-(3,4,5,6-tetrahydro-4-methoxy-2H-pyran-4-yl)phenoxy)methyl]oxazole.

A solution containing 4-(4-fluorophenyl)-2-hydroxymethyl-5-[4-(methylsulfonyl)phenyl]oxazole from Step 3 (169 mg, 0.487 mmol) in 20 mL of dichloromethane was stirred at 25° C. as triethylamine (136 μL, 0.974 mmol) was added dropwise, followed by the addition of mechanesulfonyl chloride (56 μL, 0.730 mmol). The reaction was stirred for 5 minutes, after which the organic solution was washed with 1N HCl, dried over sodium sulfate and concentrated in vacuo to give a yellow oil which was characterized as the expected mesylate by its NMR spectrum: $^1$H-NMR (CDCl$_3$, 400 MHz) δ 3.08 (s, 3H), 3.17 (s, 3H), 5.37 (s, 2H), 7.12 (t, 2H, J=8.8 Hz), 7.58 (m, 2H), 7.78 (d, 2H, J=8.8 Hz) and 7.94 (d, 2H, J=8.8 Hz). This material was used without further purification. The mesylate was dissolved in 20 mL of DMF and potassium carbonate (81 mg, 0.584 mmol) was added, followed by the addition of 4-(3-hydroxyphenyl)-4-methoxy-3,4,5,6-tetrahydro-2H-pyran (122 mg, 0.584 mmol). The reaction was stirred at 25° C. for 3 days and poured into 100 mL of water. The aqueous solution was extracted with ethyl acetate and the combined extracts were dried over sodium sulfate and concentrated in vacuo to give a beige solid. This material was purified by flash chromatography on a silica gel column using 50% ethyl acetate/hexane as the eluent to give 4-(4-fluorophenyl)-5-(4-(methylsulfonyl)phenyl)-2-[[3-(3,4,5,6-tetrahydro-4-methoxy-2H-pyran-4-yl)phenoxy)methyl]oxazole (185 mg, 71%) as a white crystalline solid: $^1$H-NMR (CDCl$_3$, 300 MHz) δ 1.90–2.05 (m, 4H), 2.97 (s, 3H), 3.08 (s, 3H), 3.81 (m, 4H), 5.25 (s, 2H), 6.98–7.17 (m, 5H), 7.33 (t, 1H, J=7.7 Hz), 7.60 (m, 2H), 7.78 (d, 2H, J=8.5 Hz) and 7.93 (d, 2H, J=8.5 Hz). $^{19}$F-NMR (CDCl$_3$, 280 MHz) δ −111.6. LRMS m/z 544 (M+Li). HRMS Calc'd. for C$_{29}$H$_{28}$NO$_6$FS: 544.1781 (M+Li). Found: 544.1831 (M+Li).

EXAMPLE 3

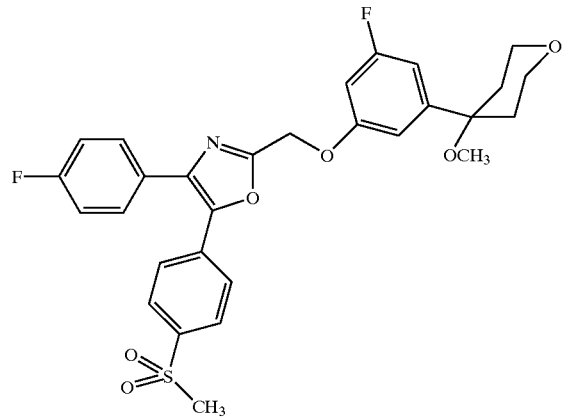

4-(4-Fluorophenyl)-2-[[3-fluoro-5-(3,4,5,6-tetrahydro-4-methoxy-2H-pyran-4-yl)phenoxy)methyl]-5-(4-(methylsulfonyl)phenyl)oxazole 4-(4-Fluorophenyl)-2-[[3-fluoro-5-(3,4,5,6-tetrahydro-4-methoxy-2H-pyran-4-yl)phenoxy)methyl]-5-(4-(methylsulfonyl)phenyl)oxazole was prepared in a similar fashion from the reaction of the mesylate (Example 2, Step 4) and 4-(3-fluoro-5-hydroxyphenyl)-4-methoxy-3,4,5,6-tetrahydro-2H-pyran: $^1$H-NMR (CDCl$_3$, 300 MHz) δ 1.84–2.02 (m, 4H), 2.98 (s, 3H), 3.08 (s, 3H), 3.81 (m, 4H), 5.23 (s, 2H), 6.76 (m, 2H), 6.92 (s, 1H), 7.13 (m, 2H), 7.60 (m, 2H), 7.79 (d, 2H, J=8.5 Hz) and 7.93 (d, 2H, J=8.5 Hz). $^{19}$F-NMR (CDCl$_3$, 280 MHz) δ −110.8 and −111.7. Anal. Calc'd. for C$_{29}$H$_{27}$NO$_6$F$_2$: C, 62.69; H, 4.90; N, 2.52. Found: C, 62.53; H, 4.96; N, 2.51.

EXAMPLE 4

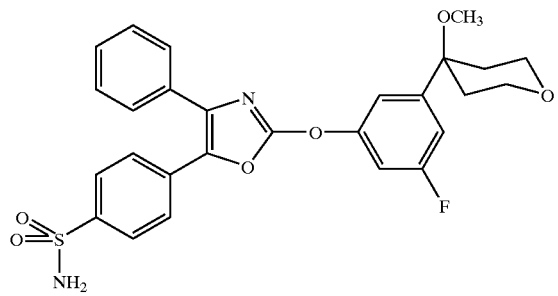

4-[2-[3-Fluoro-5-(4-methoxy-3,4,5,6-tetrahydro-2H-pyran-4-yl)phenoxy]-4-phenyl-5-oxazolyl]benzenesulfonamide Step 1. Preparation of 4,5-diphenyloxazolone.

Benzoin (31.8 g, 0.15 mol) and urethane (42.79 g, 0.45 mol) were heated to reflux for 3.0 hours. The hot mixture was poured into water (150 mL). Acetone (150 mL) was added and heat was applied until the mixture dissolved. The solution was cooled and filtered, producing a white solid which was used in the next step without further purification.

Step 2. Preparation of 2-chloro-4,5-diphenyloxazole.

4,5-Diphenyloxazolone from Step 1 (30 g, 0.126 mol), triethylamine (12.8 g, 0.126 mol), and phosphorous oxychloride (96.6 g, 0.63 mol) were stirred at reflux for 4.0 hours. The mixture was concentrated in vacuo, dissolved in ether (250 mL), washed with 1N HCl, brine, and water, dried over MgSO$_4$ and concentrated to a light yellow oil which was used in the next step without further purification or characterization.

Step 3. Preparation of 4-[2-chloro-4-phenyl-5-oxazolyl]benzenesulfonamide.

Chlorosulfonic acid (20 mL) was cooled to 0° C. with stirring. 2-Chloro-4,5-diphenyloxazole from Step 2 (1.53 g, 6 mmol) was added, and the stirred solution was warmed to room temperature over 1.0 hour. The mixture was added dropwise to ice and dichloromethane (50 mL) with stirring. The resultant organic layer was washed once with water and added to a 0° C. stirred solution of ammonium hydroxide (10 mL). The mixture was stirred for 1.0 hour and extracted with dichloromethane (3×50 mL). The combined organic layers were washed with 1 N HCl followed by brine and water, dried over MgSO$_4$ and concentrated. Recrystallization from ethyl acetate/hexanes gave a white solid (1.5 g, 75%): mp 158–159° C. Anal. Calc'd. for $C_{15}H_{11}N_2O_3SCl$: C, 53.82; H, 3.31; N, 8.37. Found: C, 53.92; H, 3.32; N, 8.33.

Step 4. Preparation of 4-[2-[3-fluoro-5-(4-methoxy-3,4,5,6-tetrahydro-2H-pyran-4-yl)phenoxy]-4-phenyl-5-oxazolyl]benzenesulfonamide 4-[2-Chloro-4-phenyl-5-oxazolyl]benzenesulfonamide from Step 3 (0.74 g, 2.2 mmol), N,N'-dimethylformamide (DMF) (20 mL), potassium carbonate (0.61 g, 4.4 mmol), and 4-(3-fluoro-5-hydroxyphenyl)-4-methoxy-3,4,5,6-tetrahydro-2H-pyran [prepared as described by G. C. Crawley, et al, *J. Med. Chem.*, 35, 2600–2609 (1992)] (0.75 g, 7.5 mmol) were stirred at room temperature for 16.0 hours. The solution was diluted with ethyl acetate (100 mL), washed with 1N HCl, brine and water, dried over MgSO$_4$ and concentrated. The residue was dissolved in ethyl acetate/hexanes (1:1) and filtered through silica. The eluant was concentrated and the residue was recrystallized from ethyl acetate/hexanes to afford 4-[2-[3-fluoro-5-(4-methoxy-3,4,5,6-tetrahydro-2H-pyran-4-yl)phenoxy]-4-phenyl-5-oxazolyl]benzenesulfonamide as a white solid (0.4 g, 35%): mp 159–161° C. $^1$H NMR (CDCl$_3$) 300 MHz δ 7.9 (d, J=8.7 Hz, 2H) 7.72 (d, J=8.7 Hz, 2H) 7.6 (m, 2H) 7.4 (m, 3H) 7.24–7.30 (m, 2H) 7.0–7.1 (dt, J=9.5 Hz and J=1.8 Hz, 1H) 4.85 (bs, 2H) 3.85 (dd, J=9.9 Hz and J=1.8 Hz, 4H) 3.05 (s, 3H) 2.0 (m, 4H). Anal. Calc'd. for $C_{27}H_{25}N_2O_6SF$: C, 61.82; H, 4.80; N, 5.34. Found: C, 61.77; H, 4.82; N, 4.31.

EXAMPLE 5

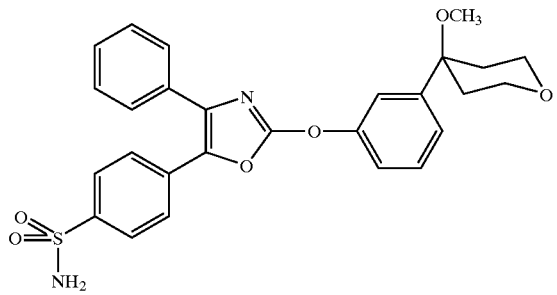

4-[2-[3-(4-Methoxy-3,4,5,6-tetrahydro-2H-pyran-4-yl)phenoxy]-4-phenyl-5-oxazolyl]benzenesulfonamide 4-(2-Chloro-4-phenyl-5-oxazolyl]benzenesulfonamide from Example 4, Step 3, (0.6 g, 1.8 mmol), DMF (20 mL), potassium carbonate (0.5 g, 3.6 mmol), and 4 (3-hydroxyphenyl)-4-methoxy-3,4,5,6-tetrahydro-2H-pyran (0.37 g, 1.8 mmol) [prepared as described by G. C. Crawley, et al, *J. Med. Chem.*, 35, 2600–2609 (1992)] were stirred at room temperature for 16.0 hours. The solution was diluted with ethyl acetate (100 mL), washed with 1N HCl, brine and water, dried over MgSO$_4$ and concentrated. The residue was dissolved in ethyl acetate/hexanes (1:1) and filtered through silica. The eluant was concentrated and the residue recrystallized from ethyl acetate/hexanes to give 4-[2-(3-(4-methoxy-3,4,5,6-tetrahydro-2H-pyran-4-yl)phenoxy)-4-phenyl-5-oxazolyl]benzenesulfonamide as a white solid (0.4 g, 44%): mp 145–147° C. $^1$H NMR (CDCl$_3$) 300 MHz δ 7.88 (d, J=8.9 Hz, 2H) 7.70 (d, J=8.9 Hz, 2H) 7.6 (m, 2H) 7.36–7.5 (m, 6H) 7.0–7.1 (dt, J=6.4 Hz and J=2.2 Hz, 1H) 4.85 (bs, 2H) 3.7 (m, 4H) 3.05 (s, 3H) 2.0 (m, 4H). Anal. Calc'd. for $C_{27}H_{26}N_2O_6S$: C, 64.02; H, 5.17; N, 5.53. Found: C, 63.94; H, 5.17; N, 5.55.

EXAMPLE 6

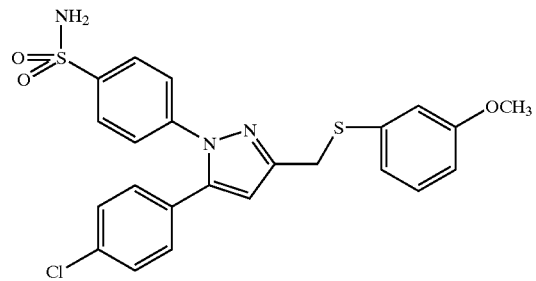

4-[5-(4-Chlorophenyl)-3-(3-methoxyphenyl)thiomethyl-1H pyrazol-1-yl]benzenesulfonamide Step 1. Preparation of methyl 4-(4-chlorophenyl)-2,4-dioxobutanoate.

Dimethyl oxalate (15.27 g, 0.129 mol), and 4'-chloroacetophenone (20.0 g, 0.129 mol) were added to methanol (300 mL). Sodium methoxide (25 wt % in methanol, 70 mL) was added dropwise over about 0.5 hour. The reaction was stirred at room temperature for 16 hours, whereupon the sodium salt of the butanoate precipitated from solution. The mixture was treated with 70 mL of conc. HCl and the white suspension was stirred vigorously at room temperature for 1 hour. The suspension was cooled to 0° C. and held for 0.5 hour. The solid was filtered, and the filter cake was washed with cold water (100 mL). After drying in vacuo, methyl 4-[4-(chloro)phenyl]-3-ketobutyrate was obtained (16.94 g, 54.4%) as the enol: $^1$H NMR (CDCl$_3$/300 MHz) δ 7.94 (d, J=8.66 Hz, 2H), 7.48 (d, J=8.66 Hz, 2H), 7.04 (s, 1H), 3.95 (s, 3H), 3.48 (s, 1H).

Step 2. Preparation of 4-[4-(aminosulfonyl)phenyl-5-(4 chlorophenyl)-1H-pyrazole-3-carboxylic acid.

4-Sulfonamidophenylhydrazine hydrochloride (1.45 g, 6.5 mmol) and methyl-4-(4-chlorophenyl)-2,4-dioxobutanoate from Step 1 (1.2 g, 5.0 mmol) were dissolved in 50 mL of methanol and heated to reflux for 20 hours. After cooling to room temperature, the reaction mixture was concentrated in vacuo and the residue dissolved in ethyl acetate, washed with water and brine, dried over anhydrous MgSO$_4$, filtered and re-concentrated to give a light brown solid. The crude solid was crystallized from methanol and water to provide 1.6 g, 85% of pure compound. This material was dissolved in 150 mL of methanol and treated with 75 mL of 3N NaOH. The solution was heated to reflux for 3 hours, and concentrated in vacuo. The residue was acidified with conc. HCl and was extracted into ethyl acetate. After removal of the ethyl acetate, the acid was isolated and dried to afford 1.4 g, (75%, mp 135° C.) that was used directly in the next step.

Step 3. Preparation of 4-[5-(4-chlorophenyl)-3-hydroxymethyl-1H pyrazol-1-yl]benzenesulfonamide.

4-[4-(Aminosulfonyl)phenyl-5-(4 chlorophenyl)-1H-pyrazole-3-carboxylic acid from Step 2 (3.8 g, 10 mmol) and tetrahydrofuran (100 mL) were stirred at room temperature during dropwise addition of 1.0 M borane-tetrahydrofuran complex (30 mL, 30 mmol). The mixture was held at reflux for 16 hours. The mixture was cooled and methanol was added dropwise until gas evolution ceased. Ethyl acetate (100 mL) was added and the mixture was washed with 1N hydrochloric acid, brine, sat. aq. sodium bicarbonate solution, and water, dried over magnesium sulfate, filtered and concentrated. The resultant alcohol was recrystallized from ethanol:water to yield a white solid (2.6 g, 71%): mp 192–194° C. $^1$H NMR (DMSO-d$_6$/300 MHz) δ 7.81 (d, J=8, 7 Hz, 2H), 7.46 (d, J=8.4 Hz, 2H), 7.42 (brs, 2H), 7.40 (d, J=8.7 Hz, 2H), 7.26 (d, J=8.4 Hz, 2H), 6.63 (s, 1H), 5.35 (t, J=8.0 Hz, 1H), 4.50 (d, J=8.0 Hz, 2H). Anal. Calc'd for C$_{16}$H$_{14}$N$_3$SO$_2$Cl: C, 52.82; C, 52.91; H, 3.88; H, 3.88; N, 11.55; N, 11.50.

Step 4. Preparation of 4-[5-(4-chlorophenyl)-3-(3-methoxyphenyl)thiomethyl-1H-pyrazol-1-yl]benzenesulfonamide.

4-[5-(4-Chlorophenyl)-3-hydroxymethyl-1H-pyrazol-1-yl]benzenesulfonamide from Step 3 (500 mg, 1.374 mmol) was dissolved in anhydrous THF (30 mL). Triethylamine (0.385 mL, 2.749 mmol) and methanesulfonyl chloride (0.16 mL, 2.062 mmol) were added sequentially, and the cloudy suspension was stirred at room temperature for 0.5 hour. The reaction was diluted with ethyl acetate (35 mL) and washed with aqueous HCl (1N, 50 mL). The organic solution was dried over anhydrous MgSO$_4$ and filtered, then the solvent was evaporated under reduced pressure to yield a crude oil. The oil was dissolved in anhydrous THF (10 mL). 3-Methoxythiophenol (0.205 mL, 1.649 mmol) was dissolved in anhydrous THF. Sodium hydride (95%, 42 mg, 1.649 mmol) was added, and the resulting frothy suspension was stirred at room temperature for 20 minutes, forming a clear, colorless solution. The solution of the mesylate prepared above was added, then the reaction was warmed to 40° C. and held for 16 hours. The reaction was cooled to room temperature then 1N HCl (30 mL) was added. After stirring an additional 0.5 hour, the system was extracted with ethyl acetate (2×40 mL). The combined organic solution was sequentially washed with 1 N HCl (40 mL), saturated aqueous NaHCO$_3$ (2×40 mL), 50% saturated NaCl (2×40 mL), and brine (40 mL), then dried over anhydrous MgSO$_4$ and filtered. The solvents were evaporated under reduced pressure to yield an oil. The oil was purified by flash chromatography over silica gel eluting with 40% ethyl acetate in hexane to yield 4-[5-(4-chlorophenyl)-3-(3-methoxyphenyl)thiomethyl-1H-pyrazol-1-yl]benzenesulfonamide (273 mg, 41%) as a foam: Mass Spectrum: 486 (MH+). High resolution mass spectrum Calc'd. for C$_{23}$H$_{20}$N$_3$O$_3$ClS$_2$: 486.0713. Found: 486.0757. Anal. Calc'd. for C$_{23}$H$_{20}$N$_3$O$_3$ClS$_2$: C, 56.84; H, 4.15; N, 8.65; Cl, 7.29; S, 13.19. Found: C, 56.56; H, 4.22; N, 8.61; Cl, 7.41; S, 13.00.

EXAMPLE 7

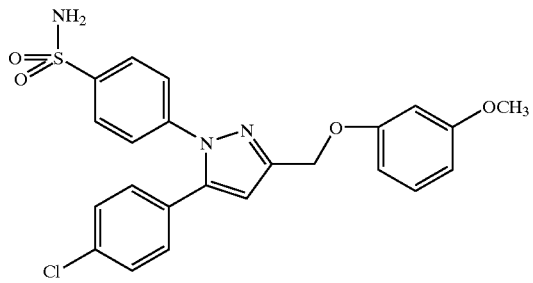

4-[5-(4-Chlorophenyl)-3-(3-methoxyphenyl)oxymethyl-1H-pyrazol-1-yl]benzenesulfonamide 4-[5-(4-Chlorophenyl)-3-(3-methoxyphenyl)oxymethyl-1H-pyrazol-1-yl]benzenesulfonamide was prepared from 4-[5-(4-chlorophenyl)-3-hydroxymethyl-1H-pyrazol-1-yl]benzenesulfonamide (prepared in Example 6, step 3) in 39% yield by the method outlined in Example 1, Step 4: Mass Spectrum: 470 (MH+). High resolution mass spectrum Calc'd. for C$_{23}$H$_{20}$N$_3$O$_4$ClS: 470.0979. Found: 470.0983. Anal. Calc'd. for C$_{23}$H$_{20}$N$_3$O$_4$ClS: C, 58.78; H, 4.29; N, 8.94; Cl, 7.54; S, 6.82. Found: C, 58.85; H, 4.29; N, 8.90; Cl, 7.63; S, 6.93.

EXAMPLE 8

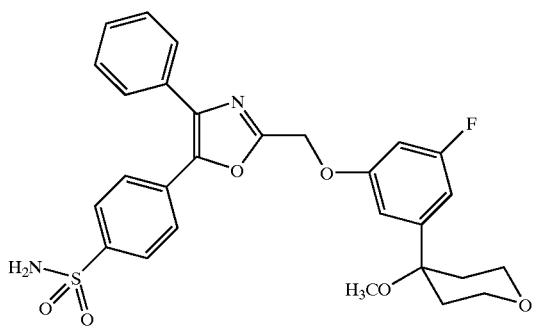

4-[2-[[3-Fluoro-5-(3,4,5,6-tetrahydro-4-methoxypyran-4-yl)phenoxy]methyl]-4-phenyloxazol-5-yl]benzenesulfonamide Step 1. Preparation of 2-bromo-2-[(4-aminosulfonyl)phenyl]-1-phenyl-ethanone.

Chlorosulphonic acid (100 mL) was cooled to 0° C. Deoxybenzoin (10 g, 51 mmol) was added, and the reaction was warmed from 0° C. to room temperature over 4 h. The solution was carefully poured into ice water, filtered, and the aqueous layer was extracted with three 250 mL portions of CH$_2$Cl$_2$. The combined organic extracts were washed once with brine (75 mL) and stirred over ice cold NH$_4$OH (125 mL) for 16 h. The CH$_2$Cl$_2$ layer was separated and washed consecutively with 1N HCl (2×75 mL), saturated aqueous NaHCO$_3$ (75 mL) and brine (75 mL), dried over Na$_2$SO$_4$, filtered, and concentrated. The crude material (4.23 g) was suspended in acetic acid (75 mL) and a solution of HBr in acetic acid (33 V % HBr in HOAc, 25 mL), and bromine (0.79 mL, 15.4 mmol) was added. After 0.25 h at room temperature, the reaction was complete by TLC, and the reaction was concentrated to remove the acetic acid. The residue was dissolved in ethyl acetate (250 mL) and NaHSO$_3$ (10%, 250 mL). The organics were washed with saturated aqueous bicarbonate (75 mL) and brine (75 mL), dried over Na$_2$SO$_4$, filtered, and concentrated yielding 2-bromo-2-[(4-aminosulfonyl)phenyl]-1-phenyl-ethanone which was used below without further purification.

Step 2. Preparation of 4-[2-hydroxymethyl-4-phenyloxazol-5-yl]benzenesulfonamide.

Glycolic acid monosodium salt (1.55 g, 15.8 mol) and 2-bromo-2-[(4-aminosulfonyl)phenyl]-1-phenylethanone (Step 1) were suspended in DMF (350 mL) and stirred at room temperature for 16 h. The reaction was concentrated. The resulting residue was combined with ammonium acetate (2.31 g, 30 mmol) and acetic acid (25 mL), and the mixture was heated to reflux for 3 h. The reaction was concentrated to dryness, and the residue was dissolved in ethyl acetate (250 mL), washed with water, saturated aqueous bicarbonate and brine, dried, filtered, and concentrated. The crude material was purified by flash column chromatography on silica gel, eluting with a gradient from 50% to 75% ethyl acetate in hexane, to yield 1.89 g (37%) of 4-[2-hydroxymethyl-4-phenyloxazol-5-yl]benzenesulfonamide: $^1$H NMR (acetone-d$_6$/300 MHz) δ 4.76 (m, 2H), 6.68 (s, 2H), 7.45 (m, 3H), 7.65 (m, 2H), 7.77 (d, 2H), J=6.8 Hz), 7.94 (d, 2H, J=8.7 Hz).

Step 3. Preparation of 4-[2-chloromethyl-4-phenyloxazol-5-yl]benzenesulfonamide.

A solution of 4-[2-hydroxymethyl-4-phenyloxazol-5-yl] benzenesulfonamide (Step 2) (1.0 g, 3 mmol) and triethylamine (0.61 g, 6 mmol) was stirred in tetrahydrofuran (100 mL) at 0° C. Lithium chloride (0.25 g, 6 mmol) was added, followed by the dropwise addition of methanesulfonyl chloride (0.38 g, 3.3 mmol). After stirring for 3 h from 0° C. to 25° C., ethyl acetate (100 mL) was added, and the mixture was washed with 1N hydrochloric acid, brine and water, dried over magnesium sulfate, filtered, and concentrated. The crude product was purified by flash column chromatography on silica gel eluting with a 1:1 mixture of ethyl acetate:hexanes. The appropriate fractions were concentrated to a clear oil which solidified upon standing to give 4-[2-chloromethyl-4-phenyloxazol-5-yl]benzenesulfonamide as a white solid which was used in the next step without further purification or characterization.

Step 3. Preparation of 4-[2-[[3-fluoro-5-(3,4,5,6-tetrahydro-4-methoxypyran-4-yl)phenoxy]methyl]-4-phenyloxazol-5-yl]benzenesulfonamide.

A mixture of 4-[2-chloromethyl-4-phenyloxazol-5-yl] benzenesulfonamide (Step 3) (0.5 g, 1.4 mmol), potassium carbonate (0.4 g, 2.8 mmol), dimethylformamide (20 mL), and 3-fluoro-5-(4-methoxy-3,4,5,6-tetrahydro-2H-pyran-4-yl)phenol [prepared as described in *J. Med Chem.*, 35, 2600–2609 (1992)] (0.3 g, 1.4 mmol) was stirred at room temperature, for 16 h. Water (20 mL) was added, and the mixture was extracted with ethyl acetate (4×30 mL) The combined organic layers were washed with brine, dried over magnesium sulfate and concentrated. The resulting crude product was purified by flash column chromatography on silica gel eluting with 50% ethyl acetate in hexanes to give 0.3 g (40%) of 4-[2-[[3-fluoro-5-(3,4,5,6-tetrahydro-4-methoxy-pyran-4-yl)phenoxy]methyl]-4-phenyl-oxazol-5-yl]benzenesulfonamide as a sticky white solid: m.p. 70–80° C. $^1$H NMR (CDCl$_3$/300 MHz) δ 7.92 (d, 2H, J=8.9 Hz), 7.77 (d, 2H, J=8.9 Hz), 7.62 (m, 2H), 7.43 (m, 3H), 6.94 (s, 1H), 6.78 (m, 2H) 5.24 (s, 2H), 4.82 (bs, 2H), 3.82 (m, 4H), 3.00 (s, 3H), 1.95 (m, 4H). Anal. calcd for C$_{28}$H$_{27}$FN$_2$O$_6$S: C, 62.44; H, 5.05; N, 5.20. Found: C, 62.50; H, 5.11; N, 5.24.

EXAMPLE 9

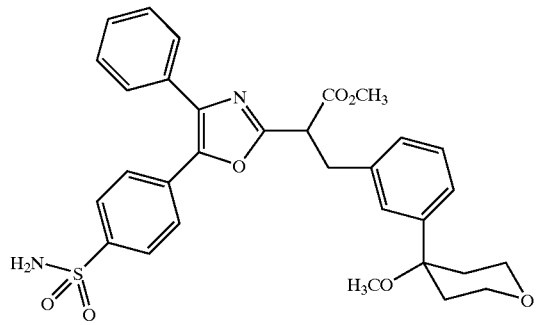

Methyl 5-[4-(aminosulfonyl)phenyl]-α-[[3-(3,4,5,6-tetrahydro-4-methoxypyran-4-yl)phenyl]methyl]-4-phenyloxazole-2-acetate Step 1. Preparation of 2-[(4-chlorosulfonyl)phenyl]-1-phenylethanone.

Deoxybenzoin (10 g, 0.051 mol) was added in portions to neat chlorosulfonic acid (50 mL) at −78° C. The reaction mixture was stirred at −78° C. for 2 h, then warmed to room temperature and for 1.5 h. The reaction mixture was cooled to −78° C. carefully poured onto crushed ice. The resulting solid was collected by filtration, washed with water, and dried to give 10.3 g (68%) of the desired sulfonyl chloride as a yellow solid. This crude material was used for the next reaction without further purification: HRMS: calcd for C$_{14}$H$_{11}$O$_3$SCl 295.0196, found 295.0205.

Step 2. Preparation of 2-[(4-aminosulfonyl)phenyl]-1-phenylethanone.

A solution of the sulfonyl chloride from Step 1 (9 g, 0.03 mol) in tetrahydrofuran (100 mL) was slowly added to ammonium hydroxide (100 mL) at 5° C. The reaction mixture was stirred for 1.5 h at 5° C. and for 30 minutes at room temperature. The resulting solid was collected by filtration, washed with excess water and hexane, then vacuum dried to give 3.47 g (41%) of the desired sulfonamide as a white solid: m.p. 259–261.5° C. $^1$H NMR (DMSO-d$_6$/300 MHz) δ 4.52 (s, 2H), 7.30 (s, 2H), 7.43 (bd, 2H, J=8.26 Hz), 7.54 (dd, 2H, J=7.56 Hz), 7.65 (dd, 1H, J=7.35 Hz), 7.75 (d, 2H, J=8.26 Hz), 8.04 (d, 2H, J=7.45 Hz). HRMS: calcd for C$_{14}$H$_{13}$NO$_3$S 276.0694, found 276.0709.

Step 3. Preparation of 2-bromo-2-[(4-aminosulfonyl)phenyl]-1-phenyl-ethanone.

The sulfonamide from Step 2 (5.0 g, 0.018 mol) was suspended in dichloroethane (50 mL), then a solution of 30% HBr in acetic acid (20 mL), acetic acid (70 mL) and bromine (1 mL) was added at room temperature. The reaction mixture was stirred for 40 minutes at room temperature and was concentrated in vacuo. Water (200 mL) was added to the resulting concentrated residue, and the mixture was extracted with ethyl acetate (2×250 mL) The combined ethyl acetate extracts were washed with 5% sodium bicarbonate (2×250 mL), and brine (2×250 mL), dried over magnesium sulfate, filtered and concentrated under reduced pressure. Methylene chloride (50 mL) was added to the concentrated residue and a solid precipitated. This solid was collected by filtration, washed with cold methylene chloride and air-dried to give 3.5 g (55%) of 2-bromo-2-[(4-aminosulfonyl)phenyl]-1-phenylethanone as a yellow solid: m.p. 153.6–155° C. $^1$H NMR (DMSO-$d_6$/300 MHz) δ 7.25 (s, 1H), 7.38 (s, 2H), 7.54 (dd, 2H, J=7.55 Hz), 7.62–7.74 (m, 3H), 7.82 (d, 2H, J=8.46 Hz), 8.07 (d, 2H, J=8.66 Hz). HRMS: calcd for $C_{14}H_{12}NO_3SBr$ 353.9800, found 353.9824.

Step 4. Preparation of benzyl methyl 2-[3-[(4-methoxy)tetrahydropyran-4-yl]phenylmethyl]malonate.

A solution of benzyl methyl malonate (0.88 g, 4.22 mmol) in 3 mL of anhydrous DMA was added to a suspension of sodium hydride (0.11 g, 4.45 mmol) in 2 mL of anhydrous DMA at 5° C., and the reaction mixture was stirred for 40 min at 5° C. Then 3-[(4-methoxy)tetrahydropyran-4-yl]-α-bromotoluene [prepared as described in U.S. Pat. No. 5,424,320] (1.21 g, 4.24 mmol) was dissolved in 6 mL of anhydrous DMA and added to this solution. The reaction mixture was stirred for 2 h at 5° C., and for 18 h at room temperature. The reaction mixture was quenched with water (100 mL). The aqueous solution was extracted with ethyl acetate (3×70 mL) The combined organic extracts were washed with brine (1×100 mL), dried over magnesium sulfate, filtered and concentrated. The concentrated residue was purified by flash column chromatography on silica gel, eluting with 20% ethyl acetate in hexane, to give 0.93 g (53%) of benzyl methyl 2-[3-[(4-methoxy)tetrahydropyran-4-yl]phenylmethyl]malonate as a clear oil: HRMS: calcd for $C_{24}H_{28}O_6$ 413.1964, found 413.1952.

Step 5. Preparation of monomethyl 2-[3-[(4-methoxy)tetrahydropyran-4-yl]phenylmethyl]malonate A solution of benzyl methyl 2-[3-[(4-methoxy)tetrahydropyran-4-yl]phenyl-methyl]malonate (0.3 g, 7.27 mmol) in 15 mL of ethyl acetate was combined with 10% palladium on activated carbon (0.17 g). The reaction mixture was stirred under 40 psi of hydrogen gas for 18 h at room temperature. The reaction mixture was filtered through Celite® and washed with excess ethyl acetate. The filtrate was concentrated and dried under vacuum to give 0.2 g (85%) of monomethyl 2-[3-[(4-methoxy)tetrahydropyran-4-yl]phenyl-methyl]malonate as a clear oil: HRMS: calcd for $C_{17}H_{22}O_6$ 323.1495, found 323.1473.

Step 6. Preparation of methyl 5-[4-(aminosulfonyl)phenyl]-α-[[3-(3,4,5,6-tetrahydro-4-methoxypyran-4-yl)phenyl]methyl]-4-phenyloxazole-2-acetate.

Solid NaOH (87 mg, 2.17 mmol) was added to a solution of the monomethyl 2-(3-[(4-methoxy)tetrahydropyran-4-yl]phenyl-methyl]malonate (Step 5) (0.7 g, 2.17 mmol) in ethanol (10 mL) and water (2 mL), and the mixture was stirred for 15 min at room temperature. The solvents were removed at reduced pressure. Several mL of absolute ethanol were added to the resulting residue, which was concentrated again at reduced pressure. This procedure was repeated three times until a white solid formed, which was dried under vacuum. The resulting carboxylic acid sodium salt was suspended in 2 mL of anhydrous DMF. A solution of 2-bromo-2-[(4-amino-sulfonyl)phenyl]-1-phenylethanone (Step 3) (0.77 g, 2.17 mmol) in anhydrous DMF (3 mL) was added at room temperature to the DMF solution of the sodium carboxylate. The reaction mixture was stirred for 18 h at room temperature, and the DMF was removed at reduced pressure. Ethyl acetate (150 mL) was added to the concentrated residue, and the mixture was filtered. The filtrate was concentrated and dried to give the desired crude α-acyloxy ketone. Acetic acid (5 mL) and ammonium acetate (1.5 g, 19.2 mmol) were added to this concentrated residue, and the mixture was heated at 100° C. for 3 h. The reaction mixture was cooled to room temperature, and the excess acetic acid was removed under vacuum. The resulting residue was partitioned between water (100 mL) and ethyl acetate (200 mL). The organic layer was separated, washed with saturated aqueous sodium bicarbonate (2×100 mL), saturated brine (1×100 mL), dried over magnesium sulfate, filtered and concentrated. The concentrated residue was purified by flash column chromatography on silica gel, eluting with 2:1 ethyl acetate in hexane, to give 0.24 g of a white solid which was recrystallized from methanol and water to give 0.13 g (19%) of methyl 5-[4-(aminosulfonyl)phenyl]-α-[[3-(3,4,5,6-tetrahydro-4-methoxypyran-4-yl)phenyl]-methyl]-4-phenyloxazole-2-acetate as a white solid: m.p. 88.7–94.9° C. $^1$H NMR (CDCl$_3$/300 MHz) δ 1.78–1.88 (m, 4H), 2.84 (s, 3H), 3.47–3.53 (m, 4H), 3.65–3.77 (m, 5H), 4.28 (dd, 1H, J=7.05 Hz), 5.00 (s, 2H), 7.16–7.32 (m, 4H), 7.36–7.40 (m, 3H), 7.54–7.58 (m, 2H), 7.68 (d, 2H, J=8.70 Hz), 7.88 (d, 2H, J=8.70 Hz). HRMS: calcd for $C_{31}H_{32}N_2O_7S$ 577.2008. Found 577.1961.

EXAMPLE 10

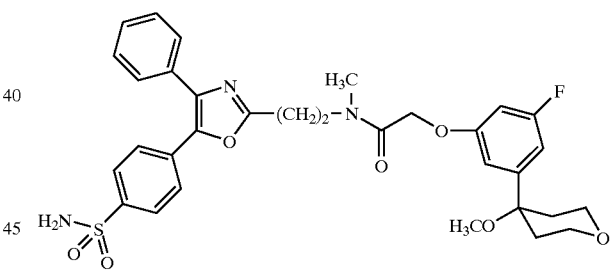

N-[2-[5-[4-(Aminosulfonyl)phenyl]-4-phenyloxazol-2-yl]ethyl]-2-[3-fluoro-5-(3,4,5,6-tetrahydro-4-methoxypyran-4-yl)phenoxy-N-methylacetamide

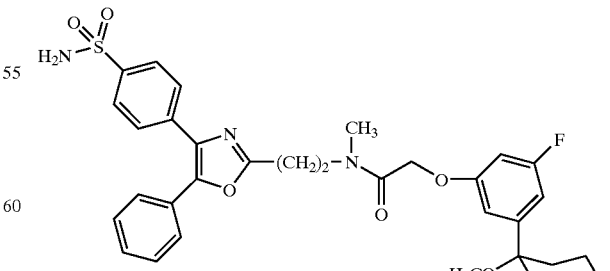

N-[2-[4-[4-(Aminosulfonyl)phenyl]-5-phenyloxazol-2-yl]ethyl]-2-[3-fluoro-5-(3,4,5,6-tetrahydro-4-methoxypyran-4-yl)phenoxy-N-methylacetamide Step 1. Preparation of ethyl 3-fluoro-5-(4-methoxy-3,4,5,6-tetrahydro-2-H-pyran-4-yl)phenoxyacetate.

A mixture of ethyl bromoacetate (0.5 g, 3 mmol), 3-fluoro-5-(4-methoxy-3,4,5,6-tetrahydro-2H-pyran-4-yl) phenol (Example 8, Step 4) (0.3 g, 1.3 mmol) and $K_2CO_3$ (0.11 g, 0.8 mmol) in dimethylformamide (5.0 mL) was stirred at room temperature for 16 h under an argon atmosphere. The reaction mixture was partitioned between 5% citric acid (25 mL) and EtOAc (25 mL). The organic phase was washed with water, dried ($Na_2SO_4$), filtered and concentrated. The resulting syrup was purified by flash column chromatography on silica gel, eluting with 25% EtOAc in hexane, to give 0.3 g (73%) of ethyl 3-fluoro-5-(4-methoxy-3,4,5,6-tetrahydro-2H-pyran-4-yl)phenoxyacetate as a colorless viscous liquid: $^1$H NMR (CDCl$_3$/300 MHz) δ 6.77 (d, 2H, J=10.5 Hz), 6.52 (d, 1H, J=10.5 Hz), 4.61 (s, 2H), 4.28 (q, 2H, J=6.9 Hz), 3.82 (m, 4H), 2.99 (s, 3H), 1.92 (m, 4H), 1.31 (t, 3H, J=6.9 Hz). FABMS m/z=313 (M+H). HRMS calcd for $C_{16}H_{22}FO_5$ 313.1451, found 313.1399.

Step 2. Preparation of 3-fluoro-5-(4-methoxy-3,4,5,6-tetrahydro-2H-pyran-4-yl)phenoxyacetic acid.

A solution of ethyl 3-fluoro-5-(4-methoxy-3,4,5,6-tetrahydro-2H-pyran-4-yl)phenoxyacetate (Step 1) (0.3 g, 1 mmol) in ethanolic LiOH (1M, 1.5 mL) was stirred at room temperature for 2 h. The reaction mixture was diluted with 5% citric acid (10 mL) and extracted with ether (2×15 mL). The ether extracts were combined and washed with water (2×20 mL), dried ($Na_2SO_4$), filtered, and concentrated under reduced pressure to give 0.26 g (95%) of 3-fluoro-5-(4-methoxy-3,4,5,6-tetrahydro-2H-pyran-4-yl)phenoxyacetic acid as a colorless viscous liquid: $^1$H NMR (CDCl$_3$/300 MHz) δ 6.78 (d, 2H, J=10.5 Hz), 6.50 (d, 1H, J=10.5 Hz), 4.68 (s, 2H), 3.82 (m, 4H), 2.99 (s, 3H), 1.92 (m, 4H); FABMS m/z=284 (M+H). HRMS calcd for $C_{14}H_{17}FO_5$ 283.0982, found 283.0993.

Step 3. Preparation of 4-[2-[2-(N-methyl-N-phenyl-methoxycarbonylamino)-ethyl]-4-phenyl-oxazol-5-yl]benzenesulfonamide and 4-[2-[2-(N-methyl-N-phenylmethoxycarbonylamino)ethyl]-5-phenyloxazol-4-yl]benzenesulfonamide.

A mixture of N-phenylmethoxycarbonyl-N-methyl-β-alanine (1.7 g, 7.2 mmol) and 2-bromo-2-[(4-aminosulfonyl)phenyl]-1-phenylethanone (Example 8, Step 1) (2.0 g, 5.65 mmol) in dimethylacetamide (5.00 mL) was treated with $K_2CO_3$ (0.54 g, 3.9 mmol) and 18-crown-6 (0.05 g) and stirred at room temperature for 16 h. After the removal of the solvent in vacuo, the residue was partitioned between cold water (25 mL) and EtOAc (50 mL). The organic phase was washed with water (2×25 mL), dried ($Na_2SO_4$), filtered, and concentrated under reduced pressure. The resulting substance was purified by flash column chromatography on silica gel, eluting with 30% EtOAc in hexane, to afford the desired α-acyloxyketone (2.2 g) as an amorphous substance. This benzoin ester (2.1 g) was dissolved in glacial acetic acid (20 mL), ammonium acetate (1.8 g, 23.4 mmol) was added, and the resulting mixture was heated at 90° C. under a nitrogen atmosphere for 2.5 h. After cooling and the removal of the solvent in vacuo, the residue was partitioned between water (50 mL) and EtOAc (75 mL). The organic phase was washed with water (2×25 mL) dried ($Na_2SO_4$), filtered, and concentrated under reduced pressure. The resulting material was purified by flash column chromatography on silica gel, eluting with 40% EtOAc in hexane, to provide 1.15 g (57%) of 4-[2-[2-(N-methyl-N-phenyl-methoxycarbonyl-amino)ethyl]-4-phenyl-oxazol-5-yl]benzenesulfonamide and 4-[2-[2-(N-methyl-N-phenylmethoxycarbonylamino)ethyl]-5-phenyloxazol-4-yl]benzenesulfonamide as a white amorphous material containing the two isomeric oxazole products: $^1$H NMR (CDCl$_3$/300 MHz) δ 7.85 (d, 2H, J=8.7 Hz), 7.67 (m, 2H), 7.54 (m, 2H), 7.42 (m, 3H), 7.28 (m, 5H), 5.08 (d, 2H, J=9.0 Hz), 4.9 (br, 2H), 3.8 (t, 2H, J=6.9 Hz), 3.17 (m, 2H), 2.99 & 2.94 (s, 3H:). FABMS m/z=492 (M+H). HRMS calcd for $C_{26}H_{25}N_3O_5S$ 492.1593, found 492.1581.

Step 4. Preparation of 4-[2-[2-(N-methylamino)ethyl]-4-phenyloxazol-5-yl]benzenesulfonamide and 4-[2-[2-(N-methylamino)ethyl]-5-phenyloxazol-4-yl]benzenesulfonamide.

A solution of 4-[2-[2-(N-methyl-N-phenylmethoxycarbonylamino)ethyl]-4-phenyloxazol-5-yl]benzenesulfonamide and 4-[2-[2-(N-methyl-N-phenyl-methoxycarbonylamino) ethyl]-5-phenyloxazol-4-yl]benzenesulfonamide (0.7 g, 1.4 mmol) from Step 3, in MeOH (15 mL) containing acetic acid (0.1 mL) was treated with 10% Pd on carbon (0.4 g) and stirred under an atmosphere of hydrogen at 50 psi at room temperature for 3 h. The catalyst was removed by filtration, the filtrate was concentrated under reduced pressure, and the resulting substance was purified by reverse-phase HPLC using a gradient of 5–70% CH$_3$CN in water to give 0.42 g of 4-[2-[2-(N-methylamino)ethyl]-4-phenyloxazol-5-yl] benzenesulfonamide and 4-[2-[2-(N-methylamino)ethyl]-5-phenyloxazol-4-yl]benzenesulfonamide trifluoroacetate salts as a white powder: $^1$H NMR (CD$_3$OD/300 MHz) δ 7.88 (d, 2H, J=8.7 Hz), 7.74 (d, 2H, J=8.7 Hz), 7.6 (m, 2H), 7.43 (m, 3H), 3.55 (t, 2H, J=6.6 Hz), 3.36 (t, 2H, J=6.6 Hz), 2.82 (s, 3H); FABMS m/z=358 (M+H).

Step 5. Preparation of N-[2-[5-[4-(aminosulfonyl)phenyl]-4-phenyloxazol-2-yl]ethyl]-2-[3-fluoro-5-(3,4,5,6-tetrahydro-4-methoxypyran-4-yl)phenoxy-N-methylacetamide and N-[2-[4-[4-(aminosulfonyl)phenyl]-5-phenyloxazol-2-yl] ethyl]-2-[3-fluoro-5-(3,4,5,6-tetrahydro-4-methoxypyran-4-yl)phenoxy-N-methylacetamide.

To a solution of 3-fluoro-5-(4-methoxy-3,4,5,6-tetrahydro-2H-pyran-4-yl)phenoxyacetic acid (0.27 g, 0.95 mmol) from Step 2 in dimethylacetamide (2.00 mL) and dichloromethane (3.00 mL), was added HOBt (0.22 g, 1.45 mmol) and EDC (0.19 g, 1 mmol), and the resulting mixture was stirred at 0° C. for 1 h. This reaction mixture was treated with a solution of the free amines generated by the addition of N-methylmorpholine (0.1 mL) to a solution of the 4-[2-[2-(N-methylamino)ethyl]-4-phenyloxazol-5-yl]benzenesulfonamide and 4-[2-[2-(N-methylamino)ethyl]-5-phenyloxazol-4-yl]benzenesulfonamide trifluoroacetates (0.36 g, 0.8 mmol) from Step 4 in dimethylacetamide (1.0 mL) at 0° C. The resulting mixture was warmed to room temperature in 16 h. The reaction mixture was diluted with dichloromethane (20 mL), and washed sequentially with 5% citric acid, (2×10 mL), saturated NaHCO$_3$ (2×10 mL), water, dried (Na$_2$SO$_4$), and filtered. After the removal of the solvent under reduced pressure, the residue was purified by flash column chromatography on silica gel, eluting with 1% MeOH in EtOAc, to afford the desired product as a white amorphous (0.25 g, 52%) substance. This material was further purified by reverse-phase HPLC using a gradient of 5–90% CH$_3$CN. The appropriate fractions were combined and freeze-dried to afford an isomeric mixture of N-[2-[5-[4-(aminosulfonyl)phenyl]-4-phenyloxazol-2-yl]ethyl]-2-[3-fluoro-5-(3,4,5,6-tetrahydro-4-methoxypyran-4-yl) phenoxy-N-methylacetamide and N-[2-[4-[4-(aminosulfonyl)phenyl]-5-phenyloxazol-2-yl]ethyl]-2-[3-fluoro-5-(3,4,5,6-tetrahydro-4-methoxypyran-4-yl)phenoxy-N-methylacetamide as a white powder: $^1$H NMR (CD$_3$OD/300

MHz) δ 7.85 (m, 2H), 7.71 & 7.64 (d, 2H, J=8.7 Hz), 7.54 (m, 1H), 7.4–7.3 (m, 4H), 6.82–6.48 (m, 3H), 4.82 & 4.76 (s, 2H), 3.78 (m, 2H), 3.75 (m, 4H), 3.17 (m, 2H), 3.16 & 3.07 (s, 3H), 2.96 & 2.89 (s, 3H), 1.92–1.83 (m, 4H). FABMS m/z=624 (M+H). HRMS calcd for $C_{32}H_{35}N_3O_7FS$ 624.2180, found 624.2177.

EXAMPLE 11

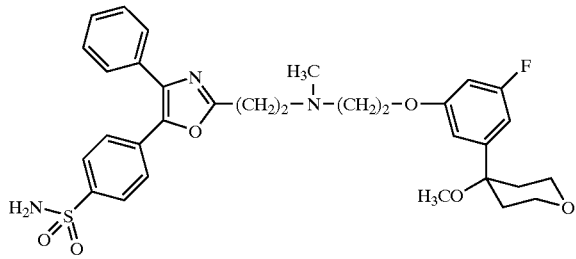

4-[2-[[2-[3-Fluoro-5-(3,4,5,6-tetrahydro-4-methoxy-pyran-4-yl)phenoxy]ethyl]-N-methylaminoethyl]-4-phenyloxazol-5-yl]benzenesulfonamide mmol) in dry THF (4.00 mL) was combined with LiAlH$_4$ (0.016 g, 0.4 mmol) and stirred at room temperature for 16 h under argon. The reaction mixture was cooled, and cold EtOAc (15 mL) was added. After stirring for 15 min, 0.5 N NaOH (15 mL) was added and the reaction mixture was filtered through Celite®. The organic phase was washed with cold 0.5 N NaOH (10 mL), water, dried (Na$_2$SO$_4$), filtered, and concentrated under reduced pressure. The resulting material was purified by reverse-phase HPLC using a gradient of 5–90% CH$_3$CN in water. The appropriate fractions were combined and freeze-dried to provide an isomeric mixture of 4-[2-[[2-[3-fluoro-5-(3,4,5,6-tetrahydro-4-methoxy-pyran-4-yl)phenoxy]ethyl]-N-methylaminoethyl]-4-phenyloxazol-5-yl]-benzenesulfonamide and 4-[2-[[2-[3-fluoro-5-(3,4,5,6-tetrahydro-4-methoxy-pyran-4-yl)phenoxy]ethyl]-N-methylaminoethyl]-5-phenyloxazol-4-yl]benzenesulfonamide as trifluoroacetate salts: $^1$H NMR (CD$_3$OD/300 MHz) δ 7.88 (d, 2H, J=8.7 Hz), 7.71 (dd, 2H, J=8.7, 2.4 Hz), 7.57 (m, 2H), 7.42 (m, 3H), 6.83 (m, 2H), 6.65 (m, 1H), 4.46 & 4.38 (t, 2H J=6.0 Hz), 3.79–3.62 (m, 8H), 3.51 & 3.41 (t, 2H, J=6.6 Hz), 3.12, 2.96 & 2.93 (s, 6H), 1.88 (m, 4H). FABMS m/z=610 (M+H). HRMS calcd for $C_{32}H_{37}N_3O_6FS$ 610.2387, found 610.2373.

EXAMPLE 12

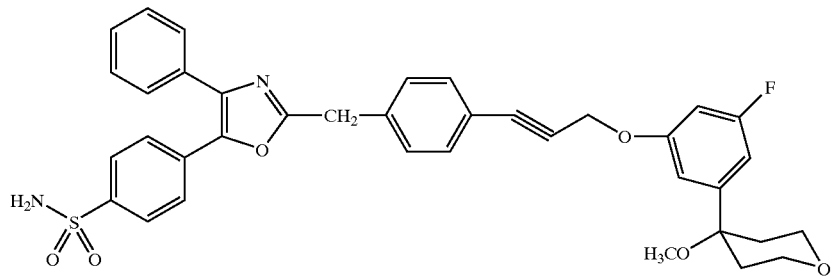

4-[2-[[4-[3-[3-Fluoro-5-(3,4,5,6-tetrahydro-4-methoxypyran-4-yl)phenoxy]-1-propynyl]phenyl]methyl]-4-phenyloxazol-5-yl]benzenesulfonamide Step 1. Preparation of 4-[[2-(4-iodophenyl)methyl]-4-phenyloxazol-5-yl]benzenesulfonamide.

A mixture of 2-bromo-2-[(4-aminosulfonyl)phenyl]-1-phenylethanone (Example 8, Step 1) (2.0 g, 5.65 mmol) and 4-iodophenylacetic acid (1.8 g, 6.9 mmol) in dimethylacetamide (6.0 mL) was treated with potassium carbonate (0.57 g, 4.13 mmol) and 18-crown-6 (0.06 g) and stirred at room temperature for 4 h. The reaction mixture was diluted with cold water (50 mL) and extracted with ethyl acetate (3×30 mL). The combined organic phases were washed with water (2×25 mL), dried (Na$_2$SO$_4$), filtered, and concentrated under reduced pressure. The resulting material was purified by flash chromatography on silica gel, eluting with 40% EtOAc in hexane, to give the desired α-acyloxy ketone as an amorphous substance, which was used in the next reaction without further purification: $^1$H NMR (CDCl$_3$/300 MHz) δ 7.86 (m, 4H), 7.63 (d, 2H, J=8.4 Hz), 7.59 (m, 3H), 7.41 (t, 2H, J=7.8 Hz), 7.03 (d, 2H, J=8.4 Hz), 6.89 (s, 1H), 4.82 (s, 2H), 3.73 (q, 2H, J=5.1 Hz). FABMS m/z=536 (M+H$^+$). HRMS: calcd for $C_{22}H_{19}NO_5SI$ 536.0029, found 536.0023.

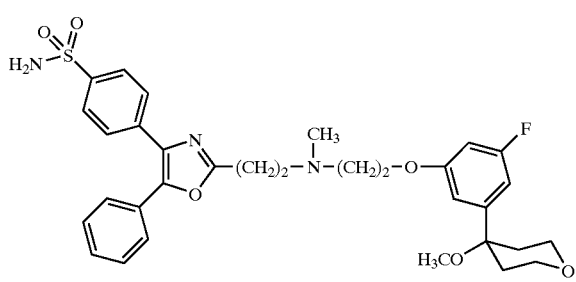

4-[2-[[2-[3-Fluoro-5-(3,4,5,6-tetrahydro-4-methoxy-pyran-4-yl)phenoxy]ethyl]-N-methylaminoethyl]-5-phenyloxazol-4-yl]benzenesulfonamide A solution of N-[2-[5-[4-(aminosulfonyl)phenyl]-4-phenyloxazol-2-yl]ethyl]-2-[3-fluoro-5-(3,4,5,6-tetrahydro-4-methoxypyran-4-yl)phenoxy-N-methylacetamide and N-[2-[4-[4-(aminosulfonyl)phenyl]-5-phenyloxazol-2-yl]ethyl]-2-[3-fluoro-5-(3,4,5,6-tetrahydro-4-methoxypyran-4-yl)phenoxy-N-methylacetamide (Example 10) (0.1 g, 0.16

A mixture of this α-acyloxy ketone (2.2 g, 4.1 mmol), and ammonium acetate (1.3 g, 16.9 mmol) in acetic acid (15.0 mL) was heated at 100° C. under a nitrogen atmosphere for 2.5 h. The reaction mixture was concentrated in vacuo, and the residue was partitioned between water (50 mL) and EtOAc (50 mL). The organic phase was washed with water (2×30 mL), dried ($Na_2SO_4$), filtered, and concentrated under reduced pressure. The resulting solid was triturated with methanol, cooled and filtered to give 1.1 g (52%) of 4-[[2-(4-iodophenyl)methyl]-4-phenyloxazol-5-yl]benzene-sulfonamide as a pale yellow powder: m.p. 198–201° C. $^1$H NMR ($CDCl_3$/300 MHz) δ 7.86 (d, 2H, J=8.7 Hz), 7.7 (dd, 4H), 7.59 (m, 2H), 7.41 (m, 3H), 7.15 (d, 2H, J=8.1 Hz), 4.81 (s, 2H), 4.16 (s, 2H); FABMS m/z=517 (M+H$^+$); HRMS calcd for $C_{22}H_{18}N_2O_3S_1I_1$ 517.0083, found 517.0063.

concentrated under reduced pressure. The resulting substance was purified by flash column chromatography on silica gel, eluting with 40% EtOAc in hexane, to afford 0.38 g (60%) of 4-[2-[[4-[3-[3-fluoro-5-(3,4,5,6-tetrahydro-4-methoxypyran-4-yl)phenoxy]-1-propynyl]phenyl]-methyl]-4-phenyloxazol-5-yl]benzenesulfonamide as a pale yellow amorphous material: m.p. 86–100° C. $^1$H NMR ($CDCl_3$/300 MHz) δ 7.85 (d, 2H, J=8.7 Hz), 7.65 (d, 2H, J=8.7 Hz), 7.55 (m, 1H), 7.42–7.2 (m, 8H), 6.82 (br s, 1H), 6.75–6.6 (m, 2H), 4.91 (s, 2H), 4.86 (s, 2H), 4.21 (s, 2H), 3.79 (m, 4H), 2.98 (s, 3H), 2.1–1.85 (m, 4H). FABMS m/z=653 (M+H). HRMS calcd for $C_{35}H_{34}N_2O_6FS$ 653.2122, found 653.2133.

EXAMPLE 13

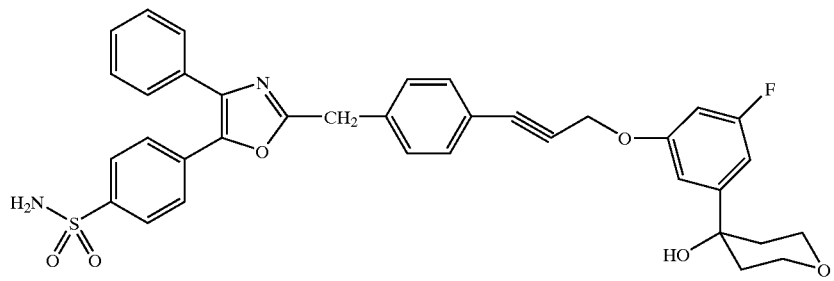

4-[2-[[4-[3-[3-Fluoro-5-(3,4,5,6-tetrahydro-4-hydroxypyran-4-yl)phenoxy]-1-propynyl]-phenyl]methyl]-4-phenyloxazol-5-yl]benzenesulfonamide Step 1. Preparation of 3-fluoro-5-(4-hydroxy-3,4,5,6-tetrahydro-2H-pyran-4-yl)phenylpropynyl ether.

To a solution of 3-fluoro-5-(4-hydroxy-3,4,5,6-tetrahydro-2H-pyran-4-yl)-phenol [prepared as described in *J. Med Chem.*, 35, 2600–2609 (1992)] (0.8 g, 3.8 mmol) in dimethylacetamide (2.00 mL), was added propargyl bromide (2.5 mL, 80% solution in toluene), $K_2CO_3$ (0.3 g, 2.2 mmol), and 18-crown-6 (0.03 g), and the resulting mixture was heated at 80° C. for 24 h under a nitrogen atmosphere. The reaction mixture was diluted with cold water (50 mL) and extracted with EtOAc (2×25 mL). The organic extracts were combined, washed with water (2×20 mL), dried ($Na_2SO_4$), filtered, and concentrated under reduced pressure. The residual brown liquid was purified by flash column chromatography on silica gel, eluting with 60% EtOAc in hexane, to afford 0.5 g (53%) of 3-fluoro-5-(4-hydroxy-3,4,5,6-tetrahydro-2H-pyran-4-yl)phenylpropynyl ether, which crystallized from $CH_2Cl_2$/hexane as a light brown powder: m.p. 120–122° C. $^1$H NMR ($CDCl_3$/300 MHz) δ 6.9 (d, H, J=1.5 Hz), 6.64 (d, 1H, J=9.9 Hz), 6.84 (d, 1H, J=9.9 Hz), 4.69 (d, 2H, J=2.4 Hz), 3.88 (m, 4H), 2.55 (t, 1H, J=2.4 Hz), 2.14 (m, 2H), 1.66 (m, 2H). FABMS m/z=251 (M+H). HRMS calcd for $C_{14}H_{16}FO_3$ 251.1083, found 251.1053.

Step 2. Preparation of 4-[2-[[4-[3-[3-fluoro-5-(3,4,5,6-tetrahydro-4-hydroxypyran-4-yl)phenoxy]-1-propynyl]phenyl]methyl]-4-phenyloxazol-5-yl]benzene-sulfonamide.

To a solution of 4-[[2-(4-iodophenyl)methyl]-4-phenyloxazol-5-yl]benzenesulfonamide (Example 12, Step 1) (0.35 g, 0.68 mmol) and 3-fluoro-5-(4-hydroxy-3,4,5,6-tetra-hydro-2H-pyran-4-yl)phenylpropynyl ether (Step 1) (0.185 g, 0.78 mmol) in dimethylformamide (2.0 mL) containing triethy- Step 2. Preparation of 3-fluoro-5-(4-methoxy-3,4,5,6-tetrahydro-2H-pyran-4-yl)phenylpropynyl ether.

A mixture of propargyl bromide (0.9 g, 7.6 mmol, 80% in toluene) and 3-fluoro-5-(4-methoxy-3,4,5,6-tetrahydro-2H-pyran-4-yl)phenol (Example 8, Step 4) (0.5 g, 2.2 mmol) in dimethylacetamide (5 mL) was stirred in the presence of $K_2CO_3$ (0.17 g, 1.2 mmol) and 18-crown-6 (0.02 g) for 16 h at room temperature. After the removal of the solvent in vacuo, the residue was partitioned between EtOAc (30 mL) and water (30 mL). The organic phase was washed with water, dried ($Na_2SO_4$), filtered, and concentrated. The residue was purified by flash column chromatography on silica gel, eluting with 25% EtOAc in hexane, to give 0.35 g (64%) of 3-fluoro-5-(4-methoxy-3,4,5,6-tetrahydro-2H-pyran-4-yl)phenylpropynyl ether as a pale yellow viscous liquid, which solidified upon drying: m.p. 75–77° C. $^1$H NMR ($CDCl_3$/300 MHz) δ 6.81 (d, 1H, J=1.5 Hz), 6.75 (m, 1H), 6.62 (m 1H), 4.69 (d, 2H, J=2.4 Hz), 3.82 (m, 4H), 3.0 (s, 3H), 2.55 (t, 1H, J=4.5 Hz), 2.1–1.8 (m, 4H). FABMS m/z=271 (M+Li). HRMS calcd for $C_{15}H_{18}FO_3Li$ 271.1322, found 271.1317.

Step 3. Preparation of 4-[2-[[4-[3-[3-fluoro-5-(3,4,5,6-tetrahydro-4-methoxypyran-4-yl)phenoxy]-1-propynyl]phenyl]methyl]-4-phenyloxazol-5-yl]benzene-sulfonamide.

A solution of 4-[[2-(4-iodophenyl)methyl]-4-phenyloxazol-5-yl]benzene-sulfonamide (Step 1) (0.5 g, 0.97 mmol) and 3-fluoro-5-(4-methoxy-3,4,5,6-tetrahydro-2H-pyran-4-yl)phenylpropynyl ether (Step 2) (0.28 g, 1.1 mmol) in dimethylformamide (2.00 mL) containing triethyl amine (0.16 mL, 1.14 mmol), was treated with $PdCl_2(PPh_3)_2$ (0.1 g), and CuI (0.02 g) and stirred at room temperature for 4 h, under an argon atmosphere. The reaction mixture was partitioned between 5% citric acid (20 mL) and EtOAc (50 mL). The organic phase was washed with 5% citric acid (2×15 mL), water (2×15 mL), dried ($Na_2SO_4$), filtered, and lamine (0.15 mL, 1.1 mmol), PdCl$_2$(PPh$_3$)$_2$ (0.1 g) and CuI (0.02 g) were added, and the resulting mixture was stirred at room temperature for 3 h, under an argon atmosphere. The reaction mixture was partitioned between 5% citric acid (20 mL) and EtOAc (50 mL). The organic phase was washed with 5% citric acid (2×15 mL), water (2×15 mL), dried (Na$_2$SO$_4$), filtered, and concentrated under reduced pressure. The resulting substance was purified by flash column chromatography on silica gel, eluting with 60% EtOAc in hexane, to afford 0.25 g (47%) of 4-[2-[[4-[3-[3-fluoro-5-(3,4,5,6-tetrahydro-4-hydroxypyran-4-yl)-phenoxy]-1-propynyl]phenyl]methyl]-4-phenyloxazol-5-yl]benzenesulfonamide as a pale yellow amorphous material: $^1$H NMR (CDCl$_3$/300 MHz) δ 7.85 (d, 2H, J=8.4 Hz), 7.66 (d, 2H, J=8.4 Hz), 7.58 (m, 2H), 7.44–7.33 (m, 7H), 6.95 (br, 1H), 6.82 (d, 1H, J=10 Hz), 6.64 (d, 1H, J=10 Hz), 4.91 (s, 2H), 4.83 (s, 2H), 4.21 (s, 2H), 3.88 (m, 4H), 2.15 (m, 2H), 1.6 (m, 2H). FABMS m/z=639 (M+H) HRMS calcd for C$_{36}$H$_{32}$N$_2$FO$_6$S 639.1965, found 639.1954.

EXAMPLE 14

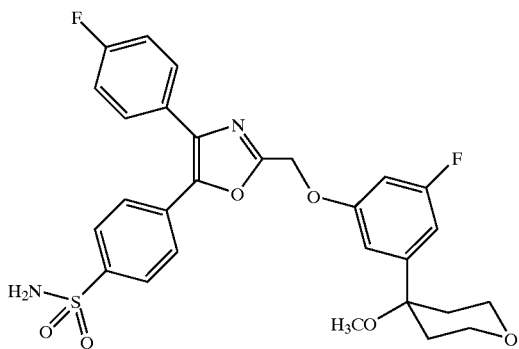

4-[2-[[3-Fluoro-5-(3,4,5,6-tetrahydro-4-methoxypyran-4-yl)phenoxy]methyl]-4-(4-fluorophenyl)oxazol-5-yl]benzenesulfonamide Step 1. Preparation of 2-[(4-Aminosulfonyl)phenyl]-1-(p-fluorophenyl)-ethanone.

Neat 2-(phenyl)-1-(p-fluorophenyl)ethanone (6.10 g, 28.54 mmol) was cooled to −78° C. in a dry ice methanol bath. Chlorosulfonic acid (15.0 mL) was added, and the solution was warmed to room temperature over 1 h. The solution was stirred for 2 h and poured directly into ice (500 mL in 1000 mL Erlenmeyer flask). The resulting heterogeneous aqueous solution was extracted with ethyl acetate (2×300 mL). The ethyl acetate layers were combined, extracted with water (1×100 mL) and mixed with ammonium hydroxide solution (50 mL) for 1 h. The ethyl acetate was collected, extracted with 1N HCl (2×200 mL), brine (1×200 mL), and dried over sodium sulfate. The solvent was removed to a volume of 50 mL and crystals formed. The crystals were kept at room temperature for 4 h and collected by vacuum filtration to give 3.1 g (37%) of 2-[(4-aminosulfonyl)phenyl]-1-(p-fluoro-phenyl)ethanone: m.p. 198–204° C. $^1$H NMR (CD$_3$OD/300 MHz) δ 4.46 (s, 2H), 7.23 (t, 2H, J=8.8 Hz), 7.43 (d, 2H, J=8.5 Hz), 7.85 (d, 2H, J=8.5 Hz), 8.10–8.20 (m, 2H). FABMS m/z=294 (M+H$^+$). HRMS calcd for C$_{14}$H$_{13}$FNO$_3$S 294.0600. Found 294.0583.

Step 2. Preparation of 2-[(4-aminosulfonyl)phenyl]-2-bromo-1-(p-fluoro-phenyl)ethanone.

To a solution of 2-[(4-aminosulfonyl)phenyl]-1-(p-fluorophenyl)ethanone (Step 1) (2.93 g, 10.00 mmol) in acetic acid (25 mL) at room temperature was added 33% HBr in acetic acid (5.0 mL), followed by bromine (1.59 g, 10.00 mmol), and the solution was stirred at room temperature for 1 h. The acetic acid was removed at reduced pressure, and the resulting yellow liquid was poured into ethyl acetate (100 mL). This solution was washed with saturated sodium bicarbonate (2×100 mL), followed by brine (100 mL). The ethyl acetate layer was dried over anhydrous sodium sulfate, filtered, and the solvent was removed at reduced pressure to give 3.21 g (86%) of 2-[(4-aminosulfonyl)phenyl]-2-bromo-1-(p-fluorophenyl)ethanone as a gummy foam: $^1$H NMR (CDCl$_3$/300 MHz) δ 5.05 (bs, 2H), 6.30 (s, 1H), 7.16 (t, 2H, J=8.6 Hz), 7.67 (d, 2H, J=8.5 Hz), 7.92 (d, 2H, J=8.5 Hz), 8.02–8.07 (m, 2H). FABMS m/z=389 (M+NH$_3$$^+$). HRMS calcd for C$_{14}$H$_{12}$BrFNO$_3$S 371.9705. Found 371.9721.

Step 3. Preparation of 4-[2-[[3-fluoro-5-(3,4,5,6-tetrahydro-4-methoxypyran-4-yl)phenoxy]methyl]-4-(4-fluorophenyl)oxazol-5-yl]benzenesulfonamide.

A mixture of 2-[(4-aminosulfonyl)phenyl]-2-bromo-1-(p-fluorophenyl)-ethanone (Step 2) (513 mg, 1.37 mmol) and the sodium salt of 3-fluoro-5-(4-methoxy-3,4,5,6-tetrahydro-2H-pyran-4-yl)phenoxyacetic acid (Example 10, Step 2) (419 mg, 1.37 mmol) were combined in dimethylformamide (3.0 mL) and stirred at room temperature for 1 h. The solvent was removed at reduced pressure, and the residue taken up in ethyl acetate (20 mL). This solution was washed with saturated aqueous sodium chloride (2×10 mL), saturated sodium bicarbonate (2×20 mL), and aqueous sodium chloride (2×10 mL). The ethyl acetate solution was dried over sodium sulfate, and the solvent was removed at reduced pressure. The resulting residue was purified by flash column chromatography on silica gel to give 419 mg (62%) of the desired α-acyloxyketone as a white foam: m.p. 78–81.° C. $^1$H NMR (CDCl$_3$/300 MHz) δ 1.91–1.98 (m, 4H), 2.96 (s, 3H), 3.80–3.83 (m, 4H), 4.83 (ab, 2H, J$_{ab}$=16.7 Hz, ΔV=18.4 Hz), 4.93 (bs, 2H), 6.59 (dt, 1H, J=10.0 Hz, J=2.2 Hz), 6.98 (s, 1H), 7.13 (m, 2H), 7.59 (d, 2H, J=8.5 Hz), 7.89–8.00 (m, 4H). FABMS m/z=582 (M+Li$^+$). HRMS calcd for C$_{28}$H$_{28}$F$_2$NO$_8$S 576.1504. Found 576.1507. This benzoin ester (180 mg, 0.31 mmol) and ammonium acetate (180 mg, 2.5 mmol) was heated at reflux in acetic acid (5 mL) for 30 min, and the solvent was removed at reduced pressure. The resulting residue was purified by flash column chromatography on silica gel to give 65 mg (37%) of 4-[2-[[3-fluoro-5-(3,4,5,6-tetrahydro-4-methoxypyran-4-yl)phenoxy]methyl]-4-(4-fluoro-phenyl)oxazol-5-yl]benzenesulfonamide as a white foam: m.p. 70–72° C. $^1$H NMR (CDCl$_3$/300 MHz) δ 1.85–2.01 (m, 4H), 2.98 (s, 3H), 3.80–3.83 (m, 4H), 4.82 (bs, 2H), 5.22 (s, 2H), 6.70–6.80 (m, 2H), 6.92 (m, 1H), 7.04–7.18 (m, 2H), 7.58–7.64 (m, 2H), 7.74 (d, 2H, J=8.7 Hz), 9.92 (d, 2H, J=8.7 Hz). FABMS: m/z=563 (M+Li). HRMS calcd for C$_{28}$H$_{27}$F$_2$N$_2$O$_6$S 557.1558. Found 557.1538.

EXAMPLE 15

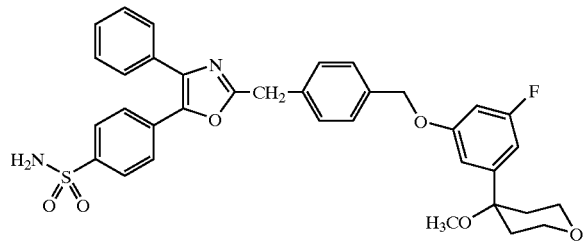

4-[2-[4-[[3-Fluoro-5-(3,4,5,6-tetrahydro-4-methoxy-pyran-4-yl)phenoxy]methyl]phenylmethyl]-4-phenyloxazol-5-yl]benzenesulfonamide Step 1. Preparation of methyl 4-[3-fluoro-5-(4-methoxy-3,4,5,6-tetrahydro-2H-pyran-4-yl)phenoxymethyl]benzoate.

A mixture of 3-fluoro-5-(4-methoxy-3,4,5,6-tetrahydro-2H-pyran-4-yl)phenol (Example 8, Step 4) (1.5 g, 6.6 mmol), methyl 4-(bromomethyl)benzoate (1.7 g, 7.4 mmol), $K_2CO_3$ (0.6 g, 4.3 mmol), 18-crown-6 (0.05 g) and KI (0.05 g) in dimethylacetamide (5.00 mL) was stirred at room temperature for 16 h, and at 80° C. for 2 h. The reaction mixture was poured into cold water (100 mL) and extracted with EtOAc (2×25 mL). The combined organic extracts were washed with water (2×25 mL), dried ($Na_2SO_4$), filtered, and concentrated under reduced pressure. The resulting residue was purified by flash column chromatography on silica gel, eluting with 20% EtOAc in hexane, to furnish 2.2 g (88%) of methyl 4-[3-fluoro-5-(4-methoxy-3,4,5,6-tetrahydro-2H-pyran-4-yl)phenoxymethyl]benzoate as a white solid: m.p. 88–89° C. $^1$H NMR ($CDCl_3$/300 Hz) δ 8.07 (d, 2H, J=7.8 Hz), 7.5 (d, 2H, J=7.8 Hz), 6.81 (s, 1H), 6.72 (d, 1H, J=9.9 Hz), 6.6 (d, 1H, J=9.9 Hz), 5.12 (s, 2H), 3.93 (s, 3H), 3.82 (m, 4H), 2.97 (s, 3H), 1.92 (m, 4H). FABMS m/z 375 (M+H).

Step 2. Preparation of 4-[3-fluoro-5-(4-methoxy-3,4,5,6-tetrahydro-2H-pyran-4-yl)phenoxymethyl]benzoic acid.

A solution of methyl 4-[3-fluoro-5-(4-methoxy-3,4,5,6-tetrahydro-2H-pyran-4-yl)phenoxymethyl]benzoate (Step 1) (1.9 g, 5.1 mmol) in THF (5.0 mL) was treated with methanolic 1M LiOH (8.0 mL) and stirred at room temperature for 2 h. The reaction mixture was acidified with 5% citric acid and extracted with EtOAc (2×25 mL). The organic extracts were combined and washed with water (2×25 mL), dried ($Na_2SO_4$), filtered, and concentrated to give the corresponding acid (1.7 g, 93%) as a white powder. Crystallization from EtOAc/hexane provided an analytically pure sample of 4-[3-fluoro-5-(4-methoxy-3,4,5,6-tetrahydro-2H-pyran-4-yl)phenoxymethyl]benzoic acid: m.p. 184–186° C. $^1$H NMR ($CDCl_3$/300 MHz) δ 8.14 (d, 2H, J=8.4 Hz), 7.54 (d, 2H, J=8.4 Hz), 6.82 (s, 1H), 6.75 (m, 1H), 6.62 (m, 1H), 5.14 (s, 2H), 3.83 (m, 4H), 2.98 (s, 3H), 1.93 (m 4H). FABMS m/z=360 (M+). HRMS calcd for $C_{20}H_{21}FO_5$ 360.1373, found 360.1372.

Step 3. Preparation of 4-[2-[4-[[3-fluoro-5-(3,4,5,6-tetrahydro-4-methoxypyran-4-yl)phenoxy]methyl]phenylmethyl]-4-phenyloxazol-5-yl]benzenesulfonamide.

A solution of 4-[3-fluoro-5-(4-methoxy-3,4,5,6-tetrahydro-2H-pyran-4-yl)phenoxymethyl]benzoic acid (Step 2) (0.6 g, 1.67 mmol) and 2-bromo-2-[(4-aminosulfonyl)phenyl]-1-phenyl-ethanone (0.5 g, 1.4 mmol) in dimethylacetamide (3.00 mL) was treated with $K_2CO_3$ (0.17 g, 1.23 mmol) and 18-crown-6 (0.02 g), and the resulting mixture was stirred at room temperature for 2.5 h. The reaction mixture was poured into cold water (50 mL) and extracted with EtOAc (3×25 mL). The organic extracts were combined and washed with water (2×25 mL), dried ($Na_2SO_4$), filtered and concentrated under reduced pressure to afford 0.9 g of the desired benzoin ester as an amorphous substance which was used in the next step without further purification: FABMS m/z=634 (M+H). HRMS calcd for $C_{34}H_{33}FNSO_8$ 634.1911, found 634.1939. This benzoin ester (0.8 g, 1.3 mmol) was dissolved in glacial acetic acid (8.0 mL), ammonium acetate (0.5 g, 6.5 mmol) was added, and the resulting mixture was heated at 100° C. under a nitrogen atmosphere for 3 h. After the removal of the solvent in vacuo, the residue was partitioned between water (50 mL) and EtOAc (30 mL). The organic phase was washed with water (2×25 mL), dried ($Na_2SO_4$), filtered, and concentrated under reduced pressure. The resulting material was purified by flash column chromatography on silica gel, eluting with 40% EtOAc in hexane, to provide 0.45 g (58%) of 4-[2-[4-[[3-fluoro-5-(3,4,5,6-tetrahydro-4-methoxypyran-4-yl)phenoxy]methyl]phenylmethyl]-4-phenyloxazol-5-yl]benzenesulfonamide as a white amorphous material: m.p. 93–99° C. $^1$H NMR ($CDCl_3$/300 MHz) δ 8.19 (d, 2H, J=8.4 Hz), 7.92 (d, 2H, J=8.1 Hz), 7.82 (d, 2H, J=8.7 Hz), 7.68 (m, 2H), 7.57 (d, 2H, J=8.1 Hz), 7.45 (m, 3H), 6.84 (s, 1H), 6.73 (d, 1H, J=9.9 Hz), 6.64 (d, 1h, J=9.9 Hz), 5.14 (s, 2H), 4.84 (s, 2H), 3.83 (m, 4H), 2.99 (s, 3H), 1.97 (m, 4H); FABMS m/z=615 (M+H). HRMS calcd for $C_{34}H_{32}FN_2SO_6$ 615.1965, found 615.1937.

EXAMPLE 16

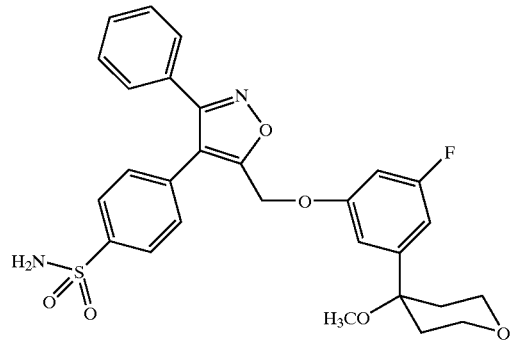

4-[5-[[3-Fluoro-5-(3,4,5,6-tetrahydro-4-methoxypyran-4-yl)phenoxy]methyl]-3-phenylisoxazol-4-yl]benzenesulfonamide A solution of 4-[5-methyl-3-phenylisoxazol-4-yl]benzenesulfonamide (1.0 g, 3.2 mmol) and N,N,N',N'-tetramethylethylenediamine (1.12 g, 9.6 mmol) in tetrahydrofuran (100 mL) was cooled to -78° C. Butyllithium (6 mL, 1.6 M, 9.6 mmol) was then added to this solution. After 30 min, hexachloroethane (2.27 g, 9.6 mmol) was added to the reaction mixture, the reaction mixture was warmed to -30° C., and then quenched with dilute hydrochloric acid. The reaction mixture was extracted with ethyl acetate (100 mL), washed with brine, dried and concentrated to afford a 1:1 mixture of the desired 5-chloromethyl isoxazole product and the starting material as an inseparable mixture, which was carried to the next stage without further purification. The crude 5-chloromethyl isoxazole (0.25 g, 0.718 mmol) was added to a solution of 3-fluoro-5-(4-methoxy-3,4,5,6-tetrahydro-2H-pyran-4-yl)phenol (Example 8, Step 4) (0.324 g) in dioxane (5 mL) and aqueous sodium hydroxide (1N, 2.86 mL), and the reaction mixture was stirred for 3 days at room temperature. The reaction mixture was diluted with water (20 mL) and extracted with ethyl acetate (2×20 mL). The organic layers were combined and washed with water and brine, dried, filtered, and concentrated. The resulting residue was purified by flash column chromatography on silica gel, eluting with 1:2 ethyl acetate in hexane, to give 0.130 g (67%) of 4-[5-[[3-fluoro-5-(3,4,5,6-tetrahydro-4-methoxypyran-4-yl)-phenoxy]-methyl]-3-phenylisoxazol-4-yl]benzenesulfonamide as a crystalline solid: $^1$H NMR (CDCl$_3$/300 MHz) δ 7.93 (d, 2H, J=8.5 Hz), 7.42–7.36 (m, 7H), 6.78–6.54 (m, 3H), 5.15 (s, 2H), 3.79–3.82 (m, 4H), 2.99 (s, 3H), 1.88–1.86 (m, 4H). FABMS m/z=545 (M+Li). HRMS calcd for $C_{28}H_{27}N_2FO_6S$ 538.1652. Found 539.1652 (M+H).

EXAMPLE 17

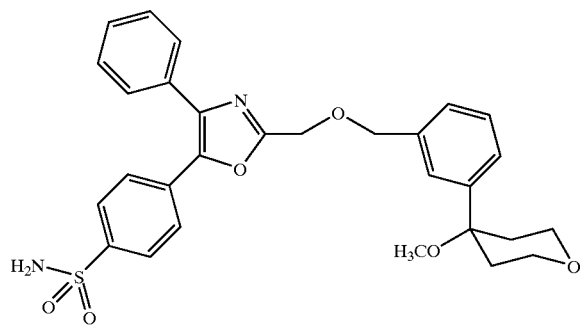

4-[2-[[[3-(3,4,5,6-Tetrahydro-4-methoxypyran-4-yl) phenylmethyl]oxy]methyl]-4-phenyloxazol-5-yl] benzenesulfonamide Step 1. Preparation of methyl 3-[(4-methoxy)tetrahydropyran-4-yl]phenyl-methoxyacetate.

A solution of methyl glycolate (0.35 g, 3.9 mmol) in 5 mL of anhydrous DMF was added to a suspension of sodium hydride (0.11 g, 4.6 mmol) in 5 mL of anhydrous DMF at 5° C., and the reaction mixture was stirred for 40 minutes at 5° C. A solution of 3-[(4-methoxy)tetrahydropyran-4-yl]-α-bromotoluene (1 g, 3.9 mmol) in 10 mL of anhydrous DMF was added to the cold methyl glycolate solution while maintaining the temperature at 5° C. The mixture was stirred for 2 h at 5° C., then for 18 h at room temperature. The mixture was quenched with water (100 mL) and the aqueous solution was extracted with ethyl acetate (2×100 mL). The combined organic extracts were washed with saturated brine (1×100 mL), dried over magnesium sulfate, filtered and concentrated. The concentrated residue was purified by flash column chromatography on silica gel, eluting with 25% ethyl acetate in hexane, to give 0.57 g (50%) of methyl 3-[(4-methoxy)-tetrahydropyran-4-yl]phenylmethoxyacetate as a clear oil: HRMS calcd for $C_{16}H_{22}O_5$ 295.1545. Found 295.1502.

Step 2. Preparation of 3-[(4-methoxy)-tetrahydropyran-4-yl] phenylmethoxy-acetic acid.

A solution of methyl 3-[(4-methoxy)-tetrahydropyran-4-yl]phenylmethoxy-acetate (Step 1) (0.5 g, 1.7 mmol) and LiOH (0.18 g, 4.25 mmol) in 10% water and methanol (5 mL) was stirred for 6 h at room temperature. The solvents were removed at reduced pressure, and the concentrated residue was partitioned between ethyl acetate (100 mL) and 1 N HCl (30 mL). The organic layer was separated and washed with saturated brine (1×100 mL), dried over magnesium sulfate, filtered and concentrated. The concentrated residue was vacuum dried to give 0.46 g (97%) of 3-[(4-methoxy)-tetrahydropyran-4-yl]phenyl-methoxyacetic acid as a yellow solid: HRMS calcd for $C_{15}H_{20}O_5$ 280.1311. Found 280.1304.

Step 3. Preparation of 4-[2-[[[3-(3,4,5,6-tetrahydro-4-methoxypyran-4-yl)phenylmethyl]oxy]methyl]-4-phenyloxazol-5-yl]benzenesulfonamide.

An aqueous solution of 2.5 N NaOH (1.2 mL, 2.7 mmol) was added to 3-[(4-methoxy)tetrahydropyran-4-yl]phenyl-methoxyacetic acid (0.76 g, 2.7 mmol) in ethanol (10 mL), and the mixture was stirred for 15 min at room temperature. The solvents were removed at reduced pressure. Several mL of absolute ethanol were added to this concentrated residue, and the mixture was again concentrated at reduced pressure. This procedure was repeated three times until a white solid formed, which was dried under high vacuum. The resulting carboxylic acid sodium salt was suspended in 4 mL of anhydrous DMF. A solution of 2-bromo-2-[(4-amino-sulfonyl)phenyl]-1-phenyl-ethanone (1.1 g, 2.7 mmol) in 4 mL of DMF was added at room temperature. The reaction mixture was stirred for 18 h at room temperature, and the DMF was removed at reduced pressure. Ethyl acetate (100 mL) was added to this concentrated residue, and this mixture was filtered. The filtrate was concentrated and dried to give the desired crude α-acyloxy ketone. Acetic acid (5 mL) and ammonium acetate (0.8 g, 10 mmol) were added to this concentrated residue, and this mixture was heated at 100° C. for 3 h. The reaction mixture was cooled to room temperature, and the excess acetic acid was removed under vacuum. The resulting residue was partitioned between water (100 mL) and ethyl acetate (100 mL). The organic layer was separated, washed with saturated aqueous sodium bicarbonate (2×100 mL), saturated brine (1×100 mL), dried over magnesium sulfate, filtered and concentrated. The concentrated residue was purified by flash column chromatography on silica gel, eluting with 20% to 45% ethyl acetate in hexane, to give 0.19 g (13%) of 4-[2-[[[3-(3,4,5,6-tetrahydro-4-methoxypyran-4-yl)phenylmethyl]oxy]methyl]-4-phenyloxazol-5-yl]benzenesulfonamide as a white solid: m.p. 62.1–71.2° C. $^1$H NMR (CDCl$_3$/300 MHz) δ 1.91–1.95 (m, 4H), 2.94 (s, 3H), 3.75–3.88 (m, 4H), 4.73 (s, 2H), 4.74 (s, 2H), 4.92 (s, 2H), 7.30–7.44 (m, 7H), 7.60–7.63 (m, 2H), 7.73–7.76 (m, 2H), 7.89–7.92 (m, 2H). HRMS calcd for $C_{29}H_{30}N_2O_6S$ 535.1903. Found 535.1865.

EXAMPLE 18

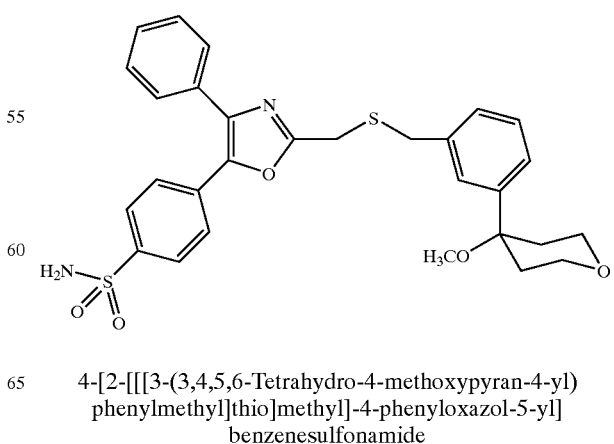

4-[2-[[[3-(3,4,5,6-Tetrahydro-4-methoxypyran-4-yl) phenylmethyl]thio]methyl]-4-phenyloxazol-5-yl] benzenesulfonamide Step 1. Preparation of Methyl 3-[(4-methoxy)-tetrahydropyran-4-yl]phenyl-methylthioacetate.

A solution of 3-[(4-methoxy)tetrahydropyran-4-yl]-α-bromotoluene (1.0 g, 3.87 mmol) in 10 mL of anhydrous THF was cooled to 5° C. A solution of methyl thioglycolate (0.41 g, 3.87 mmol) and DBU (0.59 g, 3.87 mmol) in 10 mL of THF was added while maintaining the temperature at 5° C. The reaction mixture was stirred for 2 h at room temperature. The reaction mixture was diluted with 250 mL of ethyl acetate, and the organic layer was washed with 1 N HCl (2×100 mL), saturated sodium bicarbonate (1×100 mL), brine (1×100 mL), dried over magnesium sulfate, filtered and concentrated. The concentrated residue was purified by flash column chromatography on silica gel, eluting with 40% ethyl acetate in hexane, to give 0.87 g (72%) of methyl 3-[(4-methoxy)-tetrahydropyran-4-yl]phenyl-methylthioacetate as a clear oil: $^1$H NMR (CDCl$_3$/300 MHz) δ 1.94–2.09 (m, 4H), 2.97 (s, 3H), 3.08 (s, 2H), 3.73 (s, 3H), 3.77–3.92 (m, 6H), 7.26–7.36 (m, 4H). HRMS calcd for C$_{16}$H$_{22}$O$_4$S 311.1317. Found 311.1271.

Step 2. Preparation of 3-[(4-methoxy)-tetrahydropyran-4-yl]phenylmethyl-thioacetic acid.

A solution of methyl 3-[(4-methoxy)-tetrahydropyran-4-yl]phenylmethyl-thioacetate (Step 1) (0.8 g, 2.58 mmol) and LiOH (0.27 g, 6.44 mmol) in 10% water and methanol (10 mL) was stirred for 18 h at room temperature. The solvents were removed at reduced pressure, and the concentrated residue was partitioned between ethyl acetate (200 mL) and 1 N HCl (100 mL). The organic layer was separated and washed with saturated brine (1×100 mL), dried over magnesium sulfate, filtered and concentrated. The concentrated residue was vacuum dried to give 0.75 g (98%) of 3-[(4-methoxy)-tetrahydropyran-4-yl]phenyl-methylthioacetic acid as a clear oil: $^1$H NMR (CDCl$_3$/300 MHz) δ 1.94–2.10 (m, 4H), 2.11 (s, 1H), 2.98 (s, 3H), 3.10 (s, 2H), 3.81–3.91 (m, 6H), 7.28–7.38 (m, 4H). HRMS calcd for C$_{15}$H$_{20}$O$_4$S 297.1161. Found 297.1140.

Step 3. Preparation of 4-[2-[[[3-(3,4,5,6-tetrahydro-4-methoxypyran-4-yl)phenylmethyl]thio]methyl]-4-phenyloxazol-5-yl]benzenesulfonamide.

An aqueous solution of 2.5 N NaOH (0.97 mL, 2.43 mmol) was added to a solution of 3-[(4-methoxy)-tetrahydropyran-4-yl]phenylmethylthioacetic acid (Step 2) (0.72 g, 2.43 mmol) in ethanol (10 mL), and the mixture was stirred for 15 min at room temperature. The solvents were removed at reduced pressure. Several mL of absolute ethanol were added to this concentrated residue, and the mixture was again concentrated at reduced pressure. This procedure was repeated three times until a white solid formed, which was dried under high vacuum. The resulting carboxylic acid sodium salt was suspended in 10 mL of anhydrous DMF. A solution of 2-bromo-2-[(4-aminosulfonyl)phenyl]-1-phenylethanone (Example 8, Step 1) (0.86 g, 2.43 mmol) in 8 mL of DMF was added at room temperature. The reaction mixture was stirred for 1 h at room temperature, and the DMF was removed at reduced pressure. Ethyl acetate (100 mL) was added to this concentrated residue, and this mixture was filtered. The filtrate was concentrated and dried to give the desired crude α-acyloxy ketone. Acetic acid (5 mL) and ammonium acetate (0.8 g, 10 mmol) were added to this concentrated residue, and the mixture was heated at 100° C. for 2 h. The mixture was cooled to room temperature, and the excess acetic acid was removed under vacuum. The resulting residue was partitioned between water (100 mL) and ethyl acetate (250 mL). The organic layer was separated, washed with saturated aqueous sodium bicarbonate (2×100 mL), saturated brine (1×100 mL), dried over magnesium sulfate, filtered and concentrated. The concentrated residue was purified by flash column chromatography on silica gel, eluting with 40% ethyl acetate in hexane, to give 0.28 g (21%) or 4-[2-[[[3-(3,4,5,6-tetrahydro-4-methoxypyran-4-yl)phenylmethyl]thio]methyl]-4-phenyl-oxazol-5-yl]benzenesulfonamide as a white solid: m.p. 77.2–81.7° C. $^1$H NMR (CDCl$_3$/300 MHz) δ 1.80–1.94 (m, 4H), 2.93 (s, 3H), 3.76–3.86 (m, 6H), 3.90 (s, 2H), 4.96 (s, 2H), 7.24–7.32 (m, 3H), 7.41–7.44 (m, 4H), 7.61–7.64 (m, 2H), 7.71 (bd, 2H, J=8.40 Hz), 7.91 (bd, 2H, J=8.40 Hz). HRMS calcd for C$_{29}$H$_{30}$N$_2$O$_5$S$_2$ 551.1674. Found 551.1668.

EXAMPLE 19

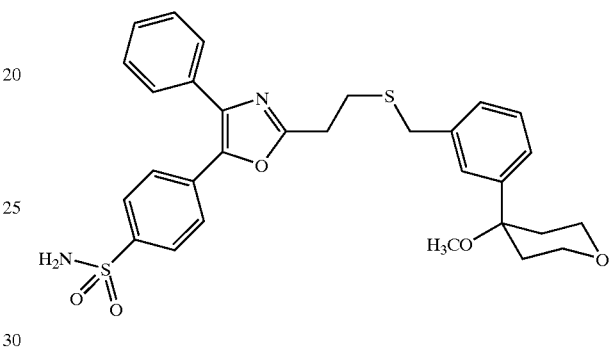

4-[2-[[[3-(3,4,5,6-Tetrahydro-4-methoxypyran-4-yl)phenylmethyl]thio]ethyl]-4-phenyloxazol-5-yl]benzenesulfonamide Step 1. Preparation of methyl 3-[[(4-methoxy)tetrahydropyran-4-yl]phenyl-methylthio]propionate.

A solution of 3-[(4-methoxy)tetrahydropyran-4-yl]-α-bromotoluene (1.0 g, 3.87 mmol) in 10 mL of anhydrous THF was cooled to 5° C. A solution of methyl 3-mercaptopropionate (0.46 g, 3.87 mmol) and DBU (0.59 g, 3.87 mmol) in 10 mL of THF was added while maintaining the temperature at 5° C. The reaction mixture was stirred for 1 h at 5° C. and for 18 h at room temperature. The reaction mixture was diluted with 200 mL of ethyl acetate, and this solution was washed with 1 N HCl (1×100 mL), saturated sodium bicarbonate (1×100 mL), brine (1×100 mL), dried over magnesium sulfate, filtered and concentrated. The concentrated residue was purified by flash column chromatography on silica gel, eluting with 20% ethyl acetate in hexane, to give 0.94 g (75%) of methyl 3-[[(4-methoxy)-tetrahydro-pyran-4-yl]phenylmethylthio]propionate as a pink oil: $^1$H NMR (CDCl$_3$/300 MHz) δ 1.93–2.09 (m, 4H), 2.54 (t, 2H, J=7.4 Hz), 2.68 (t, 2H, J=7.5 Hz), 2.97 (s, 3H), 3.68 (s, 3H), 3.75 (s, 2H), 3.80–3.92 (m, 4H), 7.23–7.36 (m, 4H). HRMS calcd for C$_{17}$H$_{24}$O$_4$S 325.1474. Found 325.1494.

Step 2. Preparation of 3-[[(4-methoxy)tetrahydropyran-4-yl]phenylmethyl-thio]propionic acid.

A solution of methyl 3-[[(4-methoxy)tetrahydropyran-4-yl]phenyl-methyl-thio]propionate (Step 1) (0.91 g, 2.8 mmol) and LiOH (0.29 g, 7.01 mmol) in 10% water and methanol (10 mL) was stirred for 18 h at room temperature. The solvents were removed at reduced pressure, and the concentrated residue was partitioned between ethyl acetate (200 mL) and 1 N HCl (100 mL). The organic layer was separated and washed with saturated brine (1×100 mL), dried over magnesium sulfate, filtered and concentrated. The concentrated residue was vacuum dried to give 0.9 g of 3-[[(4-methoxy)tetrahydropyran-4-yl]phenylmethyl-thio] propionic acid as a clear, colorless oil: HRMS calcd for $C_{16}H_{22}O_4S$ 310.1239, found 310.1241.

Step 3. Preparation of 4-[2-[2-[[5-(3,4,5,6-tetrahydro-4-methoxypyran-4-yl)phenyl-methyl]thio]ethyl]-4-phenyloxazol-5-yl]benzenesulfonamide.

An aqueous solution of 2.5 N NaOH (1.03 mL, 2.6 mmol) was added to a solution of 3-[[(4-methoxy)tetrahydropyran-4-yl]phenylmethylthio]propionic acid (0.8 g, 2.6 mmol) in ethanol (10 mL), and the mixture was stirred for 15 min at room temperature. The solvents were removed at reduced pressure. Several mL of absolute ethanol were added to the concentrated residue, and the mixture was again concentrated at reduced pressure. This procedure was repeated three times until a white solid formed, which was dried under high vacuum. The resulting carboxylic acid sodium salt was suspended in 10 mL of anhydrous DMF and combined with a solution of 2-bromo-2-[(4-aminosulfonyl)phenyl]-1-phenylethanone (Example 8, Step 1) (0.91 g, 2.6 mmol) in 10 mL of DMF. The resulting mixture was stirred for 18 h at room temperature, and the DMF was removed at reduced pressure. Ethyl acetate (100 mL) was added to this concentrated residue, and this mixture was filtered. The filtrate was concentrated and dried to give the desired crude α-acyloxy ketone. Acetic acid (5 mL) and ammonium acetate (0.8 g, 10 mmol) were added to this concentrated residue, and this mixture was heated at 100° C. for 2 h. The reaction mixture was cooled to room temperature, and the excess acetic acid was removed under vacuum. The resulting residue was partitioned between water (100 mL) and ethyl acetate (250 mL). The organic layer was separated, washed with saturated aqueous sodium bicarbonate (2×100 mL), saturated brine (1×100 mL), dried over magnesium sulfate, filtered and concentrated. The concentrated residue was purified by flash column chromatography on silica gel, eluting with 40% to 45% ethyl acetate in hexane, to give 0.06 g (4%) of 4-(2-[2-[[5-(3,4,5,6-tetrahydro-4-methoxy-pyran-4-yl)phenyl-methyl]thio]ethyl]-4-phenyloxazol-5-yl]benzenesulfonamide as a white solid: m.p. 60.9–66.4° C. $^1$H NMR (CDCl$_3$/300 MHz) δ 1.93–2.01 (m, 4H), 2.91–2.95 (m, 5H), 3.12 (t, 2H, J=7.20 Hz), 3.76–3.87 (m, 6H), 4.50 (s, 2H), 7.29–7.43 (m, 7H), 7.58–7.61 (m, 2H), 7.69–7.72 (m, 2H), 7.88–7.91 (m, 2H). HRMS calcd for $C_{30}H_{32}N_2O_5S_2$ 565.1831. Found 565.1852.

EXAMPLE 20

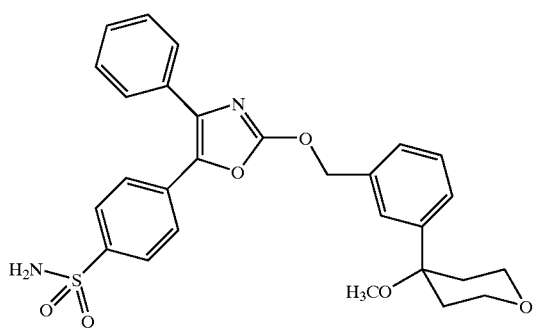

4-[2-[3-(3,4,5,6-Tetrahydro-4-methoxypyran-4-yl)phenyl]methoxy]-4-phenyloxazol-5-yl3benzenesulfonamide A solution of 3-[tetrahydro-(4-methoxy)pyran-4-yl]benzyl alcohol (prepared as described in U.S. Pat. No. 5,424,320) (0.07 g, 0.3 mmol) in 2 mL of anhydrous DMA was added to a suspension of sodium hydride (7.2 mg, 0.3 mmol) in 2 mL of anhydrous DMA at 5° C., and the reaction mixture was stirred for 20 minutes at 5° C. A solution of 4-[(2-chloro)-4-phenyloxazol-5-yl]benzenesulfonamide in 2 mL of anhydrous DMA was then added. The reaction mixture was stirred for 2 h at 5° C. and for 5 h at room temperature. The reaction mixture was quenched with water (50 mL). The aqueous solution was extracted with ethyl acetate (2×50 mL). The combined organic layers were washed with saturated brine (1×100 mL), dried over magnesium sulfate, filtered and concentrated. The concentrated residue was purified by flash column chromatography on silica gel, eluting with 40% ethyl acetate in hexane, to give 0.1 g (64%) of 4-[2-[3-(3,4,5,6-tetrahydro-4-methoxypyran-4-yl)phenyl]methoxy]-4-phenyloxazol-5-yl]-benzenesulfonamide as a white solid:

$^1$H NMR (CDCl$_3$/300 MHz) δ 1.95–2.06 (m, 4H), 2.98 (s, 3H), 3.81–3.88 (m, 4H), 4.81 (s, 2H), 5.53 (s, 2H), 7.39–7.46 (m, 6H), 7.55–7.67 (m, 5H), 7.84 (d, 2H, J=8.70 Hz). HRMS calcd for $C_{28}H_{28}N_2O_6S$ 521.1746. Found 521.1701.

EXAMPLE 21

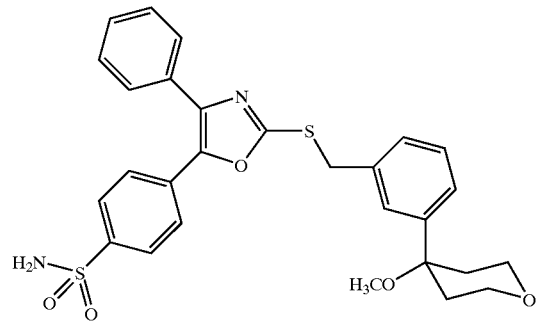

4-[2-[3-(3,4,5,6-Tetrahydro-4-methoxypyran-4-yl)phenyl]methylthio]-4-phenyloxazol-5-yl]benzenesulfonamide To a solution of 4-[(2-chloro)-4-phenyloxazol-5-yl]benzenesulfonamide (0.21 g, 0.63 mmol) in 2 mL of anhydrous THF at 5° C. was added a solution of 3-[tetrahydro-(4-methoxy)pyran-4-yl]benzyl mercaptan (prepared as described in U.S. Pat. No. 5,424,320) (0.15 g, 0.63 mmol) and DBU (95 mg, 0.63 mmol) in 5 mL of THF while maintaining the temperature at 5° C. The reaction mixture was stirred for 1 h at 5° C. for 5 h at room temperature. The reaction mixture was diluted with 100 mL of ethyl acetate and washed with 1 N HCl (1×100 mL), saturated aqueous NaHCO$_3$ (1×100 mL), brine (1×100 mL), dried over magnesium sulfate, filtered and concentrated. The concentrated residue was purified by flash column chromatography on silica gel, eluting with 40% ethyl acetate in hexane, to give 0.19 g (56%) of 4-[2-[3-(3,4,5,6-tetrahydro-4-methoxypyran-4-yl)phenyl]methylthio]-4-phenyloxazol-5-yl]benzenesulfonamide as a white solid: m.p. 74.7–78.5° C. $^1$H NMR (CDCl$_3$/300 MHz) δ 1.85–1.97 (m, 4H), 2.92 (s, 3H), 3.71–3.85 (m, 4H), 4.48 (s, 2H), 4.87 (s, 2H), 7.29–7.47 (m, 7H), 7.60–7.69 (m, 4H), 7.86–7.90 (m, 2H). HRMS calcd for $C_{28}H_{28}N_2O_5S_2$ 537.1518. Found 537.1516.

EXAMPLE 22

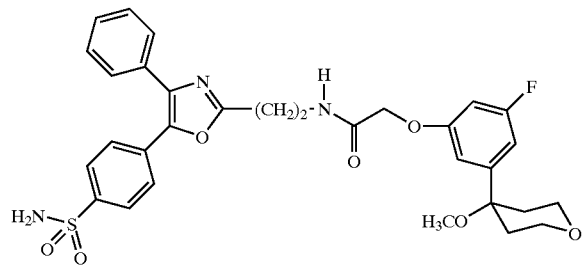

N-[2-[5-[4-(Aminosulfonyl)phenyl]-4-phenyloxazol-2-yl]ethylamino]-2-[3-fluoro-5-(3,4,5,6-tetrahydro-4-methoxypyran-4-yl)phenoxy]acetamide Step 1. Preparation of 4-[2-[2-(N-phenylmethoxycarbonylamino)ethyl]-4-phenyloxazol-5-yl]benzenesulfonamide.

A mixture of N-phenylmethoxycarbonyl-β-alanine (1.5 g, 6.7 mmol) and 2-bromo-2-[(4-aminosulfonyl)phenyl]-1-phenylethanone (Example 8, Step 1) (2.0 g, 5.65 mmol) in dimethylacetamide (10.00 mL) was treated with $K_2CO_3$ (0.47 g, 3.4 mmol) and 18-crown-6 (0.033 g) and stirred at room temperature for 16 h. After the removal of the solvent in vacuo, the residue was partitioned between cold water (25 mL) and EtOAc (50 mL). The organic phase was washed with water (2×25 mL), dried ($Na_2SO_4$), and concentrated under reduced pressure. The resulting substance (2.8 g) was purified by flash column chromatography on silica gel, eluting with 40% EtOAc in hexane, to afford the desired benzoin ester (2.0 g) as an amorphous substance which was used without further purification. The benzoin ester (1.6 g) was dissolved in glacial acetic acid (16 mL), treated with ammonium acetate (1.25 g, 16.2 mmol) and heated at 90° C. under a nitrogen atmosphere for 3 h. After the removal of the solvent in vacuo, the residue was partitioned between water (50 mL) and EtOAc (50 mL). The organic phase was washed with water (2×25 mL), dried ($Na_2SO_4$), and concentrated under reduced pressure. The resulting material was purified by flash column chromatography on silica gel, eluting with 50% EtOAc in hexane, to provide 0.85 (55%) of 4-[2-[2-(N-phenylmethoxycarbonyl-amino)ethyl]-4-phenyloxazol-5-yl]benzenesulfonamide as a white amorphous material: $^1$H NMR ($CDCl_3$/300 MHz) δ 7.86 (d, 2H, J=8.4 Hz), 7.69 (d, 2H, J=8.4 Hz), 7.59 (m, 2H), 7.40 (m, 3H), 7.33 (m, 5H), 5.45 (br, 1H), 5.10 (s, 2H), 4.91 (s, 2H), 3.74 (q, 2H, J=6.0 Hz), 3.09 (t, 2H, J=6.0 Hz).; FABMS m/z=478 (M+H). HRMS calcd for $C_{25}H_{24}N_3O_5S$ 478.1437. Found 478.1412.

Step 2. Preparation of 4-[2-(2-aminoethyl)-4-phenyloxazol-5-yl]benzenesulfonamide.

A solution of 4-[2-[2-(N-phenylmethoxycarbonylamino)ethyl]-4-phenyl-oxazol-5-yl]benzenesulfonamide (Step 1) (0.75 g, 1.6 mmol) in MeOH (15 mL) containing acetic acid (0.1 mL) was treated with 10% Pd on carbon (0.35 g) and stirred under an atmosphere of hydrogen at 50 psi at room temperature for 2.5 h. The catalyst was removed by filtration, and the filtrate was concentrated under reduced pressure to afford a white powder which was purified by reverse-phase HPLC using a gradient of 10–90% $CH_3CN$ in $H_2O$ to afford 0.55 g of 4-[2-(2-aminoethyl)-4-phenyloxazol-5-yl]benzenesulfonamide as its trifluoroacetate salt: $^1$H NMR ($CD_3OD$/300 MHz) δ 7.91 (d, 2H, J=7.9 Hz), 7.74 (m, 2H,), 7.63 (m, 2H), 7.44 (m, 3H), 3.49 (t, 2H, J=6.6 Hz), 3.33 (t, 2H, J=6.6 Hz). FABMS m/z=344 (M+H). HRMS calcd for $C_{17}H_{18}N_3O_5S$ 344.1069. Found 344.1048.

Step 3. Preparation of N-[2-[5-[4-(aminosulfonyl)phenyl]-4-phenyloxazol-2-yl]ethylamino]-2-[3-fluoro-5-(3,4,5,6-tetrahydro-4-methoxypyran-4-yl)phenoxy]-acetamide.

To a solution of 3-fluoro-5-(4-methoxy-3,4,5,6-tetrahydro-2H-pyran-4-yl)-phenoxyacetic acid (0.24 g, 0.85 mmol) (Example 8, Step 3) in dimethylacetamide (2.00 mL) and dichloromethane (3.00 mL), HOBt (0.18 g, 1.18 mmol) and EDC (0.17 g, 0.89 mmol) were added, and the resulting mixture was stirred at 0° C. for 1 h. This reaction mixture was treated with a solution of the free amine generated by the addition of N-methylmorpholine (0.1 mL) to a solution of 4-[2-(2-aminoethyl)-4-phenyloxazol-5-yl]benzenesulfonamide trifluoroacetate (0.3 g, 0.51 mmol) in dimethylacetamide (1.0 mL) at 0° C. The resulting mixture was warmed to room temperature in 16 h. The reaction mixture was diluted with dichloromethane (20 mL), and washed sequentially with 5% citric acid, (2×10 mL), saturated $NaHCO_3$ (2×10 mL), water, and dried ($Na_2SO_4$). After the removal of the solvent under reduced pressure, the residue was purified by flash column chromatography on silica gel, eluting with 80% EtOAc in hexane, to afford 0.31 g (52%) of N-[2-[5-[4-(aminosulfonyl)phenyl]-4-phenyloxazol-2-yl]ethylamino]-2-[3-fluoro-5-(3,4,5,6-tetrahydro-4-methoxy-pyran-4-yl)phenoxy]acetamide as a white amorphous substance: $^1$H NMR ($CDCl_3$/300 MHz) δ 7.88 (d, 2H, J=8.7 Hz), 7.72 (d, 2H, J=8.7 Hz), 7.58 (m, 3H), 7.43 (m, 3H), 6.74 (d, 1H, J=9.6 Hz) 6.7 (m, 1H), 6.48 (m, 1H), 4.97 (s, 2H), 4.51 (s, 2H), 3.9 (q, 2H, J=6.0 Hz), 3.79 (m, 4H), 3.13 (t, 2H, J=6.3 Hz), 2.95 (s, 3H), 1.84 (m, 4H). FABMS m/z=610 (M+H). HRMS calcd for $C_{31}H_{33}N_3O_7FS$ 610.2023. Found 610.2016.

Biological Evaluation

Rat Carrageenan Foot Pad Edema Test

The carrageenan foot edema test was performed with materials, reagents and procedures essentially as described by winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in *Non-steroidal Anti-Inflammatory Drugs*, (J. Lombardino, ed. 1985)). The % inhibition shows the % decrease from control paw volume determined in this procedure and the data for selected compounds in this invention are summarized in Table I.

TABLE I

RAT PAW EDEMA

| Example | % Inhibition @ 10 mg/kg body weight |
|---------|--------------------------------------|
| 3       | 15                                   |

Evaluation of COX-1 and COX-2 Activity in vitro

The compounds of this invention exhibited inhibition in vitro of COX-2. The COX-2 inhibit on activity of the compounds or this invention illustrated in the Examples was determined by the following methods.

a. Preparation of Recombinant COX Baculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamHI site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells ($2 \times 10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer ($10^7$–$10^8$ pfu/ml) stocks of virus were prepared. For large scale production, SF9 insect cells were infected in 10 liter fermentors ($0.5 \times 10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at –80° C. before being assayed for COX activity.

b. Assay for COX-1 and COX-2 Activity

COX activity was assayed as $PGE_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The $PGE_2$ formed was measured by standard ELISA technology (Cayman Chemical). Results are shown in Table II.

Assay for 5-Lipoxygenase Activity

The 5-lipoxygenase (5-LO) activity of the compounds were determined by the calcium ionophore-induced Leukotriene B4 (LTB4) production in human whole blood. Venous blood was collected from healthy human donors using heparin as an anti-coagulant. Human blood samples (0.2 ml of a 1:4 dilution in RPMI 1640 medium) were incubated in 96-well culture plates for 15 minutes at 37° C. with test compounds dissolved in ethanol (EtOH; final concentration<1%), or vehicle. Typically 7 concentrations of test compounds were examined in duplicate. A-23187 [Sigma] was added to the blood to a final concentration of 20 µg/ml, and the mixtures were incubated for 10 minutes at 37° C. The reaction was stopped by placing the samples on ice. The samples were then centrifuged at 800×g at 4° C. for 10 minutes to pellet the cells, and the supernatants were recovered for quantitation of LTB4 by LISA (Cayman Chemical Co.; sensitivity 3 pg/ml). $IC_{50}$'s were estimated from a four parameter logistic model with two parameters fixed, the minimum (0% inhibition) and maximum (100% inhibition). The $IC_{50}$ value is the concentration that produces 50% inhibition between the fixed values of the minimum and maximum. Data is reported as the mean $IC_{50}$ for each compound. Results are shown in Table II.

TABLE II

| Example | COX-2 $IC_{50}$ (µM) | COX-1 $IC_{50}$ (µM) | 5-LO $IC_{50}$ (µM) |
|---------|----------------------|----------------------|---------------------|
| 1       | <0.1                 | 38                   | 0.15                |
| 2       | 0.2                  | >10                  | 0.05                |
| 3       | <0.1                 | >100                 | 0.02                |
| 4       | <0.1                 | <0.1                 | 14                  |
| 5       | <0.1                 | <0.1                 | 17                  |
| 6       | <0.1                 | 2.2                  | 0.44                |
| 7       | <0.1                 | 3.8                  | 0.65                |
| 8       | <0.1                 | 1.3                  | 0.3                 |
| 9       | 10                   | 80                   | >10                 |
| 12      | <0.1                 | >100                 | >10                 |
| 14      | <0.1                 | 5.0                  | 0.2                 |
| 16      | <0.1                 | >100                 | >10                 |
| 17      | 0.5                  | >100                 | 9.8                 |
| 19      | <0.1                 | 2.3                  | >10                 |
| 21      | <0.1                 | 2.6                  | >10                 |
| 22      | 1.1                  | >100                 | >10                 |

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly (IV), intraperitoneally, subcutaneously, intramuscularly (IM) or topically.

For oral administration, the pharmaceutical composition may be in the form of, for example, a tablet, hard or soft capsule, lozenges, dispensable powders, suspension or liquid. The pharmaceutical composition is preferably made in the form of a dosage unit containing a particular amount of the active ingredient. Examples of such dosage units are tablets or capsules.

The active ingredient may also be administered by injection (IV, IM, subcutaneous or jet) as a composition wherein, for example, saline, dextrose, or water may be used as a suitable carrier. The pH of the composition may be adjusted, if necessary, with suitable acid, base, or buffer. Suitable bulking, dispersing, wetting or suspending agents, including mannitol and PEG 400, may also be included in the composition. A suitable parenteral composition can also include a compound formulated as a sterile solid substance, including lyophilized powder, in injection vials. Aqueous solution can be added to dissolve the compound prior to injection.

The amount of therapeutically active compounds that are administered and the dosage regimen for treating a disease condition with the compounds and/or compositions of this invention depends on a variety of factors, including the age, weight, sex and medical condition of he subject, the severity of the inflammation or inflammation related disorder, the route and frequency of administration, and the particular compound employed, and thus may vary widely. The pro-drug compositions should include similar dosages as for the parent compounds. The pharmaceutical compositions may contain active ingredients in the range of about 0.1 to 1000 mg, preferably in the range of about 0.5 to 250 mg and most preferably between about 1 and 60 mg. A daily dose of about 0.01 to 100 mg/kg body weight, preferably between about 0.05 and about 20 mg/kg body weight and most preferably between about 0.1 to 10 mg/kg body weight, may be appropriate. The daily dose can be administered in one to four doses per day.

In the case of skin conditions, it may be preferable to apply a topical preparation of compounds of this invention to the affected area two to four times a day.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the way together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound or a pharmaceutically acceptable salt of the compound, wherein:

the compound corresponds in structure to Formula I:

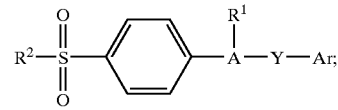

A is pyrazolyl optionally substituted with a radical selected from the group consisting of acyl, halo, alkyl, haloalkyl, cyano, nitro, carboxyl, alkoxy, oxo, aminocarbonyl, alkoxycarbonyl, carboxyalkyl, cyanoalkyl, and hydroxyalkyl;

Y is selected from the group consisting of oxy, thio, sulfinyl, sulfonyl, alkyl, alkenyl, alkynyl, alkyloxy, alkylthio, alkylcarbonyl, cycloalkyl, aryl, haloalkyl, hydroxyalkyl, hydroxyalkyloxy, hydroxyalkyloxyalkyl, hydroxyalkylthio, hydroxyalkylthioalkyl, oximinoalkoxy, oximinoalkoxyalkyl, (alkyl)oximinoalkoxy, (alkyl)oximinoalkoxyalkyl, oximinoalkylthio, oximinoalkylthioalkyl, (alkyl)oximinoalkylthio, (alkyl)oximinoalkylthioalkyl, carbonylalkyloxy, carbonylalkyloxyalkyl, carbonylalkylthio, carbonylalkylthioalkyl, cycloalkenyl, aralkyl, acyl, alkylthioalkyl, alkyloxyalkyl, alkenylthio, alkynylthio, alkenyloxy, alkynyloxy, alkenylthioalkyl, alkynylthioalkyl, alkenyloxyalkyl, alkynyloxyalkyl, arylcarbonyl, aralkylcarbonyl, aralkenyl, haloalkylcarbonyl, alkoxyalkyl, alkylaminocarbonylalkyl, arylthioalkyl, aryloxyalkyl, haloaryloxyalkyl, aralkylthioalkyl, aralkoxyalkyl, alkoxyaralkoxyalkyl, alkoxycarbonylalkyl, alkoxycarbonylcyanoalkenyl, aminocarbonylalkyl, N-alkylaminocarbonyl, N-arylaminocarbonyl, N,N-dialkylaminocarbonyl, N-alkyl-N-arylaminocarbonyl, cycloalkylaminocarbonyl, carboxyalkylaminocarbonyl, alkylcarbonylalkyl, aralkoxycarbonylalkylaminocarbonyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyl-N-aralkylamino, N-alkyl-N-arylamino, aminoalkyl, N-alkylaminoalkyl, N,N-dialkylaminoalkyl, N-arylaminoalkyl, N-aralkylaminoalkyl, N-alkyl-N-aralkylaminoalkyl, N-alkyl-N-arylaminoalkyl, aminoalkoxy, aminoalkoxyalkyl, aminoalkylthio, aminoalkylthioalkyl, cycloalkyloxy, cycloalkylalkyloxy, cycloalkylthio, cycloalkylalkylthio, aryloxy, aralkoxy, arylthio, aralkylthio, alkylsulfinyl, alkylsulfonyl, aminosulfonyl, N-alkylaminosulfonyl, N-arylaminosulfonyl, arylsulfonyl, N,N-dialkylaminosulfonyl, N-alkyl-N-arylaminosulfonyl,

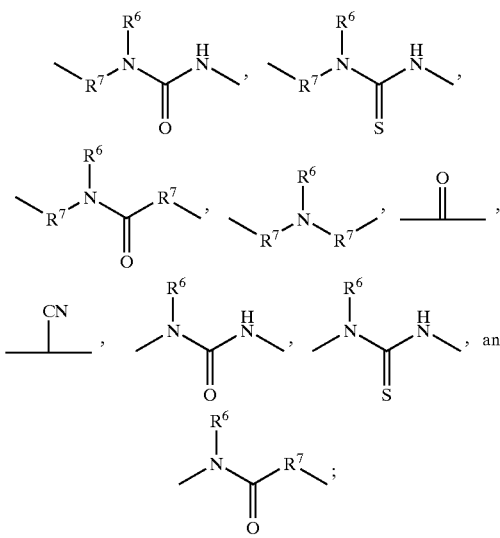

Ar is aryl optionally substituted with one or two substituents selected from the group consisting of halo, hydroxyl, amino, nitro, cyano, carbamoyl, alkyl, alkenyloxy, alkoxy, alkylthio, alkylsulfinyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, and alkoxycarbonylalkoxy, and

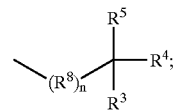

$R^1$ is one or more substituents selected from the group consisting of cycloalkyl, cycloalkenyl, and aryl, wherein:
any such substituent is optionally substituted with one or more radicals selected from the group consisting of alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy, and alkylthio;

$R^2$ is selected from the group consisting of alkyl and amino;

$R^3$, $R^4$, and the carbon atom to which $R^3$ and $R^4$ are attached together form tetrahydropyranyl optionally substituted with up to three substituents independently selected from the group consisting of hydroxyl, alkyl, alkoxy, alkenyloxy, and alkynyloxy;

$R^5$ is selected from the group consisting of hydroxyl, alkoxy, alkylcarbonyloxy, and arylcarbonyloxy;

$R^6$ is selected from the group consisting of hydrido, alkyl, aryl, and aralkyl;

$R^7$ is selected from the group consisting of alkyl, alkenyl, and alkynyl;

$R^8$ is oximino optionally substituted with alkyl; and n is zero or 1.

2. A compound or salt of claim 1, wherein:

A is pyrazolyl optionally substituted with a radical selected from the group consisting of acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl, Y is selected from the group consisting of oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl) oximinoalkoxy, lower (alkyl)oximinoalkoxyalkyl, lower carbonylalkyloxy, lower carbonylalkyloxyalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylthio, lower alkylcarbonyl, lower cycloalkyl, phenyl, lower haloalkyl, lower cycloalkenyl, lower aralkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower arylthioalkyl, lower aryloxyalkyl, lower aralkylthioalkyl, lower aralkoxyalkyl, lower alkoxyaralkoxyalkyl, lower alkoxycarbonylalkyl, lower alkoxycarbonylcyanoalkenyl, lower aminocarbonylalkyl, lower N-alkylaminocarbonyl, N-phenylaminocarbonyl, lower N,N-dialkylaminocarbonyl, lower N-alkyl-N-arylaminocarbonyl, lower cycloalkylaminocarbonyl, lower carboxyalkylaminocarbonyl, lower alkylcarbonylalkyl, lower aralkoxycarbonylalkylaminocarbonyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-phenylamino, lower N-aralkylamino, lower N-alkyl-N-aralkylamino, lower N-alkyl-N-aralkylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, lower aminoalkoxy, lower aminoalkoxyalkyl, lower aminoalkylthio, lower aminoalkylthioalkyl, lower cycloalkyloxy, lower cycloalkylalkyloxy, lower cycloalkylthio, lower cycloalkylalkylthio, phenyloxy, lower aralkoxy, phenylthio, lower aralkylthio, lower alkylsulfinyl, lower alkylsulfonyl, aminosulfonyl, lower N-alkylaminosulfonyl, lower N-arylaminosulfonyl, lower arylsulfonyl, lower N,N-dialkylaminosulfonyl, lower N-alkyl-N-arylaminosulfonyl,

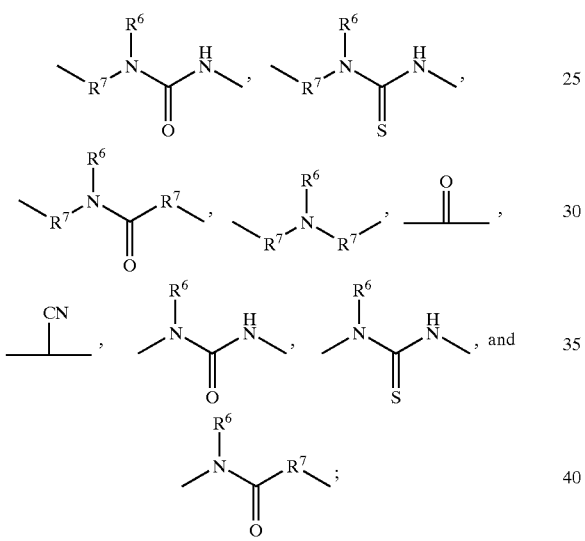

Ar is selected from the group consisting of phenyl, biphenyl, and naphthyl, wherein:
  the phenyl, biphenyl, or naphthyl is optionally substituted with one or two substituents selected from the group consisting of halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, and lower alkoxycarbonylalkoxy, and

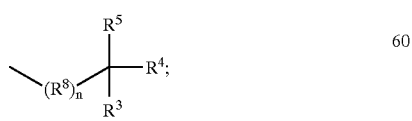

$R^1$ is at least one substituent selected from the group consisting of lower cycloalkyl, lower cycloalkenyl, phenyl, biphenyl, and naphthyl, wherein:

any such substituent is optionally substituted with one or more radicals selected from the group consisting of lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy, and lower alkylthio;

$R^2$ is selected from the group consisting of lower alkyl and amino;

$R^3$, $R^4$, and the carbon atom to which $R^3$ and $R^4$ are attached together form tetrahydropyranyl optionally substituted with up to, three substituents independently selected from the group consisting of hydroxyl, lower alkyl, lower alkoxy, lower alkenyloxy, and lower alkynyloxy;

$R^5$ is selected from the group consisting of hydroxyl, lower alkoxy, lower alkylcarbonyloxy, and phenylcarbonyloxy;

$R^6$ is selected from the group consisting of hydrido, lower alkyl, phenyl and lower aralkyl;

$R^7$ is selected from the group consisting of lower alkyl, lower alkenyl, and lower alkynyl;

$R^8$ is oximino optionally substituted with alkyl; and n is zero or 1.

3. A compound or salt of claim 2, wherein:

A is pyrazolyl optionally substituted with a radical selected from the group consisting of acyl, halo, lower alkyl, lower haloalkyl, oxo, cyano, nitro carboxyl, lower alkoxy, aminocarbonyl, lower alkoxycarbonyl, lower carboxyalkyl, lower cyanoalkyl, and lower hydroxyalkyl;

Y is selected from the group consisting of oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl) oximinoalkoxy, lower (alkyl) oximinoalkoxyalkyl, lower carbonylalkyloxy, lower carbonylalkyloxyalkyl, lower hydroxyalkylthio, lower hydroxyalkylthioalkyl, lower oximinoalkalkylthio, lower oximinoalkylthioalkyl, lower (alkyl) oximinoalkylthio, lower (alkyl) oximinoalkylthioalkyl, lower carbonylalkylthio, lower carbonylalkylthioalkyl, lower alkylthio, lower alkylcarbonyl, lower cycloalkyl, phenyl, lower haloalkyl, lower cycloalkenyl, lower aralkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower arylthioalkyl, lower aryloxyalkyl, lower aralkylthioalkyl, lower aralkoxyalkyl, lower alkoxycarbonylalkyl, lower aminocarbonylalkyl, lower N-alkylaminocarbonyl, N-phenylaminocarbonyl, lower alkylcarbonylalkyl, lower N-alkylamino, N-phenylamino, lower N-aralkylamino, lower aminoalkyl, lower N-alkylaminoalkyl, lower N-arylaminoalkyl, lower N-aralkylaminoalkyl, lower aminoalkoxy, lower aminoalkoxyalkyl, lower aminoalkylthio, lower aminoalkylthioalkyl, lower cycloalkyloxy, lower cycloalkylalkyloxy, lower cycloalkylthio, lower cycloalkylalkylthio, phenyloxy, lower aralkoxy, phenylthio, lower aralkylthio, lower alkylsulfinyl, lower alkylsulfonyl, aminosulfonyl, lower N-alkylaminosulfonyl, N-phenylaminosulfonyl, phenylsulfonyl, oximino, $$\diagdown_{R^7}\!\!\diagup^{\!\!R^6}\!\!\diagdown_{R^7}\,,\quad \underset{\parallel}{\overset{O}{\diagdown\!\!\diagup}}\,,\text{ and }\underset{}{\overset{CN}{\diagdown\!\!\diagup}}\,;$$

Ar is selected from the group consisting of phenyl, biphenyl, and naphthyl, wherein:
  the phenyl, biphenyl, or naphthyl is optionally substituted with one or two substituents selected from the group consisting of halo, hydroxyl, amino, nitro, cyano, lower alkyl, lower alkoxy, and $$\underset{R^3}{\overset{R^5}{{-}\!\!\!\!\!\!\!-}}\!\!-R^4;$$

$R^1$ is at least one substituent selected from the group consisting of phenyl, biphenyl, and naphthyl, wherein:
  any such substituent is optionally substituted with one or more radicals selected from the group consisting of lower alkyl, lower haloalkyl, cyano, carboxyl, lower alkoxycarbonyl, hydroxyl, lower hydroxyalkyl, lower haloalkoxy, amino, nitro, lower alkoxyalkyl, lower alkylsulfinyl, halo, lower alkoxy, and lower alkylthio;
$R^2$ is selected from the group consisting of lower alkyl and amino;
$R^3$, $R^4$, and the carbon to which $R^3$ and $R^4$ are attached together form a tetrahydropyran ring optionally substituted with up to three substituents independently selected from the group consisting of hydroxyl, lower alkyl, and lower alkoxy;
$R^5$ is selected from the group consisting of hydroxyl and lower alkoxy;
$R^6$ is selected from the group consisting of hydrido, lower alkyl, phenyl and lower aralkyl; and
$R^7$ is selected from the group consisting of lower alkyl, lower alkenyl, and lower alkynyl.

4. A compound or salt of claim 3, wherein:
A is pyrazolyl optionally substituted with a radical selected from the group consisting of acyl, halo, lower alkyl, lower haloalkyl, oxo, cyano, carboxyl, lower alkoxy, aminocarbonyl, lower alkoxycarbonyl, lower carboxyalkyl, lower cyanoalkyl, and lower hydroxyalkyl;
Y is selected from the group consisting of oxy, thio, sulfinyl, sulfonyl, lower alkyl, lower alkynyl, aryl, lower cycloalkyl, aralkyl, lower alkyloxy, aryloxy, arylthio, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkyloxyalkyl, lower alkylthioalkyl, lower hydroxyalkyloxy, lower alkoxycarbonylalkyl, lower hydroxyalkyloxyalkyl, lower oximinoalkoxy, lower oximinoalkoxyalkyl, lower (alkyl) oximinoalkoxy, lower (alkyl) oximinoalkoxyalkyl, lower carbonylalkyloxy, lower carbonylalkyloxyalkyl, $$\diagdown_{R^7}\!\!\diagup^{\!\!R^6}\!\!\diagdown_{R^7}\,,\text{ and }\underset{\overset{\parallel}{O}}{\overset{R^6}{\diagdown\!\!\mathrm{N}\!\!\diagup\!\!-\!\!R^7}}\,;$$

Ar is phenyl optionally substituted with one or two substituents selected from the group consisting of halo, hydroxyl, lower alkyl, lower alkoxy, and $$\underset{R^3}{\overset{R^5}{{-}\!\!\!\!\!\!\!-}}\!\!-R^4;$$

$R^1$ is at least one substituent selected from the group consisting of cyclopentenyl and phenyl, wherein:
  any such substituent is optionally substituted with one or more radicals selected from the group consisting of lower alkyl, lower haloalkyl, hydroxyl, lower hydroxyalkyl, lower haloalkoxy, nitro, lower alkoxyalkyl, halo, lower alkoxy, and lower alkylthio;
$R^2$ is selected from the group consisting of lower alkyl and amino;
$R^3$, $R^4$, and the carbon to which $R^3$ and $R^4$ are attached together form a tetrahydropyran ring optionally substituted with up to three substituents independently selected from the group consisting of hydroxyl, lower alkyl, and lower alkoxy;
$R^5$ is selected from the group consisting of hydroxyl and lower alkoxy;
$R^6$ is selected from the group consisting of hydrido, and lower alkyl; and
$R^7$ is lower alkyl.

5. A compound or salt of claim 4, wherein:
A is pyrazolyl optionally substituted with a radical selected from the group consisting of acyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl;
Y is selected from the group consisting of oxy, ethyl, propyl, isopropyl, butyl, 1-propynyl, 2-propynyl, methyloxy, ethyloxy, propyloxy, methylthio, (Z)-1-propenyloxy, (E)-2-propenyloxy, (Z)-2-propenyloxy, (E)-1-propenyloxy, (Z)-1-propenyloxymethyl, (E)-2-propenyloxymethyl, (Z)-2-propenyloxymethyl, (E)-1-propenyloxymethyl, 1-propynyloxy, 2 -propynyloxy, 1-propynylthio, 2-propynylthio, hydroxymethyloxy, 1-hydroxyethyloxy, 2-hydroxypropyloxy, hydroxymethyloxymethyl, 1-hydroxyethyloxymethyl, 2-hydroxypropyloxymethyl, methyloxymethyl, ethyloxymethyl, propyloxymethyl, 1-propynyloxymethyl, oximinomethyloxy, oximinomethyloxymethyl, (methyl)oximinomethyloxy, (methyl)oximinomethyloxymethyl, 1-(methoxymethyl)ethyl, methylthiomethyl, ethylthiomethyl, N-ethyl-N-methylaminocarbonylmethyloxy, N-ethyl-N-methylaminoethyloxy, carbonylmethyloxy, carbonylbutyloxy, and carbonylmethyloxymethyl;
Ar is phenyl optionally substituted with one or two substituents selected from the group consisting of fluoro, chloro, bromo, hydroxyl, methyl, methoxy, and $$\begin{array}{c} R^5 \\ | \\ \text{—}\!\!\!\!\!+\!\!\!\!\!\text{—} R^4; \\ | \\ R^3 \end{array}$$

$R^1$ is selected from the group consisting of phenyl optionally substituted with one or more radicals selected from the group consisting of methyl, trifluoromethyl, hydroxyl, hydroxymethyl, trifluoromethoxy, nitro, methoxymethyl, fluoro, chloro, bromo, methoxy, and methylthio;

$R^2$ is methyl or amino;

$R^3$, $R^4$, and the carbon to which $R^3$ and $R^4$ are attached together form a tetrahydropyran ring optionally substituted with up to three substituents independently selected from the group consisting of hydroxyl, methyl, and methoxy; and $R^5$ is selected from the group consisting of hydroxyl and methoxy.

6. A compound or salt of claim 5, wherein the compound is selected from the group consisting of:
- 4-[5-(4-chlorophenyl)-3-(3-methoxyphenyl)oxymethyl-1H-pyrazol-1-yl]benzenesulfonamide;
- 4-[5-(4-chlorophenyl)-3-(3-methoxyphenyl)thiomethyl-1H-pyrazol-1-yl]benzenesulfonamide;
- 4-[5-(4-chlorophenyl)-3-[[3-fluoro-5-(3,4,5,6-tetrahydro-4-methoxy-2H-pyran-4-yl)phenoxy]-1H-pyrazol-1-yl]benzenesulfonamide; and
- 4-[5-(4-chlorophenyl)-3-[[3-fluoro-5-(3,4,5,6-tetrahydro-4-methoxy-2H-pyran-4-yl)phenoxy]methyl]-1H-pyrazol-1-yl]benzenesulfonamide.

7. A compound or pharmaceutically acceptable salt of the compound, wherein:

the compound corresponds in structure to Formula II:

A is a pyrazolyl optionally substituted with a radical selected from the group consisting of acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

Y is selected from the group consisting of oxy, thio, sulfinyl, sulfonyl, lower alkyl, lower alkynyl, lower alkenyl, lower hydroxyalkyl, aryl, lower cycloalkyl, aralkyl, lower alkyloxy, aryloxy, arylthio, lower cycloalkyloxy, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkyloxyalkyl, lower alkylthioalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, and lower carbonylalkyloxyalkyl;

$R^1$ is a substituent selected from the group consisting of lower cycloalkyl, lower cycloalkenyl, phenyl, biphenyl, and naphthyl, wherein:
any such substituent is optionally substituted with one or more radicals selected from the group consisting of lower alkyl, lower haloalkyl, cyano, carboxyl, lower alkoxycarbonyl, hydroxyl, lower hydroxyalkyl, lower haloalkoxy, amino, lower alkylamino, phenylamino, lower alkoxyalkyl, lower alkylsulfinyl, halo, lower alkoxy, and lower alkylthio;

$R^2$ is selected from the group consisting of lower alkyl and amino;

$R^9$ is one or two substituents selected from the group consisting of halo, hydroxyl, amino, nitro, cyano, carbamoyl, alkyl, alkenyloxy, alkoxy, alkylthio, alkylsulfinyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, and alkoxycarbonylalkoxy; and $R^{10}$ is selected from the group consisting of hydrido, alkyl, alkenyl, alkynyl, cyanoalkyl, alkanoyl, and benzoyl optionally substituted with a substituent selected from the group consisting of halo, alkyl and alkoxy.

8. A compound or salt of claim 7, wherein:

A is pyrazolyl optionally substituted with a radical selected from the group consisting of acyl, halo, hydroxyl, lower alkyl, lower haloalkyl, oxo cyano, nitro, carboxyl, lower alkoxy, aminocarbonyl, lower alkoxycarbonyl, lower carboxyalkyl, lower cyanoalkyl, and lower hydroxyalkyl;

Y is selected from the group consisting of oxy, lower alkyl, lower alkynyl, lower hydroxyalkyl, lower alkyloxy, lower alkylthio, lower alkyloxyalkyl, lower alkenyloxy, lower alkenyloxyalkyl, lower alkynyloxy, lower alkynylthio, lower alkynyloxyalkyl, lower alkylthioalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, and lower carbonylalkyloxyalkyl;

$R^1$ is phenyl optionally substituted with one or more radicals selected from the group consisting of lower alkyl, lower haloalkyl, hydroxyl, lower hydroxyalkyl, halo, and lower alkoxy;

$R^2$ is selected from the group consisting of lower alkyl and amino;

$R^9$ is one or two substituents selected from the group consisting of halo, hydroxyl, amino, lower alkyl, lower alkoxy; and $R^{10}$ is selected from the group consisting of hydrido and lower alkyl.

9. A compound or salt of claim 8, wherein:

A is pyrazolyl optionally substituted with a radical selected from the group consisting of formyl, fluoro, chloro, bromo, hydroxyl, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, oxo, cyano, nitro, carboxyl, methoxy, ethoxy, propoxy, n-butoxy, pentoxy, hexyloxy, methylenedioxy, aminocarbonyl, methoxycarbonyl, carboxypropyl, carboxymethyl, carboxyethyl, cyanomethyl, and hydroxymethyl;

Y is selected from the group consisting of oxy, ethyl, propyl, isopropyl, butyl, 1-propynyl, 2-propynyl, methyloxy, ethyloxy, propyloxy, methylthio, (Z)-1-propenyloxy, (e)-2-propenyloxy, (Z)-2-propenyloxy, (E)-1-propenyloxy, (Z)-1-propenyloxymethyl, (E)-2-propenyloxymethyl, (Z)-2-propenyloxymethyl, (E)-1-propenyloxymethyl, 1-propynyloxy, 2-propynyloxy, 1-propynylthio, 2-propynylthio, hydroxymethyl, hydroxyethyl, hydroxypropyl, hydroxymethyloxy, 1-hydroxyethyloxy, 2-hydroxypropyloxy, hydroxymethyloxymethyl, 1-hydroxyethylxoymethyl, 2-hydroxypropyloxymethyl, methyloxymethyl, ethyloxymethyl, propyloxymethyl, 1-propynyloxymethyl, hydroxymethylthio, 1-hydroxyethylthio, 2-hydroxypropylthio, 1-hydroxyethylthio, 2-hydroxpropylthio, hydroxymethylthiomethyl, 1-hydroxyethylthiomethyl, 2-hydroxypropylthiomethyl, oximinomethylthio, oximinomethylthiomethyl, (methyl)oximinomethylthio, (methyl)oximinomethylthiomethyl, carbonylmethylthio, carbonylbutylthio, carbonylmethylthiomethyl, oximinomethyloxy, oximinomethyloxymethyl, (methyl)oximinomethyloxy, methylthiomethyl, (methyl)oximinomethyloxymethyl, ethylthiomethyl, 1-(methoxycarbonyl)ethyl, carbonylmethyloxy, carbonylbutyloxy, and carbonylmethyloxymethyl;

$R^1$ is phenyl optionally substituted with one or more radicals selected from the group consisting of methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, fluoro, dichloropropyl, hydroxyl, hydroxymethyl, chloro, bromo, methoxy, ethoxy, propoxy, n-butoxy, pentoxy, and hexyloxy;

$R^2$ is selected from the group consisting of methyl and amino;

$R^9$ is one or two substituents selected from the group consisting of fluoro, chloro, bromo, hydroxyl, amino, methyl, ethyl, isopropyl, butyl, tert-butyl, isobutyl, pentyl, hexyl, methoxy, ethoxy, propoxy, n-butoxy, pentoxy, and hexyloxy; and $R^{10}$ is selected from the group consisting of hydrido and methyl.

10. A pharmaceutical composition comprising a therapeutically-effective amount of a compound or salt of claim 1.

11. A pharmaceutical composition comprising a therapeutically-effective amount of a compound or salt of claim 7.

* * * * *